(12) United States Patent
Baxter et al.

(10) Patent No.: US 10,241,045 B2
(45) Date of Patent: Mar. 26, 2019

(54) SPECTRALLY ENCODED MICROBEADS AND METHODS AND DEVICES FOR MAKING AND USING SAME

(71) Applicant: The Regents of the University of California, Oakland, CA (US)

(72) Inventors: Brian Cullen Baxter, Santa Clara, CA (US); Joseph L. Derisi, San Francisco, CA (US); Polly M. Fordyce, San Francisco, CA (US); Rachel E. Gerver, Oakland, CA (US); Rafael Gòmez-Sjöberg, Menlo Park, CA (US); Brett A. Helms, San Francisco, CA (US); Kurt S. Thorn, San Francisco, CA (US); Ronald N. Zuckermann, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 817 days.

(21) Appl. No.: 14/420,320

(22) PCT Filed: Aug. 22, 2013

(86) PCT No.: PCT/US2013/056280
§ 371 (c)(1),
(2) Date: Feb. 6, 2015

(87) PCT Pub. No.: WO2014/031902
PCT Pub. Date: Feb. 27, 2014

(65) Prior Publication Data
US 2015/0192518 A1    Jul. 9, 2015

Related U.S. Application Data

(60) Provisional application No. 61/692,618, filed on Aug. 23, 2012.

(51) Int. Cl.
| | | |
|---|---|---|
| *G01N 21/64* | (2006.01) | |
| *C40B 60/00* | (2006.01) | |
| *B01F 5/06* | (2006.01) | |
| *B01F 13/00* | (2006.01) | |
| *B01F 13/10* | (2006.01) | |
| *B01F 3/08* | (2006.01) | |
| *G01N 33/58* | (2006.01) | |
| *C08F 2/44* | (2006.01) | |
| *B82Y 30/00* | (2011.01) | |
| *C08F 222/38* | (2006.01) | |

(52) U.S. Cl.
CPC .......... *G01N 21/64* (2013.01); *B01F 3/0807* (2013.01); *B01F 3/0861* (2013.01); *B01F 5/061* (2013.01); *B01F 13/0059* (2013.01); *B01F 13/0062* (2013.01); *B01F 13/1027* (2013.01); *C08F 2/44* (2013.01); *G01N 33/585* (2013.01); *G01N 33/587* (2013.01); *B01F 2005/0623* (2013.01); *B01F 2005/0636* (2013.01); *B82Y 30/00* (2013.01); *C08F 222/385* (2013.01); *G01N 2201/061* (2013.01); *G01N 2458/40* (2013.01)

(58) Field of Classification Search
None
See application file for complete search history.

(56) References Cited

U.S. PATENT DOCUMENTS

| | | | |
|---|---|---|---|
| 3,250,722 | A | 5/1966 | Borchardt |
| 3,412,245 | A | 11/1968 | Halverson |
| 3,473,027 | A | 10/1969 | Freeman |
| 4,018,635 | A | 4/1977 | Ryan et al. |
| 4,283,382 | A | 8/1981 | Frank et al. |
| 4,341,957 | A | 7/1982 | Wieder |
| 4,491,620 | A | 1/1985 | Joiner, Jr. |
| 4,600,389 | A | 7/1986 | Schwartz |
| 4,816,344 | A | 3/1989 | Chiang |
| 5,043,265 | A | 8/1991 | Tanke et al. |
| 5,329,127 | A | 7/1994 | Becker et al. |
| 5,674,698 | A | 10/1997 | Zarling et al. |
| 5,698,397 | A | 12/1997 | Zarling et al. |
| 5,891,656 | A | 4/1999 | Zarling et al. |
| 5,955,601 | A | 9/1999 | Sherman et al. |
| 6,159,686 | A | 12/2000 | Kardos et al. |

(Continued)

FOREIGN PATENT DOCUMENTS

| | | |
|---|---|---|
| EP | 1491350 A2 | 12/2004 |
| EP | 1491350 A3 | 8/2005 |

(Continued)

OTHER PUBLICATIONS

Vancaeyzeele et al., Lanthanide-Containing Polymeric Nanoparticles for Biological Tagging Applications: Nonspecific Endocytosis and Cell Adhesion, Journal of the American Chemical Society, 2007, 129, 13653-13660.*

(Continued)

*Primary Examiner* — Amy M Bunker
(74) *Attorney, Agent, or Firm* — Michael B. Rubin; Bozicevic, Field & Francis LLP

(57) ABSTRACT

Spectrally encoded microbeads and methods and devices for making and using spectrally encoded microbeads are provided. The disclosed methods and devices facilitate the preparation and use of microbeads containing multiple lanthanide nanoparticles, which microbeads have uniquely identifiable spectral codes. The disclosed microbeads, and the methods and devices for making and using same, find use in multiplexing and high-throughput biomarker analysis.

3 Claims, 27 Drawing Sheets
Specification includes a Sequence Listing.

(56) References Cited

U.S. PATENT DOCUMENTS

| | | | |
|---|---|---|---|
| 6,201,989 B1 | 3/2001 | Whitehead et al. | |
| 6,203,726 B1 | 3/2001 | Danielson et al. | |
| 6,207,130 B1 | 3/2001 | Kareiva et al. | |
| 6,399,397 B1 | 6/2002 | Zarling et al. | |
| 6,403,947 B1 | 6/2002 | Hoyt et al. | |
| 6,514,295 B1 | 2/2003 | Chandler et al. | |
| 6,528,165 B2 | 3/2003 | Chandler | |
| 6,536,672 B1 | 3/2003 | Outwater | |
| 6,537,829 B1 | 3/2003 | Zarling et al. | |
| 6,552,290 B1 | 4/2003 | Lawandy | |
| 6,617,583 B1 | 9/2003 | Bawendi et al. | |
| 6,692,031 B2 | 2/2004 | McGrew | |
| 7,141,431 B2 | 11/2006 | Chandler et al. | |
| 7,309,568 B2 | 12/2007 | Oshida et al. | |
| 7,862,892 B2 | 1/2011 | Chan et al. | |
| 8,673,107 B2 | 3/2014 | Haushalter | |
| 8,696,952 B2* | 4/2014 | Kumacheva | B01F 3/0807 264/4.1 |
| 8,796,030 B2 | 8/2014 | Haushalter | |
| 8,927,892 B2 | 1/2015 | Haushalter | |
| 2001/0049101 A1 | 12/2001 | Brogger et al. | |
| 2002/0022273 A1 | 2/2002 | Empedocles | |
| 2002/0025490 A1 | 2/2002 | Shchegolikhin et al. | |
| 2002/0041372 A1 | 4/2002 | Gardner et al. | |
| 2003/0002029 A1 | 1/2003 | Dukler et al. | |
| 2003/0098357 A1 | 5/2003 | Cummings et al. | |
| 2003/0129296 A1 | 7/2003 | Kelso | |
| 2003/0180482 A1 | 9/2003 | Narita et al. | |
| 2003/0207331 A1 | 11/2003 | Wilson et al. | |
| 2004/0072233 A1 | 4/2004 | Kauvar et al. | |
| 2004/0099740 A1 | 5/2004 | Chresand et al. | |
| 2004/0217298 A1 | 11/2004 | Bawendi et al. | |
| 2004/0217364 A1 | 11/2004 | Tarsa et al. | |
| 2005/0056183 A1 | 3/2005 | Meshireri | |
| 2005/0136486 A1 | 6/2005 | Haushalter | |
| 2005/0208543 A1 | 9/2005 | Vann et al. | |
| 2006/0067883 A1 | 3/2006 | Krom et al. | |
| 2007/0011023 A1 | 1/2007 | Silverbrook | |
| 2007/0172426 A1 | 7/2007 | Lee et al. | |
| 2007/0218009 A1 | 9/2007 | van Veggel et al. | |
| 2007/0286810 A1 | 12/2007 | Hovinen et al. | |
| 2009/0117340 A1 | 5/2009 | Halfyard et al. | |
| 2009/0159510 A1 | 6/2009 | Haushalter | |
| 2009/0218805 A1 | 9/2009 | Haushalter | |
| 2010/0144056 A1 | 6/2010 | Winnik et al. | |
| 2011/0104052 A1* | 5/2011 | Barnett | A61K 9/0019 424/1.21 |
| 2011/0229580 A1 | 9/2011 | Srivastava et al. | |
| 2012/0000777 A1* | 1/2012 | Garrell | B01F 3/0807 204/451 |
| 2012/0156490 A1* | 6/2012 | Fournier-Bidoz | C40B 20/04 428/402 |
| 2014/0336061 A1 | 11/2014 | Haushalter | |

FOREIGN PATENT DOCUMENTS

| | | |
|---|---|---|
| WO | WO 198904826 | 6/1989 |
| WO | WO 2004096714 | 11/2004 |
| WO | WO 2006017140 | 2/2006 |
| WO | 2006/047621 | 5/2006 |
| WO | WO 2006047621 | 5/2006 |
| WO | 2007/051035 | 5/2007 |
| WO | WO 2007051035 | 5/2007 |

OTHER PUBLICATIONS

Steinbacher et al., Polymer Chemistry Flow: New Polymers, Beads, Capsules, and Fibers, Journal of Polymer Science Part A: Polymer Chemistry, 2006, 44, 6505-6533. (Year: 2006).*

Abdelrahman, A., Lantanide-Encoded Polystyrene Microspheres for Mass Cytometry-Based Bioassays, Thesis, University of Toronto, Canada, 1-219. (Year: 2011).*

Liang et al., The Synthesis and Characterization of Lanthanide-Encoded Poly(styrene-co-methacrylic acid) Micropheres, Polymer, 2011, 52, 5040-5052. (Year: 2011).*

Saralidze et al., Polymeric Microspheres for Medical Applications, Materials, 2010, 3, 3537-3564. (Year: 2010).*

Vancaeyzeele et al., Lanthanide-Containing Polymer Nanoparticles for Biological Tagging Applications: Nonspecific Endocytosis and Cell Adhesion, J. Amer. Chem. Soc., 2007, 129(44), 13653-13660. (Year: 2007).*

Barnham, K. et al; "Quantum-dot concentrator and thermodynamic model for the global redshift"; *Applied Physics Letters 76*; pp. 1197-1199; (2000).

Besl Paul J and McKay Neil D; "A Method for Registration of 3-D Shapes"; *IEEE Trans Pattern Anal Mach Intell 14*; pp. 239-256; (1992).

Birtwell, S. & Morgan, H.; "Microparticle encoding technologies for high-throughput multiplexed suspension assays"; *Integr. Biol. 1*; pp. 345; (2009).

Braeckmans, K. et al; "Encoding microcarriers: present and future technologies"; *Nat Rev Drug Discov 1*; pp. 447-456; (2002).

Braeckmans, K. et al; "Encoding microcarriers by spatial selective photobleaching"; *Nat Mater 2*; pp. 169-173; (2003).

Brody, J. P. et al; "Significance and statistical errors in the analysis of DNA microarray data"; *PNAS 99*; pp. 12975-12978; (2002).

Cederquist, K. B. et al; "Encoded anisotropic particles for multiplexed bioanalysis"; *Wiley Interdisciplinary Reviews: Nanomedicine and Nanobiotechnology 2*; (2010); pp. 578-600.

Chatten, A. J. et al; "A new approach to modelling quantum dot concentrators"; *Solar Energy Materials and Solar Cells 75*; (2003); pp. 363-371.

Choi, S., Moon, Y.-M. & Jung, H.-K.; "Luminescent properties of PEG-added nanocrystalline YVO4:Eu3+ phosphor prepared by a hydrothermal method"; *Journal of Luminescence 130*; (2010); pp. 549-553.

Edelstein A et al; "Computer Control of Microscopes Using μManager"; in *Current Protocols in Molecular Biology, Supplement 92*; John Wiley & Sons, Inc.; (Oct. 2010); pp. 14.20.1-14.20.17.

Fiorini, Gina S. et al; "Disposable microfluidic devices: fabrication, function, and application"; *BioTechniques 38*; (Mar. 2005); pp. 429-446.

Fournier-Bidoz, Sebastien et al; "Facile and Rapid One-Step Mass Preparation of Quantum-Dot Barcodes"; *Angewandte Chemie International Edition 47*; (2008); pp. 5577-5581.

Gadish Nitzan et al; "High-Throughput Positive-Dielectrophoretic Bioparticle Microconcentrator"; *Anal Chem 78*; (2006); pp. 7870-7876.

Garstecki, Piotr et al; Formation of droplets and bubbles in a microfluidic T-junction-scaling and mechanism of break-up: *Lab Chip 6*; (2006); pp. 437-446.

Huang, X. Y. et al; "Spectral conversion for solar cell efficiency enhancement using $YVO_4:Bi^{3+},Ln^{3+}$(Ln=Dy, Er, Ho, Eu, Sm, and Yb) phosphors"; *J. Appl. Phys. 109*; (2011); pp. 113526-1-113526-7.

Idris, N. M. et al; "Tracking transplanted cells in live animal using upconversion fluorescent nanoparticles"; *Biomaterials 30*; (2009); pp. 5104-5113.

Ji, X.ing-Hu et al; "On-demand preparation of quantum dot-encoded microparticles using a droplet microfluidic system"; *Lab Chip 11*; (2011) pp. 2561-2568.

Ji, Xing-Hu et al; "Integrated parallel microfluidic device for simultaneous preparation of multiplex optical-encoded microbeads with distinct quantum dot barcodes"; *J. Mater. Chem. 21*; (2011); pp. 13380-13387.

Lansford Rusty et al; "Resolution of multiple green fluorescent protein color variants and dyes using two-photon microscopy and imaging spectroscopy"; *J Biomed Opt 6*; (2001); pp. 311-318.

Lawrie, Gwendolyn A. et al; "Synthesis of Optically Complex Core—Shell Colloidal Suspensions: Pathways to Multiplexed Biological Screening"; *Advanced Functional Materials 13*; (2003); pp. 887-896.

Lee, Howon et al; "Colour-barcoded magnetic microparticles for multiplexed bioassays"; *Nat Mater 9*; (2010); pp. 745-749.

(56) References Cited

OTHER PUBLICATIONS

Lee, Jaebeom et al; "Nanoparticle Assemblies with Molecular Springs: A Nanoscale Thermometer"; *Angewandte Chemie, Int. Ed. 44*; (2005); pp. 7439-7442.

Lee, Chia-Yen et al; "Microfluidic Mixing: A Review"; *Int. J. Mol. Sci. 12*; (2011); pp. 3263-3287.

Neeraj, S. et al; "Novel red phosphors for solid state lighting; the system $Bi_xLn_{1-x}VO_4$; $Eu^{3+}/Sm^{3+}$(Ln=Y, Gd)"; *Solid State Communications 131*; (2004); pp. 65-69.

Nicewarner-Peña, Sheila R. et al; "Submicrometer Metallic Barcodes"; *Science 294*; Oct. 5, 2001; pp. 137-141.

Officer, Simon et al; "Novel online security system based on rare-earth-doped glass micro beads"; *Proceedings of the 1 SPIE—The International Society for Optical Engineering, SPIE, USA*; vol. 5310, No. 1; Jan. 20, 2004; pp. 387-395.

Pregibon, Daniel C. et al; "Multifunctional Encoded Particles for High-Throughput Biomolecule Analysis"; *Science* vol. 315; Mar. 9, 2007; pp. 1393-1396.

Ronda, C.R. et al; "Rare earth phosphors: fundamentals and applications"; *Journal of Alloys and Compounds 275-277*; (1998); pp. 669-676.

Segal Aleksandr V. et al; "Generalized-ICP"; (2009) in *Proceedings of Robotics: Science and Systems (RSS)*.

Shojaei-Zadeh, Shahab et al; "Highly crosslinked poly(dimethylsiloxane) microbeads with uniformly dispersed quantum dot nanocrystals"; *Journal of Colloid and Interface Science 363*; (2011); pp. 25-33.

Stroock, Abraham et al; "Chaotic mixer for microchannels"; *SCIENCE* vol. 295; Jan. 25, 2002; pp. 647-651.

Surawski, Peter P. T. et al; "Flow cytometric detection of proteolysis in peptide libraries synthesised on optically encoded supports"; *Molecular. BioSystems. 4*, (2008); pp. 774-778.

Thorsen, Todd et al; "Dynamic Pattern Formation in a Vesicle-Generating Microfluidic Device"; *Physical Review Letters*, vol. 86, No. 18; Apr. 30, 2001; pp. 4163-4166.

Tsurui, Hiromichi et al; "Seven-color fluorescence imaging of tissue samples based on Fourier spectroscopy and singular value decomposition"; *The Journal of Histochemistry & Cytochemistry*48(5); (2000); pp. 653-662.

Unger, Marc et al; "Monolithic Microfabricated Valves and Pumps by Multilayer Soft Lithography"; *Science* vol. 288; Apr. 7, 2000; pp. 113-116.

Van Sark, Wilfried. G.J.H.M. et al; "Photooxidation and Photobleaching of Single CdSe/ZnS Quantum Dots Probed by Room-Temperature Time-Resolved Spectroscopy"; *J. Phys. Chem. B 105*; (2001); pp. 8281-8284.

Van Sark, Wilfried. G.J.H.M. et al; Blueing, Bleaching, and Blinking of Single CdSe/ZnS Quantum Dots. *ChemPhysChem 3*; (2002); pp. 871-879.

Wang, Q. et al; "Layer-by-layer growth of superparamagnetic, fluorescent barcode nanospheres"; *Nanotechnology 18, 405604*; (2007); 7 pages.

Wang, Feng et al; "Recent advances in the chemistry of lanthanide-doped upconversion nanocrystals"; *Chem Soc Rev 38*; (2009); pp. 976-989.

Wang F et al; "Tuning upconversion through energy migration in core-shell nanoparticles"; *Nature Materials 10*; pp. 968-973; (2011).

Wilson, Robert et al; "Encoded Microcarriers for High-Throughput Multiplexed Detection"; *Angewandte Chemie International Edition 45*; (2006); pp. 6104-6117.

Wright, William H. et al; "Flow Cytometry with Upconverting Phosphors Reporters" in *SPIE* vol. 3260, (1998); pp. 245-254.

Xu, Shengqing. et al; "Generation of Monodisperse Particles by Using Microfluidics: Control over Size, Shape, and Composition13"; *Angewandte Chemie International Edition 44*; (2005); pp. 724-728.

Xu, Wen et al; "$YVO_4:Eu^{3+},Bi^{3+}$UV to visible conversion nanofilms used for organic photovoltaic solar cells"; *J. Mater. Chem. 21*; (2011); pp. 12331-12336.

Yan, Bing et al; "$YVO_4$: $RE^{3+}$(RE=Eu, Sm, Dy, Er) Nanophosphors: Facile Hydrothermal Synthesis, Microstructure, and Photoluminescence"; *Journal of Materials Research* 24(10); (Oct. 2009); pp. 3050-3056.

Zhao, Yuanjin et al; "Microfluidic Generation of Multifunctional Quantum Dot Barcode Particles"; *Journal of the American Chemical Society 133*; (2011); pp. 8790-8793.

Zimmermann, Timo; "Spectral imaging and linear unmixing in light microscopy"; *Adv. Biochem. Eng/Biotechnol. 95*; (2005); pp. 245-265.

Abdelrahman, Ahmed I., et al; "Lanthanide-Containing Polymer Microspheres by Multiple-Stage Dispersion Polymerization for Highly Multiplexed Bioassays"; *J. Am. Chem. Soc. 131*; (2009) pp. 15276-15283.

Barlow, D.J., et al; "Continuous and discontinuous protein antigenic determinants"; *NATURE*, vol. 322; Aug. 21, 1986; pp. 747-748.

Beverloo H.B., et al; "Inorganic Phosphors as New Luminescent Labels for Immunocytochemistry and Time-Resolved Microscopy[1]"; *Cytometry 11*; (1990) pp. 784-792.

Beverloo, H.B., et al; "Preparation and Microscopic Visualization of Multicolor Luminescent Immunophosphors [1]"; *Cytometry 13*; (1992); pp. 561-570.

Bradford Jolene A., et al; "Fluorescence-Intensity Multiplexing: Simultaneous Seven-Marker, Two-Color Immunophenotyping Using Flow Cytometry"; Cytometry Part A 61A; (2004); pp. 142-152.

Buissette Valérie, et al; "Colloidal Synthesis of Luminescent Rhabdophane $LaPO_4:Ln^{3+}xH_2O$ (Ln=Ce, Tb, Eu; x≈0.7) Nanocrystals"; *Journal of Materials Chemistry*, vol. 16, No. 19; (2004); pp. 3767-3773.

Buissette Valérie, et al; "Aqueous routes to lanthanide-doped oxide nanophosphors"; *Journal of Materials Chemistry*, vol. 16; (2006); pp. 529-539.

Bünzli, Jean-Claude G. et al; "Taking advantage of luminescent lanthanide ions"; *Chem. Soc. Rev. 34*; (2005); pp. 1048-1077.

Capek, Ignác; "Inverse Emulsion Polymerization of Acrylamide Initiated by Oil- and Water-soluble Initiators: Effect of Emulsifier Concentration"; *Polymer Journal*, vol. 36, No. 10, pp. 793-803 (2004).

Casanova D., et al; "Luminescent lanthanide-ion doped nanoparticles as single-biomolecule labels and oxidant sensors"; *Proc. of SPIE* vol. 6448; (2007); pp. 64480F-1-64480F-9.

Chan, Emory M.; "Combinatorial approaches for developing upconverting nanomaterials: high-throughput screening, modeling, and applications"; *Chem. Soc. Rev*; (2014); 26 pages.

Chen, D. et al.; "Color-tunable luminescence for Bi3+/Ln3+:YVO4 (Ln=Eu, Sm, Dy, Ho) nanophosphors excitable by near-ultraviolet light"; *Phys.Chem.Chem.Phys. 12*; pp. 7775-7778; (2010).

Chen Guanying, et al; "Nanophotonics and Nanochemistry: Controlling the Excitation Dynamics for Frequency Up- and Down-Conversion in Lanthanide-Doped Nanoparticles"; *Accounts of Chemical Research* vol. 46, No. 7; (2013); 1474-1486.

Dejneka, M. J. et al.; "Rare earth-doped glass microbarcodes"; *Proceedings of the National Academy of Sciences 100*; pp. 389-393; (2003).

Deniz Ashok A., et al; "Ratiometric Single-Molecule Studies of Freely Diffusing Biomolecules"; *Annu. Rev. Phys. Chem.52*; (2001); pp. 233-253.

Ehlert, Oliver, et al; "A Four-Color Colloidal Multiplexing Nanoparticle System";, *American Chemical Society, AcsNano* vol. 2, No. 1; (2008); pp. 120-124.

Ekins, Roger P.; "Multi-analyte immunoassay"; *Journal of Pharmaceutical & Biomedical Analysis*, vol. 7, No. 2; pp. 155-168; (1989).

Ekins, Roger, et al; "Development of Microspot Multi-Analyte Ratiometric Immunoassay Using Dual Fluorescent-Labelled Antibodies"; *Analytica Chimaca Acta, 227*; (1989) pp. 73-96.

Elbanowski Marian and Makowska Barbara; "The lanthanides as luminescent probes in investigations of biochemical systems"; *Journal of Photochemistry and Photobiology A: Chemistry 99*; (1996); pp. 85-92.

Enrichi, Francesco; "Luminescent Amino-functionalized or Erbium-doped Silica Spheres for Biological Applications"; *Ann. N.Y. Acad. Sci. 1130*; pp. 262-266; (2008).

(56) References Cited

OTHER PUBLICATIONS

Erdei, S., et al; "Hydrolyzed colloid reaction (HCR) technique for preparation of $YVO_4$, $YPO_4$ and $YV_xP_{1-x}O_4$"; *Materials Letters 21*; (1994); pp. 143-147.

Fulton, R. J. et al.; "Advanced multiplexed analysis with the FlowMetrix™ system"; *Clinical Chemistry 43*; pp. 1749-1756; (1997).

Gao, X. & Nie, S.; "Quantum Dot-Encoded Mesoporous Beads with High Brightness and Uniformity: Rapid Readout Using Flow Cytometry"; *Analytical Chemistry 76*, pp. 2406-2410; (2004).

Gao, X. & Nie, S.; "Quantum Dot-Encoded Beads" *Methods in Molecular Biology*, vol. 303; pp. 61-71; (2005).

Gerver R. E., et al; "Programmable microfluidic synthesis of spectrally encoded microspheres"; *Lab Chip,12*; (2012); pp. 4716-4723.

Gomez-Sjoberg R et al.; "Versatile, Fully Automated, Microfluidic Cell Culture System"; *Anal. Chem. 79*; (2007); pp. 8557-8563.

Gorris, H. H. et al.; "Tuning the Dual Emission of Photon-Upconverting Nanoparticles for Ratiometric Multiplexed Encoding"; *Advanced Materials 23*; pp. 1652-1655; (2011).

Haase, M. et al.; "Synthesis and properties of colloidal lanthanide-doped nanocrystals"; *Journal of Alloys and Compounds 303-304*; pp. 191-197; (2000).

Han, M. et al.; "Quantum-dot-tagged microbeads for multiplexed optical coding of biomolecules"; *Nat Biotech 19*; pp. 631-635; (2001).

Härmä, Harri, et al; "Zeptomole detection sensitivity of prostate-specific antigen in a rapid microtitre plate assay using time resolved fluorescence"; *Luminescence 15*; pp. 351-355; (2000).

Haushalter, J. P. and Faris G W.; "Surface Enhancement of Lanthanide Emission"; Molecular Physics Laboratory, SRI International; (2005); 1 page.

Haushalter, Jeanne P. et al.; "Strategy for photostable proximity bioassays using lanthanides"; *Appl Opt. 46(10)*: Apr. 1, 2007; pp. 1918-1923.

Hemmilä I. and Laitala V.; "Progress in Lanthanides as Luminescent Probes"; *Journal of Fluorescence*, vol. 15, No. 4; (Jul. 2005); pp. 529-542.

Hotz Charles Z.; "Applications of Quantum Dots in Biology"; Methods in Molecular Biology, vol. 303; (2005); pp. 1-17.

Huhtinen Petri, et al; "Synthesis, Characterization, and Application of Eu(III), Tb(III), Sm(III), and Dy(III) Lanthanide Chelate Nanoparticle Labels"; *Anal. Chem. 77*; (2005); pp. 2643-2648.

Huignard Arnaud, et al; "Synthesis and Luminescence Properties of Colloidal $YVO_4$:Eu Phosphors"; *Chem. Mater. 12* (2000); pp. 1090-1094.

Huignard A., et al; "Synthesis and Characterizations of $YVO_4$:Eu Colloids"; *Chem. Mater. 14* (2002); pp. 2264-2269.

Jallapuram, Raghavendra, et al; "Raman spectroscopy for the characterization of the polymerization rate in an acrylamide-based photopolymer"; *Applied Optics*, vol. 47, No. 2; Jan. 10, 2008; pp. 206-212.

Jia Guang, et al; "Facile Synthesis and Luminescence Properties of Highly Uniform $MF/YVO_4$:$Ln^{3+}$(Ln=Eu, Dy, and Sm) Composite Microspheres"; *American Chemical Society, Crystal Growth & Design*, vol. xxx, No. xx; (2009); 5 pages.

Jin, Yu et al; "Microwave-assisted hydrothermal synthesis and multicolor tuning luminescence of YPxV1-xO4:Ln3+ (Ln=Eu, Dy, Sm) nanoparticles"; *Materials Chemistry and Physics 129*; (2011); pp. 418-423.

Kettman, J.R., et al; "Classification and Properties of 64 Multiplexed Microsphere Sets"; *Cytometry 33*; (1998); pp. 234-243.

Kiviniemi Minna; "Homogeneous Assays for Simplified Screening of HLA-conferred Genetic Disease Risk"; *Turun Yliopisto University of Turku*; (2010); pp. 1-70.

Leif, Robert C., et al; "Increasing the Luminescence of Lanthanide Complexes"; *Cytometry Part A 69A*; (2006); pp. 767-778.

Li Liping, et al; "Preparation of cereal-like $YVO_4$:$Ln^{3+}$(Ln=Sm, Eu, Tb, Dy) for high quantum efficiency photoluminescence"; *Nanotechnology 21* (2010); 195601; (8pp).

Liu Yongsheng, et al; "Lanthanide-doped luminescent nanoprobes: controlled synthesis, optical spectroscopy, and bioapplications" Chem. Soc. Rev.; (2013); 4 pages.

Mialon Geneviéve, et al; "High Temperature Strategy for Oxide Nanoparticle Synthesis"; *American Chemical Society*, vol. 2, No. 12; (2008); pp. 2505-2512.

Mialon Geneviéve, et al; "Luminescent oxide nanoparticles with enhanced optical properties"; *Journal of Luminescence 129*; (2009); pp. 1706-1710.

Prasath R. Arun, et al; "Thiol-ene and thiol-yne chemistry in microfluidics: a straightforward method towards macroporous and nonporous functional polymer beads"; *Polym. Chem. 1*; (2010); pp. 685-692.

Rauf Sakandar , et al; "Production of Quantum Dot Barcodes Using Biological Self-Assembly"; *Advance Materials 21* (2009); pp. 4020-4024.

Riwotzki K. and Haase M.; "Wet-Chemical Synthesis of Doped Colloidal Nanoparticles: $YVO_4$:Ln (Ln ) Eu, Sm, Dy)"; *J. Phys. Chem. B 102*; (1998) pp. 10129-10135.

Riwotzki K. and Haase M.; "Colloidal $YVO_4$:Eu and $YP_{0.95}V_{0.05}O_4$:Eu Nanoparticles: Luminescence and Energy Transfer Processes"; *J. Phys. Chem. B 105* (2001); pp. 12709-12713.

Schuetz, P. & Caruso, F.; "Electrostatically Assembled Fluorescent Thin Films of Rare-Earth-Doped Lanthanum Phosphate Nanoparticles"; *Chemistry of Materials 14*; (2002); pp. 4509-4516.

Seabrook Shane A., et al; "Photo-initiated polymerization of acrylamide in water"; *Polymer 48*; (2007); pp. 4733-4741.

Shen Jie, et al; "Luminescent rare earth nanomaterials for bioprobe applications"; *The Royal Society of Chemistry*, No. 42; Nov. 14, 2008; pp. 5661-5808.

Soini E J.; et al; "Lanthanide chelates as new fluorochrome labels for cytochemistry[1]"; Journal of Histochemistry & Cytochemistry,vol. 36, No. 11; (1988); pp. 1449-1451.

Steemers Frank J., et al; "New Sensitizer-Modified Calix[4]arenes Enabling Near-UV Excitation of Complexed Luminescent Lanthanide Ions"; *J. Am. Chem. Soc. 117*; (1995); pp. 9408-9414.

Steemers Frank J., et al; "Water-Soluble Neutral Calix[4]arene-Lanthanide Complexes: Synthesis and Luminescence Properties"; *J. Org. Chem. 62*; (1997); pp. 4229-4235.

Steinkamp Tanja et al; "Detection strategies for bioassays based on luminescent lanthanide complexes and signal amplification"; *Anal Bioanal Chem 380*; (2004); pp. 24-30.

Sukhanova Alyona, et al; "Fluorescent nanocrystal-encoded microbeads for multiplexed cancer imaging and diagnosis"; *Critical Reviews in Oncology/Hematology 68*; (2008); pp. 39-59.

Sun Yajuan, et al; "Optical Spectroscopy and Visible Upconversion Studies of $YVO_4$:$Er^{3+}$Nanocrystals Synthesized by a Hydrothermal Process"; *Chem. Mater. 18*; (2006); pp. 2726-2732.

Takeshita, S. et al.; "Low-temperature wet chemical synthesis and photoluminescence properties of YVO4: $Bi^{3+}$, $Eu^{3+}$nanophosphors"; *Journal of Luminescence 128*; pp. 1515-1522; (2008).

Takeshita Satoru. et al, "Effects of Citrate Additive on Transparency and Photostability Properties of $YVO_4$:$Bi^{3+}$,$Eu^{3+}$Nanophosphor"; Journal of the Electrochemical Society, 157(3); (2010); pp. J74-J80.

Thermo Fisher Scientific, Inc. "Color-Rich™ : Fluoro-Max™ : DyedMicroparticles" Mar. 2008; pp. 1-6.

Vancaeyzeele Cedric, et al; "Lanthanide-Containing Polymer Nanoparticles for Biological Tagging Applications: Nonspecific Endocytosis and Cell Adhesion"; *J. Am. Chem. Soc. 129*; (2007); pp. 13653-13660.

Van Veggel Frank C.J.M., et al; "Lanthanide(III)-doped nanoparticles that emit in the near infrared"; *Proc. of SPIE* vol. 5224; (2003); pp. 164-175.

Wang Lin and Tan Weihong; "Multicolor FRET Silica Nanoparticles by Single Wavelength Excitation"; *American Chemical Society*, vol. 6, No. 1; (2006); pp. 84-88.

Wang Feng and Liu Xiaogang; "Upconversion Multicolor Fine-Tuning: Visible to Near-Infrared Emission from Lanthanide-Doped $NaYF_4$ Nanoparticles"; *J. Am. Chem. Soc.130*; (2008); pp. 5642-5643.

Wang, F. et al.; "Multicolor tuning of (Ln, P)-Doped YVO4 nanoparticles by single-wavelength excitation"; *Angewandte Chemie-International Edition 47*; pp. 906-909; (2008).

(56) References Cited

OTHER PUBLICATIONS

Wang Guofeng, et al; "Enhanced Photoluminescence of Water Soluble $YVO_4:Ln^{3+}$(Ln=Eu, Dy, Sm, and Ce) Nanocrystals by $Ba^2$ Doping"; *J. Phys. Chem. C*, vol. 112, No. 44; (2008); pp. 17042-17045.

Wang F et al.; "Simultaneous phase and size control of upconversion nanocrystals through lanthanide doping"; *Nature* 463; pp. 1061-1065; (2010).

Ward Thomas, et al; "Microfluidic flow focusing: Drop size and scaling in pressure versus flow-rate-driven pumping"; *Electrophoresis 26*; (2005); pp. 3716-3724.

Werts Martinus H.V.; "Making sense of lanthanide luminescence"; *Science Progress* 88(2); (2005), pp. 101-131.

Wu Shiwei, et al; "Non-blinking and photostable upconverted luminescence from single lanthanide-doped nanocrystals" *PNAS* 106'; pp. 10917-10921; (2009).

Xiao, Xudong, et al; "Upconversion from aqueous phase lanthanide chelates"; *Opt Lett. Author manuscript*; available in PMC Sep. 19, 2006; Published in final edited form as: *Opt Lett.* 30(13); Jul. 1, 2005; 1674-1676. pp. 1-8.

Xiao, Xudong, et al; "Cell assay using a two-photon-excited europium chelate"; *Biomedical Optics Express*, vol. 2, No. 8; Aug. 1, 2011; pp. 2255-2264.

Xu, HaiYan, et al.; "Rapid synthesis of size-controllable $YVO_4$ nanoparticles by microwave irradiation"; *Solid State Communications 130*; pp. 465-468; (2004).

Xu Hongxia, et al; "Multiplexed SNP genotyping using the Qbead™ system: a quantum dot-encoded microsphere-based assay"; *Nucleic Acids Research*, vol. 31, No. 8; e43 (2003); pp. 1-10.

Xu Zhenhe,et al; "$Ln^{3+}$(Ln=Eu, Dy, Sm, and Er) Ion-Doped $YVO_4$ Nano/Microcrystals with Multiform Morphologies: Hydrothermal Synthesis, Growing Mechanism, and Luminescent Properties"; *Inorg. Chem. 49* (2010); pp. 6706-6715.

Zeng Jing Hui, et al; "Monodispersed Nanocrystalline Fluoroperovskite Up-Conversion Phosphors"; American Chemical Society, Crystal Growth & Design, vol. 7, No. 12; (2007); pp. 2774-2777.

Zhang, Hongwu et al; "Low temperature synthesis of nanocrystalline $YVO_4$: Eu via polyacrylamide gel method"; *Journal of Solid State Chemistry 177* (2004) pp. 2649-2654.

Zhang Hongwu, et al; "Photoluminescence of $YVO_4$:Tm phosphor prepared by a polymerizable complex method"; *Solid State Communications 132*; (2004); pp. 527-531.

Zhang Fan, et al; "Fluorescence Upconversion Microbarcodes for Multiplexed Biological Detection: Nucleic Acid Encoding"; *Adv. Mater. 23*; (2011); pp. 3775-3779.

Zhang, F. et al. Rare-Earth Upconverting Nanobarcodes for Multiplexed Biological Detection. *Small 7*; (2011); pp. 1972-1976.

Zhang Qingbin, et al; "Multicolor upconverted luminescence-encoded superparticles via controlling self-assembly based on hydrophobic lanthanide-doped $NaYF_4$ nanocrystals\"; *J. Mater. Chem. 21*; (2011); pp. 12132-12138.

\* cited by examiner

Ex (excitation wavelength)
Em (emission wavelength)

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: synthetic amino acid sequence

<400> SEQUENCE: 1

Glu Lys Gln Leu Ile Ser Glu Glu Asp Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 2

Asp Tyr Lys Asp Asp Asp Asp Lys
1               5
```

SPECTRALLY ENCODED MICROBEADS AND METHODS AND DEVICES FOR MAKING AND USING SAME

CROSS-REFERENCE TO RELATED APPLICATIONS

This application is a National Stage of International Application No. PCT/US13/56280, filed Aug. 22, 2013, which application claims the benefit of U.S. Provisional Patent Application No. 61/692,618, filed Aug. 23, 2012, which applications are incorporated herein by reference in their entireties.

STATEMENT REGARDING FEDERALLY SPONSORED RESEARCH

The invention was made with government support under Grant No. DE-AC02-05CH11231 awarded by the U.S. Department of Energy. The government has certain rights in the invention.

INTRODUCTION

Over the past several years, advances in biomedical research technology have driven an unprecedented explosion of genomic and proteomic data, yet the challenge of translating new biomarkers of disease into actionable diagnostics and therapeutics remains daunting. To both validate and deploy the vast numbers of recent discoveries into clinical practice requires new approaches to multiplexing and high-throughput biomarker analysis. Despite intense research, few practically available cost-effective assays for multiplexing exist, and new approaches are needed. Beyond diagnostics, advances in multiplexing may have impact on basic research and development systems, including combinatorial drug discovery.

Multiplexed assays require that individual probes be reliably identified and tracked throughout an experiment. This identification and tracking is often done using planar arrays, where the identity of each probe is encoded by its physical position. An alternative approach uses encoded beads, where each probe is attached to a separate bead that is uniquely identifiable.

Bead-based assays offer faster reaction kinetics, increased assay flexibility, and improved reproducibility and reduced costs due to the ability to attach probes to multiple particles at once. However, technical challenges in bead encoding have limited their practical application to date. Existing encoding methods generally fall into two categories: spatial encoding and spectral encoding. Spatial encoding schemes create graphical patterns or bar codes in the particle material in a variety of ways. However, spatial methods face difficulties in cost-effective fabrication, often require large particles to generate large code sets, and have slower and more challenging code readout than existing spectral methods due to orientation requirements.

Spectral encoding schemes incorporate mixtures of photoluminescent materials such as lanthanides, quantum dots (QDs), or fluorescent dyes that emit light at different wavelengths to generate uniquely identifiable signatures. These schemes allow identification of codes in any orientation and are compatible with conventional bead synthesis procedures and standard detection optics, making them particularly attractive. Despite the promise of spectral encoding schemes, technical challenges have limited their practical code capacity. Organic dyes have broad emission spectra, narrow Stokes shifts, and limited photostability, making it difficult to deconvolve spectral signatures from multiple dyes and reducing the usable lifetime of the codes. Quantum dots offer relatively narrow and tunable excitation spectra, and have therefore been the subject of considerable recent interest for encoding schemes. However, QDs have complicated photophysics and can undergo energy transfer and re-absorption when tightly packed together. These effects limit the number of optical codes that can be created, due to re-absorption losses at higher concentrations in the beads. As a result, the largest experimentally produced spectral code sets from organic dyes or quantum dots have fallen far short of theoretical expectations. The best known commercial system, Luminex®, has been limited to 500 unique codes and code sets synthesized in the literature have been even smaller.

Accordingly, there exists a need in the art for improved multiplexing and high-throughput biomarker analysis techniques and tools. The present disclosure addresses this need and provides related advantages.

SUMMARY

Spectrally encoded microbeads and methods and devices for making and using spectrally encoded microbeads are provided. The disclosed methods and devices facilitate the preparation and use of microbeads containing multiple lanthanide nanoparticles, which microbeads have uniquely identifiable spectral codes. The disclosed microbeads, and the methods and devices for making and using same, find use in multiplexing and high-throughput biomarker analysis.

The present disclosure provides a population of polymeric microbeads embedded with at least two different lanthanide nanoparticles, the population including: a plurality of polymeric microbeads, wherein each polymeric microbead of the plurality is embedded with at least two lanthanide nanoparticles having different luminescence spectra, and wherein the relative concentrations of the first and second lanthanide nanoparticles are substantially equal among the polymeric microbeads of the population.

In some instances, the luminescence intensity level variation among all the members of the population is no greater than about 15 percent.

Any of the aforementioned populations may have a luminescence intensity level variation among all the members of the population that is no greater than about 5 percent.

Any of the aforementioned populations may have polymeric microbeads, wherein each polymeric microbead of the population has a diameter of less than 500 µm.

Any of the aforementioned populations may have polymeric microbeads, wherein each polymeric microbead of the population has a diameter of less than 100 µm.

Any of the aforementioned populations may have polymeric microbeads, wherein each polymeric microbead of the population has a diameter of less than 50 µm.

Any of the aforementioned populations may have polymeric microbeads, wherein the diameter variation among all the members of the population is no greater than about 5 percent.

Any of the aforementioned populations may have polymeric microbeads, wherein one or more of the lanthanide nanoparticles includes bismuth.

The present disclosure also provides a set of populations of polymeric microbeads embedded with at least two different lanthanide nanoparticles, the set of populations of polymeric microbeads including: a first population of polymeric microbeads, wherein each polymeric microbead of the first population is embedded with at least a first lanthanide nanoparticle and a second lanthanide nanoparticle; wherein the first and second lanthanide nanoparticles comprise different lanthanides; and wherein the relative concentrations of the first and second lanthanide nanoparticles are substantially equal among the polymeric microbeads of the first population; and a second population of polymeric microbeads, wherein each polymeric microbead in the second population is embedded with at least the first lanthanide nanoparticle and the second lanthanide nanoparticle; and wherein the relative concentrations of the first and second lanthanide nanoparticles are substantially equal among the polymeric microbeads of the second population; wherein the concentration of at least one of the first and second lanthanide nanoparticles is different between the polymeric microbeads of the first population and second population.

In some instances, the concentration of one of the first and second lanthanide nanoparticles is substantially equal for each polymeric microbead of the first population and second population of the set of populations.

In some instances, the concentration of the first lanthanide nanoparticle in the first population is a known percentage of the concentration of the first lanthanide nanoparticle in the second population of the set of populations, wherein the known percentage is other than 100 percent.

Any of the aforementioned sets of populations may have polymeric microbeads, wherein the luminescence intensity level variation among all the members of the first population is no greater than about 15 percent.

Any of the aforementioned sets of populations may have polymeric microbeads, wherein the luminescence intensity level variation among all the members of the first population is no greater than about 5 percent.

Any of the aforementioned sets of populations may have polymeric microbeads, wherein the luminescence intensity level variation among all the members of the second population is no greater than about 15 percent.

Any of the aforementioned sets of populations may have polymeric microbeads, wherein the luminescence intensity level variation among all the members of the second population is no greater than about 5 percent.

Any of the aforementioned sets of populations may have polymeric microbeads, wherein each polymeric microbead has a diameter of less than 500 µm.

Any of the aforementioned sets of populations may have polymeric microbeads, wherein each polymeric microbead has a diameter of less than 100 µm.

Any of the aforementioned sets of populations may have polymeric microbeads, wherein each polymeric microbead has a diameter of less than 50 µm.

Any of the aforementioned sets of populations may have polymeric microbeads, wherein the diameter variation among all the members of the set of populations is no greater than about 5 percent.

Any of the aforementioned sets of populations may have polymeric microbeads, wherein each polymeric microbead comprises 3 to 10 lanthanide nanoparticles, wherein each lanthanide nanoparticle has a different luminescence spectra.

Any of the aforementioned sets of populations may have polymeric microbeads, wherein each polymeric microbead comprises an upconverting lanthanide nanoparticle.

Any of the aforementioned sets of populations may have polymeric microbeads, wherein each polymeric microbead comprises a downconverting lanthanide nanoparticle.

Any of the aforementioned sets of populations may include 24 or more different populations of polymeric microbeads.

Any of the aforementioned sets of populations may include 64 or more different populations of polymeric microbeads.

Any of the aforementioned sets of populations may have polymeric microbeads, wherein the lanthanide nanoparticles comprise bismuth.

The present disclosure also provides a set of populations of polymeric microbeads embedded with at least two different lanthanide nanoparticles, the set of populations of polymeric microbeads being produced using a method including: mixing at least two fluids into a first solution, wherein each fluid includes a polymerizable component and a lanthanide nanoparticle having a different luminescence spectra; forming a first plurality of droplets from the first solution; subjecting the first plurality of droplets to polymerization conditions, thereby producing a first population of polymeric microbeads embedded with at least two different lanthanide nanoparticles; mixing the at least two fluids into a second solution, wherein the concentration of at least one of the different lanthanide nanoparticles is different between the first solution and the second solution; forming a second plurality of droplets from the second solution; and subjecting the second plurality of droplets to polymerization conditions, thereby producing a second population of polymeric microbeads embedded with the at least two different lanthanide nanoparticles, wherein the concentration of at least one of the at least two different lanthanide nanoparticles is different between the polymeric microbeads of the first population and the polymeric microbeads of the second population.

In some instances, the concentration of one of the first and second lanthanide nanoparticles is substantially equal for each polymeric microbead of the first population and second population of the set of populations.

In some instances, the concentration of the first lanthanide nanoparticle in the first population is a known percentage of the concentration of the first lanthanide nanoparticle in the second population of the set of populations, wherein the known percentage is other than 100 percent.

The present disclosure also provides a microfluidic device, the device including: a flow channel having an inlet side and an outlet side; at least two inlets positioned toward the inlet side of the flow channel, wherein the inlets are configured to fluidly communicate with the flow channel; a mixing element positioned in the flow channel downstream of the at least two inlets; an input configured to hold a carrier fluid and fluidly communicate with the flow channel, wherein the input configured to hold a carrier fluid is configured to fluidly communicate with a portion of the flow channel downstream of the mixing element; and an outlet located at the outlet side of the flow channel, wherein the outlet is configured to fluidly communicate with the flow channel and is positioned downstream of the portion of the flow channel with which the input configured to hold a carrier fluid is configured to fluidly communicate.

In some instances, the microfluidic device includes a sample collection element in fluid communication with the outlet, and located downstream of the outlet.

Any of the aforementioned microfluidic devices may include a plurality of valves, including valves separating each of the at least two inlets from the flow channel respectively.

Any of the aforementioned microfluidic devices may include a valve between the mixing element and the portion of the flow channel with which the input configured to hold a carrier fluid is configured to fluidly communicate, wherein the valve between the mixing element and the portion of the flow channel with which the input configured to hold a carrier fluid is configured to fluidly communicate, when closed, prevents fluid contained in the mixing element from contacting fluid from the input configured to hold a hydrophobic carrier fluid. In some instances, such microfluidic devices may include a waste outlet located between the mixing element and the valve between the mixing element and the portion of the flow channel with which the input configured to hold a carrier fluid is configured to fluidly communicate. In some instances, one or more of the plurality of valves is configured to be actuated pneumatically.

For any of the aforementioned microfluidic devices, the carrier fluid may be a hydrophilic carrier fluid or a hydrophobic carrier fluid. Where the carrier fluid is a hydrophilic carrier fluid, the microfluidic devices may also include an input which is configured to hold a hydrophobic carrier fluid and fluidly communicate with the flow channel and is located upstream of the mixing element. Where the carrier fluid is a hydrophilic carrier fluid, the input configured to hold a hydrophilic carrier fluid may include an on-chip resistor. Where the carrier fluid is a hydrophilic carrier fluid, the input configured to hold a hydrophobic carrier fluid may include an on-chip resistor. One or more of the above features may be combined in a single microfluidic device.

Where the carrier fluid is a hydrophobic carrier fluid, the microfluidic device may also include an input which is configured to hold a hydrophilic carrier fluid and fluidly communicate with the flow channel and is located upstream of the mixing element. Where the carrier fluid is a hydrophobic carrier fluid, the input configured to hold a hydrophilic carrier fluid may include an on-chip resistor. Where the carrier fluid is a hydrophobic carrier fluid, the input configured to hold a hydrophobic carrier fluid may include an on-chip resistor. One or more of the above features may be combined in a single microfluidic device.

For any of the aforementioned microfluidic devices the mixing element may include a staggered herringbone mixer.

Any of the aforementioned microfluidic devices may be fabricated by multi-layer soft lithography.

Any of the aforementioned microfluidic devices may be fully automated.

The present disclosure also provides a system including any of the aforementioned microfluidic devices, and a chamber, wherein the device is positioned in the chamber and exposed to nitrogen gas therein.

The present disclosure also provides a system including any of the aforementioned microfluidic devices, and a UV generating element positioned to expose a portion of the flow channel to UV radiation, wherein the portion to be exposed to UV radiation is downstream of the portion of the flow channel with which the input configured to hold a carrier fluid is configured to fluidly communicate and upstream of the outlet.

The present disclosure also provides a system including any of the aforementioned microfluidic devices, and a plurality of inlet containers, wherein each inlet container is configured to fluidly communicate to a different one of the at least two inlets, and wherein each inlet container comprises a fluid comprising a different lanthanide nanoparticle and a polymerizable component. In some instances, the system includes a plurality of pumps, wherein the plurality of inlet containers is configured to fluidly communicate with the plurality of pumps. In some instances, the inlet containers include capillary tubing having a length that is at least 1000 times greater than the internal diameter of the capillary tubing. In some instances, the containers are positioned in a chamber and exposed to nitrogen gas therein. In some instances, the plurality of containers includes 2 to 10 lanthanide nanoparticles, wherein each lanthanide nanoparticle has a different luminescence spectra. In some instances, the lanthanide nanoparticle contained in each fluid is present at a concentration of 1 mg/mL to 250 mg/mL. One or more of the above features may be combined in a single system.

The present disclosure also provides a microfluidic device, the device including: a flow channel having an inlet side and an outlet side, wherein a portion of the flow channel is configured as a zig-zag mixer; at least two inlets positioned toward the inlet side of the flow channel, wherein the at least two inlets are configured to fluidly communicate with the flow channel; an input configured to hold a carrier fluid configured to fluidly communicate with the flow channel, wherein the input configured to hold a carrier fluid is configured to fluidly communicate with a portion of the flow channel downstream of the at least two inlets and upstream of the portion of the flow channel configured as a zig-zag mixture; and an outlet located at the outlet side of the flow channel, downstream of the portion of the flow channel configured as a zig-zag mixer. In some instances, the carrier fluid is a hydrophobic carrier fluid. In other cases, the carrier fluid is a hydrophilic carrier fluid.

The present disclosure also provides a method for producing a polymeric microbead comprising at least two different lanthanide nanoparticles, the method including: mixing at least two fluids into a solution, wherein each fluid comprises a polymerizable component and a different lanthanide nanoparticle; forming a droplet from the solution; and subjecting the droplet to polymerization conditions, thereby producing a polymeric microbead comprising at least two different lanthanide nanoparticles, wherein the above steps are performed on any of the aforementioned microfluidic devices or with any of the aforementioned systems. In some instances the polymerization conditions include exposing the droplet to UV radiation. In some instances, the polymerization conditions include exposing the droplet to a temperature sufficient to initiate polymerization of the polymerizable component.

For any of the aforementioned methods, each fluid may have an approximately equivalent total concentration of lanthanide nanoparticles.

For any of the aforementioned methods, the relative concentration of each different lanthanide nanoparticle in the polymeric microbead may be controlled by adjusting the relative flow rates of the at least two fluids. The relative flow rates may be determined based at least in part upon solving the coupled flow equations:

$$Q_n = \frac{P_n - P_{mix}}{R_n}, \text{ and} \qquad \text{Eqn. 1}$$

$$Q_{tot} = \frac{P_{mix}}{R_{mix}}, \qquad \text{Eqn. 2}$$

where
$Q_n$ is the flow rate for each input;
$P_n$ is the pressure for each input;
$Q_{tot}$ is total flow rate;
$P_{mix}$ is the pressure at the point where the fluids are mixed;
$R_{mix}$ is the resistance at the point where the fluids are mixed; and
$R_n$ is the resistance of each input.

For any of the aforementioned methods, the droplet size may be modulated by adjusting the pressure at a T-junction used to form the droplet.

The present disclosure also provides a method for producing a population of polymeric microbeads including a plurality of different lanthanide nanoparticles, the method including: mixing at least two fluids into a solution, wherein each fluid comprises a polymerizable component and a different lanthanide nanoparticle; forming a first plurality of droplets from the solution; and subjecting the first plurality of droplets to polymerization conditions, thereby producing a first plurality of polymeric microbeads embedded with at least two different lanthanide nanoparticles, wherein the relative concentrations of the lanthanide nanoparticles are substantially equal among the polymeric microbeads of the first plurality of polymeric microbeads. In some instances, the method includes mixing the at least two fluids into a second solution, wherein the concentration of at least one of the different lanthanide nanoparticles in the second solution is different than in (i); forming a second plurality of droplets from the second solution; and subjecting the second plurality of droplets to polymerization conditions, thereby producing a second plurality of polymeric microbeads embedded with at least two different lanthanide nanoparticles, wherein the relative concentrations of the lanthanide nanoparticles are substantially equal among the polymeric microbeads of the second plurality of polymeric microbeads. In some instances, the concentration of at least one of the different lanthanide nanoparticles in the second solution is substantially equal to that in (i). In some instances, the concentration of one of the different lanthanide nanoparticles in the first plurality of polymeric microbeads is a known percentage of the concentration of the first lanthanide nanoparticle in the second plurality of polymeric microbeads, wherein the known percentage is other than 100 percent. In some instances, the polymerization conditions include exposing the first plurality of droplets to UV radiation. In some instances, the polymerization conditions include exposing the second plurality of droplets to UV radiation. In some instances, the polymerization conditions include exposing the first plurality of droplets to a temperature sufficient to initiate polymerization of the polymerizable component. In some instances, the polymerization conditions comprise exposing the second plurality of droplets to a temperature sufficient to initiate polymerization of the polymerizable component.

Any of the aforementioned methods for producing a population of polymeric microbeads may produce a population of polymeric microbeads such that the luminescence intensity level variation among all the members of the first plurality of polymeric microbeads is no greater than about 15 percent.

Any of the aforementioned methods for producing a population of polymeric microbeads may produce a population of polymeric microbeads such that the luminescence intensity level variation among all the members of the first plurality of polymeric microbeads is no greater than about 5 percent.

Any of the aforementioned methods for producing a population of polymeric microbeads may produce a population of polymeric microbeads such that the luminescence intensity level variation among all the members of the second plurality of polymeric microbeads is no greater than about 15 percent.

Any of the aforementioned methods for producing a population of polymeric microbeads may produce a population of polymeric microbeads such that the luminescence intensity level variation among all the members of the second plurality of polymeric microbeads is no greater than about 5 percent.

The present disclosure also provides a method of imaging spectrally encoded microbeads, the method including: illuminating one or more microbeads selected from any of the aforementioned populations of microbeads with a light source; detecting luminescence emission from the microbead in a plurality of spectral bands; and determining the intensities of each different lanthanide nanoparticle present in the microbead using linear unmixing. In some instances, the spectral bands are defined by a plurality of emission filters that pass the characteristic emission peaks of each lanthanide nanoparticle. In some instances, the light source is a deep UV light source. In some instances, the light source is near IR light source.

The present disclosure also provides a system, including: a microfluidic device including one or more inlet ports; a flow channel configured for fluid communication with the one or more inlet ports, wherein the flow channel is sized and shaped to provide a monolayer of polymeric microbeads in the flow channel; a sieve valve positioned in or downstream of the flow channel, wherein the sieve valve is configured to allow fluid flow through the flow channel while retaining the polymeric microbeads in the flow channel; and one or more outlet ports configured for fluid communication with the flow channel; and a light source configured to illuminate a portion of the flow channel. In some instances, the light source is a deep UV light source. In some instances, the light source is a near IR light source. Any of the above systems may include a camera configured to collect an image of the illuminated portion of the flow channel. Any of the above systems may include a display configured to display an image of the illuminated portion of the flow channel.

BRIEF DESCRIPTION OF THE DRAWINGS

FIG. 1 also provides a histogram (Panel B) showing particle size distribution for nanoparticles (as measured by dynamic light scattering), and a photograph of vials of nanoparticle suspensions illuminated with a UV lamp (inset).

FIG. 13 provides a table showing the results of liquid chromatography-mass spectrometry/mass spectrometry (LC-MS/MS) analysis of peptides cleaved from spectrally encoded microbeads.

DEFINITIONS

Figure 1:
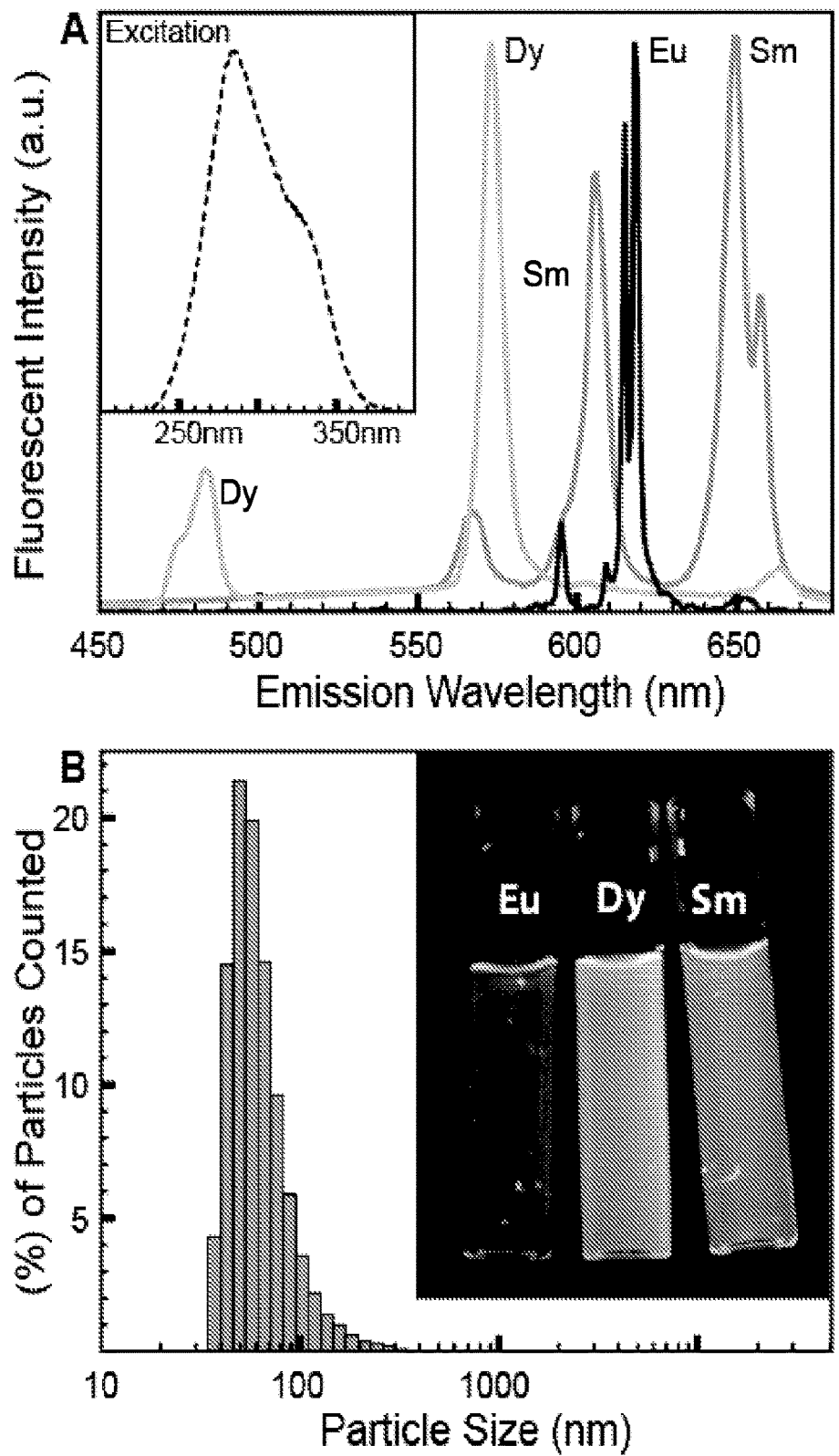
FIG. 1 provides an emission spectra (Panel A) for each of nanoparticles (Dy-, Eu-, and Sm-doped $Y_{0.80}B_{0.15}VO_4$) when excited at 285 nm Excitation spectra of all three nanoparticles (inset) are nearly identical.

As used herein, the term "lanthanide nanoparticle" refers to a nanoparticle which includes a lanthanide and a host lattice.

As used herein, the term "lanthanide" refers to Ce, Pr, Nd, Sm, Eu, Gd, Tb, Dy, Ho, Er, Tm, Yb, La, combinations thereof, compounds containing Ce, Pr, Nd, Sm, Eu, Gd, Tb, Dy, Ho, Er, Tm, Yb, La and combinations thereof, and ions of Ce, Pr, Nd, Sm, Eu, Gd, Tb, Dy, Ho, Er, Tm, Yb, La and combinations thereof.

As used herein, the term "nanoparticle" refers to a particle having one or more dimensions (e.g., diameter) of less than 1000 nm, e.g., about 500 nm or less, about 100 nm or less, about 50 nm or less, about 10 nm or less, about 5 nm or less, or about 1 nm or less. For example, a nanoparticle may have one or more dimensions (e.g., diameter) of from less than 1000 nm to about 500 nm, from about 500 nm to about 100 nm, from about 100 nm to about 10 nm, from about 50 nm to about 10 nm, from about 10 nm to about 5 nm, or from about 5 nm to about 1 nm Nanoparticles may have a generally spherical shape or a non-spherical shape.

As used herein, the term "microbead" refers to a particle having one or more dimensions (e.g., diameter) of about 1000 μm or less, e.g., about 500 μm or less, about 100 μm or less, about 50 μm or less, about 10 μm or less, or about 5 μm or less. For example, a microbead may have one or more dimensions (e.g., diameter) of from about 1000 μm to about 1 μm, from about 500 μm to about 1 μm, from about 100 μm to about 1 μm, from about 50 μm to about 1 μm, from about 10 μm to about 1 μm, or from about 5 μm to about 1 μm. Microbeads may have a generally spherical shape or a non-spherical shape.

It will be appreciated that throughout this present disclosure reference is made to amino acids according to the single letter or three letter code. For the reader's convenience, the single and three letter amino acid code is provided below:

| G | Glycine | Gly | P | Proline | Pro |
|---|---|---|---|---|---|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

Reference to "peptide" herein is meant to encompass a polymer of amino acids linked by native amide bonds and/or non-native amide bonds.

It should be understood that as used throughout, and unless specifically indicated otherwise, the term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring nonproteogenic amino acids such as norleucine, p-alanine, ornithine, etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range.

Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a lanthanide nanoparticle" includes a plurality of such lanthanide nanoparticles and reference to "the microbead" includes reference to one or more microbeads and equivalents thereof known to those skilled in the art, and so forth.

It is further noted that the claims may be drafted to exclude any recited element. As such, this statement is intended to serve as antecedent basis for use of such exclusive terminology as "solely," "only" and the like in connection with the recitation of claim elements, or use of a "negative" limitation.

To the extent any definition of a term defined herein conflicts with a definition of a term in an application or reference incorporated by reference herein, the instant application shall control.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

The present disclosure provides spectrally encoded microbeads and methods and devices for making and using spectrally encoded microbeads. The disclosed methods and devices facilitate the preparation and use of microbeads containing multiple lanthanide nanoparticles, which microbeads have uniquely identifiable spectral codes. The disclosed microbeads, and the methods and devices for making and using same, find use in multiplexing and high-throughput biomarker analysis.

Lanthanide Nanoparticles for Use in Spectrally Encoded Microbeads

The spectrally encoded microbeads of the present disclosure generally include two or more different lanthanide nanoparticles. Suitable lanthanide nanoparticles for incorporation into the spectrally encoded microbeads include nanoparticles including a lanthanide and a host lattice.

Lanthanides which may be incorporated into the disclosed lanthanide nanoparticles include, for example, Ce, Pr, Nd, Sm, Eu, Gd, Tb, Dy, Ho, Er, Tm, Yb, La, combinations thereof, compounds containing Ce, Pr, Nd, Sm, Eu, Gd, Tb, Dy, Ho, Er, Tm, Yb, La and combinations thereof, and ions of Ce, Pr, Nd, Sm, Eu, Gd, Tb, Dy, Ho, Er, Tm, Yb, La and combinations thereof.

A variety of suitable nano-crystal host lattices which may be utilized in the disclosed lanthanide nanoparticles are known in the art. For example, lanthanide dopants may be incorporated into a host lattice to provide lanthanide-doped yttrium orthovanadate ($YVO_4$), lanthanide-doped oxide, lanthanide-doped fluoride, lanthanide-doped chloride, lanthanide-doped bromide, lanthanide-doped iodide, lanthanide-doped lanthanum phosphate, and lanthanide-doped strontium borates (e.g., $SrB_4O_7$, $SrB_6O_{10}$ and $Sr_4B_{14}O_{25}$), among others.

Lanthanide nanoparticles according to the present disclosure may be prepared using methods known in the art or as described herein. An exemplary lanthanide nanoparticle synthesis scheme utilizing yttrium orthovanadate ($YVO_4$) as the host lattice is described in Example 1 below. Additional lanthanide nanoparticle preparation methods and materials are described, for example, in Xu et al. (2004) *Solid State Communications,* 130:465-468; Choi et al. (2010) *Journal of Luminescence,* 130:549-553; and Wang et al. (2008) *Angewandte Chemie—International Edition,* 47:906-909; the disclosure of each of which is incorporated by reference herein.

Lanthanide nanoparticles according to the present disclosure may be configured as up-converting or down-converting lanthanide nanoparticles using methods known in the art. Suitable up-converting lanthanide nanoparticles may include, for example, $NaGdF_4$: Tm; $NaGdF_4$: Ln; $NaGdF_4Yb$; $NaGdF_4Er$; $NaGdF_4Yb$, Er; $NaYF_4$:Er; $NaYF_4$:Yb; $NaYF_4$:Er,Yb; $NaYF_4$:Tm,Yb; $LaF_3$:Yb,Tm; $LaF_3$:Yb, Er; and $LaF_3$:Yb,Ho nanoparticles. Suitable down-converting lanthanide nanoparticles may include, for example, $YVO_4$:Eu; $YVO_4$:Dy; and $YVO_4$:Sm nanoparticles. It should be noted that the above referenced lanthanides may be incorporated into the nanoparticles as their respective ions.

Materials may be added during preparation of the lanthanide nanoparticles to increase their UV absorption. For example, in some embodiments bismuth is incorporated into the lanthanide nanoparticles to increase their UV absorption.

In some embodiments, lanthanide nanoparticles as disclosed herein may be modified (e.g., covered or coated) in a suitable material to facilitate formation of a stable colloid suspension of the lanthanide nanoparticles in a carrier fluid. Suitable materials may include materials which prevent aggregation of the lanthanide nanoparticles in the carrier fluid (e.g., $H_2O$) and/or facilitate maintenance of a nanoparticle form of the lanthanide nanoparticles. For example, suitable materials which may be used to cover or coat the lanthanide nanoparticles may include polyethyleneimine (PEI), polyacrylic acid (PAA), sodium citrate, or citric acid. Polyethyleneimine (PEI) may be suitable for use, e.g., as a coating material in order to make the nanophosphors more compatible with a monomer mixture bearing free amines.

The lanthanide nanoparticles described herein may be incorporated into microbeads, e.g., polymeric microbeads, to provide spectrally encoded microbeads as discussed in greater detail below.

Spectrally Encoded Microbeads

The spectrally encoded microbeads of the present disclosure generally include two or more different lanthanide nanoparticles as discussed herein and one or more polymers, copolymers or combinations thereof.

A variety of polymers may be utilized in the lanthanide nanoparticles described herein. Suitable polymers may be selected which can evenly and irreversibly entrap the lanthanide nanoparticle materials within a polymer matrix. Suitable polymers may include, for example, poly(ethylene glycol) (PEG), polystyrene, polyethylene, poly acrylic acid, poly(methyl methacrylate) (PMMA), polysaccharides, and copolymers or combinations thereof.

In some embodiments, suitable polymers are those which are capable of forming microbeads as a result of a polymerization process, e.g., a thermal- or photo-initiated polymerization process. Such polymers may include, for example, polyacrylate (e.g., poly (PEG-diacrylate)), polyacrylamide (e.g., PEG-diacrylamide), polymethacrylate, polymethacrylamide, polystyrene, polythiol-ene, polyurethane, epoxy resin, polysaccharide (e.g., agarose), as well as copolymers or combinations of two or more of the above. Suitable polymers may also include polyurethanes/polyureas, polysiloxanes, organosiloxanes, polyethers (e.g., polyethylene glycol (PEG)), polyvinylpyrrolidones (PVP), vinyl ethers, vinyl acetates, polyimides, polysulfones, polyamic acids, polyamides, polycarbonates, polyesters, and copolymers or combinations of two or more of the above.

It should be noted that the above polymers may be provided in monomer form during the microbead preparation process, and these monomers may be polymerized to form the above polymers, copolymers or combinations thereof in the spectrally encoded microbeads of the present disclosure. Suitable monomers may include those which can be polymerized in situ alone or with a cross-linking agent to form a cross-linked resin. Additional monomers which may be utilized in the lanthanide nanoparticles described herein may include, e.g., monomers which are capable of participating in thiol-ene thiol-yne reactions, e.g., pentaerythritol tetrakis(3-mercaptopropionate) (TT); diallyl phthalate (DAP); 1,3,5,-triallyl-1,3,5-triazine-2,4,6(1H,3H,5H)-trione (TTT); 1,7-octadiyne (OY); mercaptoacetic acid (MA); allylamine (AA), pentaerythritol triallyl ether (PTE) and propargylamine (PA). These monomers find use, for example, in photo-initiated polymerization processes. For additional discussion of thiol-ene thiol-yne reactions and monomers suitable for use therein, see, e.g., Prasath et al. (2010) *Polym. Chem.*, 1: 685-692, the disclosure of which is incorporated by reference herein.

In some embodiments, a suitable monomer for use in preparation of the disclosed microbeads is selected from a PEG diacrylamide (PEG-DAM), a PEG monoacrylamide-monoamine (PEG-AM) and a PEG-monoacrylamide-monoBoc. A PEG-monoacrylamide-monoBoc may find particular use when the microbead is to be used as a substrate in a downstream peptide synthesis reaction.

In some embodiments, the present disclosure is directed to specific populations of spectrally encoded microbeads, for example, a population of polymeric microbeads embedded with at least two different lanthanide nanoparticles, wherein the population includes a plurality of polymeric microbeads, wherein each polymeric microbead of the plurality is embedded with at least two lanthanide nanoparticles having different luminescence spectra, and wherein the relative concentrations of the first and second lanthanide nanoparticles are substantially equal (e.g., not significantly different) among the polymeric microbeads of the population.

In some embodiments, a set of populations of polymeric microbeads embedded with at least two different lanthanide nanoparticles is provided, the set of populations of polymeric microbeads including a first population of polymeric microbeads, wherein each polymeric microbead of the first population is embedded with at least a first lanthanide nanoparticle and a second lanthanide nanoparticle; wherein the first and second lanthanide nanoparticles comprise different lanthanides; and wherein the relative concentrations of the first and second lanthanide nanoparticles are substantially equal (e.g., not significantly different) among the polymeric microbeads of the first population; and a second population of polymeric microbeads, wherein each polymeric microbead in the second population is embedded with at least the first lanthanide nanoparticle and the second lanthanide nanoparticle; and wherein the relative concentrations of the first and second lanthanide nanoparticles are substantially equal (e.g., not significantly different) among the polymeric microbeads of the second population; wherein the concentration of at least one of the first and second lanthanide nanoparticles is different between the polymeric microbeads of the first population and second population.

In some embodiments, the concentration of the first lanthanide nanoparticle is substantially equal (e.g., not significantly different) for each polymeric microbead of the first population and second population. By providing a set of populations of polymeric microbeads wherein the concentration of a first lanthanide nanoparticle is substantially equal (e.g., not significantly different) for each polymeric microbead of the first population and second population, an internal lanthanide nanoparticle standard may be provided. It should be noted that an internal lanthanide nanoparticle standard may be provided wherein the concentration of the lanthanide nanoparticle standard is not substantially equal across all populations of the set. For example, a lanthanide nanoparticle standard could have a concentration of approximately X for each member of a first population in a set and a concentration of approximately Y for each member of a second population in the set, wherein Y is a known percentage of X other than 100 percent, e.g., 10 percent, 50 percent, 150 percent or 200 percent.

The devices and methods disclosed herein allow for the precise control of the concentration of the lanthanide nanoparticles in the spectrally encoded polymeric microbeads of the present disclosure. Accordingly, a population of polymeric microbeads may be provided such that the relative concentrations of at least two different lanthanide nanoparticles are substantially equal (e.g., not significantly different) among the polymeric microbeads of the population. In other words, the population of polymeric microbeads may be provided such that each polymeric microbead in the population has at least substantially the same ratio of two or more lanthanide nanoparticles as the other polymeric microbeads in the population.

This precision allows a population of spectrally encoded microbeads to be provided such that the luminescence intensity level variation among all the members of the population is no greater than about 25 percent, e.g., no greater than about 20 percent, no greater than about 15 percent, no greater than about 10 percent, no greater than about 5 percent, no greater than about 4 percent, no greater than about 3 percent, no greater than about 2 percent, or no greater than about 1 percent. In some embodiments, the luminescence intensity level variation among all the members of the population is from about 25 percent to about 1 percent, e.g., from about 20 percent to about 1 percent, from about 15 percent to about 1 percent, from about 10 percent to about 1 percent, from about 5 percent to about 1 percent, from about 4 percent to about 1 percent, from about 3 percent to about 1 percent, or from about 2 percent to about 1 percent.

By precisely providing unique, identifiable spectral codes using multiple lanthanide nanoparticles a number of uniquely identifiable polymeric microbead populations may be provided. In some embodiments, a set of populations of polymeric microbeads as described herein includes 2 or more different populations of polymeric microbeads, e.g., 5 or more, 10 or more, 20 or more, 30 or more, 40 or more, 50 or more, 60 or more, 70 or more, 80 or more, 90 or more, or 100 or more different populations of polymeric microbeads, wherein the polymeric microbeads for each population include a different spectral code when compared with the polymeric microbeads of the other populations in the set. In some embodiments, a set of populations of polymeric microbeads as described herein includes $10^2$ or more, $10^3$ or more, $10^4$ or more, $10^5$ or more, $10^6$ or more, or $10^7$ or more different populations of polymeric microbeads, wherein the polymeric microbeads for each population include a different spectral code when compared with the polymeric microbeads of the other populations in the set. For example, in some embodiments, a set of populations of polymeric microbeads as described herein includes from about 2 to about 10, from about 10 to about 20, from about 20 to about 30, from about 30 to about 40, from about 40 to about 50, from about 50 to about 60, from about 60 to about 70, from about 70 to about 80, from about 80 to about 90, or from about 90 to about 100 different populations of polymeric microbeads, wherein the polymeric microbeads for each population include a different spectral code when compared with the polymeric microbeads of the other populations in the set. As a further example, in some embodiments, a set of populations of polymeric microbeads as described herein includes from about 10 to about $10^7$, from about $10^2$ to about $10^7$, from about $10^3$ to about $10^7$, from about $10^4$ to about $10^7$, from about $10^5$ to about $10^7$, or from about $10^6$ to about $10^7$ different populations of polymeric microbeads, wherein the polymeric microbeads for each population include a different spectral code when compared with the polymeric microbeads of the other populations in the set. The number of different identifiable populations may be calculated by taking the number of resolvable luminescence levels to the power of the number of different lanthanide nanoparticles. For example, using 6 different lanthanide nanoparticles with 10 resolvable levels each, the number of different, uniquely identifiable populations is $10^6$ or 1,000,000. This code space can be increased as discussed in greater detail below, by utilizing both up-converting and down-converting lanthanide nanoparticles.

The polymeric microbead populations described herein may be provided in a variety of population sizes. For example, a polymeric microbead population as described herein may include 5 or more, 10 or more, 100 or more, 500 or more, 1000 or more, 1500 or more or 2000 or more polymeric microbeads. In some embodiments, a polymeric microbead population as described herein includes from about 5 to about 2000, from about 10 to about 2000, from about 100 to about 2000, from about 500 to about 2000, from about 1000 to about 2000 or from about 1500 to about 2000 polymeric microbeads.

The polymeric microbeads disclosed herein may include two or more different lanthanide nanoparticles, e.g., 3 or more, 4 or more, 5 or more, 6 or more, 7 or more, 8 or more, 9 or more, or 10 or more, wherein each lanthanide nanoparticle has a different luminescence spectra. For example, in some embodiments, the polymeric microbeads disclosed herein may include from 2 to 10, from 3 to 10, from 4 to 10, from 5 to 10, from 6 to 10, from 7 to 10, from 8 to 10, or from 9 to 10 lanthanide nanoparticles, wherein each lanthanide nanoparticle has a different luminescence spectra.

The spectrally encoded polymeric microbeads of the present disclosure have one or more dimensions (e.g., diameter) of about 1000 µm or less, e.g., about 500 µm or less, about 100 µm or less, about 50 µm or less, about 10 µm or less, or about 5 µm or less. For example, a spectrally encoded microbead may have one or more dimensions (e.g., diameter) of from about 1000 µm to about 1 µm, from about 500 µm to about 1 µm, from about 100 µm to about 1 µm, from about 50 µm to about 1 µm, from about 10 µm to about 1 µm, or from about 5 µm to about 1 µm. The spectrally encoded polymeric microbeads may have a generally spherical shape or a non-spherical shape.

For populations of spectrally encoded polymeric microbeads, each member of the population may have approximately the same one or more dimensions, e.g., one or more dimensions as listed above. In some embodiments, the members of a population of spectrally encoded polymeric microbeads have a diameter such that the diameter variation among all the members of the population is no greater than about 10 percent, e.g., no greater than about 5 percent, no greater than about 1 percent, no greater than about 0.1 percent, or no greater than about 0.01 percent. In some embodiments, the diameter variation among all the members of the population is from about 10 percent to about 1 percent, e.g., from about 5 percent to about 1 percent, from about 4 percent to about 1 percent, from about 3 percent to about 1 percent, or from about 2 percent to about 1 percent. In some embodiments, the diameter variation among all the members of the population is from about 5 percent to about 0.01 percent, e.g., from about 4 percent to about 0.01 percent, from about 3 percent to about 0.01 percent, from about 2 percent to about 0.01 percent, from about 1 percent to about 0.01 percent, or from about 0.1 percent to about to about 0.01 percent.

Spectrally encoded polymeric microbeads according to the present disclosure may include or be modified to include one or more reactive functional groups for the attachment of a molecule or molecules to the spectrally encoded polymeric microbeads. For example, monomers containing a single acrylate group and a functional group (thiol, amine, hydroxyl, carboxylic acid) can be added before polymerization to yield a microbead with functionality suitable for the attachment of an additional molecule or molecules to the microbeads subsequent to polymerization. An exemplary molecule would be hydroxy-PEG-acrylate. As an additional example, in a thiol-ene polymerization system, such reactive functional groups may be provided when the spectrally encoded polymeric microbeads are formed using functional monomers containing carboxylate (mercaptoacetic acid), hydroxyl (pentaerythritol triallyl ether), or amine (allylamine) moieties. See, e.g., Prasath et al. (2010) *Polym. Chem.*, 1: 685-692, the disclosure of which is incorporated by reference herein. Spectrally encoded polymeric microbeads including one or more reactive functional groups, e.g., carboxyl groups, hydroxyl groups or amine groups, can be used for the attachment of one or more molecules, e.g., nucleic acids, peptides, or subunits thereof, to the spectrally encoded polymeric microbeads described herein.

Methods of Making Spectrally Encoded Microbeads

The present disclosure provides methods for producing spectrally encoded microbeads as described herein. These methods may be conducted using microfluidic devices as described in greater detail below. In some embodiments, a population of polymeric microbeads including two or more different lanthanide nanoparticles is provided. The method may include, for example: (i) mixing at least two fluids into a first solution, wherein each fluid comprises a polymerizable component (e.g., a polymer or monomer) and a different lanthanide nanoparticle; (ii) forming droplets from the solution; and (iii) subjecting the droplets to polymerization conditions, thereby producing a first set of polymeric microbeads embedded with at least two different lanthanide nanoparticles, wherein the relative concentrations of the lanthanide nanoparticles are substantially equal (e.g., not significantly different) among the polymeric microbeads of the first set.

In some embodiments, the method may include the following additional steps (iv) mixing the at least two fluids into a second solution, wherein the concentration of at least one of the different lanthanide nanoparticles in the second solution is different than in (i) above; (v) forming droplets from the solution; and (vi) subjecting the droplets to polymerization conditions, thereby producing a second set of polymeric microbeads embedded with at least two different lanthanide nanoparticles, wherein the relative concentrations of the lanthanide nanoparticles are substantially equal (e.g., not significantly different) among the polymeric microbeads of the second set.

In some embodiments, the concentration of at least one of the different lanthanide nanoparticles in the second solution is substantially equal (e.g., not significantly different) to that in (i) above.

The above mixing steps may be implemented using a variety of "on-chip" and "off-chip" mixing elements as described in greater detail below.

The step of forming droplets from the solution may include, for example, contacting the solution (which may be hydrophilic due to the presence of a hydrophilic carrier fluid, e.g., water) with a hydrophobic carrier fluid (e.g., mineral oil or water-immiscible organic solvent, e.g. octanol) such that droplets are formed. This may be accomplished, for example, by introducing the solution into a flowing stream including the hydrophobic carrier fluid. Alternatively, a hydrophobic carrier fluid (e.g., mineral oil or water-immiscible organic solvent, e.g. octanol) can be used to form the solution, and droplets can be formed by contacting the hydrophobic carrier fluid with a hydrophilic carrier fluid (e.g., water). This may be accomplished, for example, by introducing the hydrophobic carrier fluid into a flowing stream including the hydrophilic carrier fluid.

Any suitable device and/or method for droplet formation may be utilized to form droplets in the context of the present disclosure, including, e.g., the utilization of flow focusing nozzles. See, e.g., Ward et al. (2005) *Electrophoresis*, 26:3716-3724, the disclosure of which is incorporated by reference herein.

The droplet size may be modulated by adjusting the pressure used to form the droplet, e.g., at the interface of the solution and the hydrophobic carrier fluid. In addition, droplet size may be modulated by adjusting the geometry, e.g., size and shape, of the microfluidic device channels.

One or more stabilizers or surfactants may be added to one or more of the carrier fluids to prevent droplet merging and sticking of droplets to the walls of the microfluidic device. Suitable surfactants may include, for example, Abil® EM90 (a silicon based emulsifier; CAS No. 144243-53-8) and Span™ 80 (CAS No. 1338-43-8), among others.

The step of subjecting the droplets to polymerization conditions may include, for example, exposing the droplets to UV radiation or elevated temperatures to initiate polymerization. Other suitable polymerization conditions are known in the art and may be selected provided that they are compatible with the polymers and/or monomer components to be polymerized, e.g., thiol-ene polymerization, redox-initiated polymerization, and controlled radical polymerization by Reversible Addition-Fragmentation chain Transfer (RAFT), Atom Transfer Radical Polymerization (ATRP) or Nitroxide-Mediated Polymerization (NMP). See also, e.g., Piskin E. et al. (1994) *J. of Biomaterials Science—Polymer Edition* 5:451-471; the disclosure of which is incorporated by reference herein.

In some embodiments, droplets are exposed to radiation (e.g., UV radiation) by localizing the radiation (e.g., UV radiation) exposure onto a microfluidic device (as discussed in greater detail below) such that the droplets are only irradiated after they have been formed on the microfluidic device and before they exit the microfluidic device. Radiation (e.g., UV radiation) localization may be achieved using an inverted microscope by mounting the microfluidic device on the microscope stage. For example, UV illumination may occur through the objective onto a very small area and an additional aperture within the microscope UV light path may further restrict the UV irradiation to a specific area of the microfluidic device.

Where a polymerization method is utilized to form the spectrally encoded polymeric microbeads, a suitable polymerization initiator (e.g., a photoinitiator or thermal initiator) may be utilized which is compatible with the polymerizable components and the polymerization conditions. For example, where a UV polymerization process is utilized, a suitable initiator may include a compound that, when exposed to UV light, undergoes a photoreaction, producing reactive species that are capable of initiating polymerization. Exemplary photoinitiators may include, e.g., acetophenones, benzyl and benzoin compounds, benzophenone, cationic photoinitiators, and thioxanthones. In some embodiments, a photoinitiator such as 2-hydroxy-4'-(2-hydroxyethoxy)-2-methylpropiophenone (Irgacure® 2959) is utilized. Suitable thermal initiators may include, for example, azo compounds, peroxides or hydroperoxides, persulfates, and the like.

Methods which do not require polymerization may also be used to form the spectrally encoded polymeric microbeads. For example, a polymer precipitation method may be utilized in which a pre-formed polymer (e.g., a mid- to high-molecular weight polymer) is dissolved in a suitable solvent (e.g., water) along with dispersed lanthanide nanoparticles. Droplets of this solution can be formed by introducing the solution into an immiscible carrier fluid (e.g., a hydrophobic carrier fluid, e.g., mineral oil). The immiscible carrier fluid and polymer should be selected such that the polymer does not dissolve in the immiscible carrier fluid, and the immiscible carrier fluid is capable of accepting the solvent leaching from the droplet as the polymeric microbead is formed through precipitation. Additional solvent-immiscible carrier fluid combinations may include, e.g., dichloromethane as a solvent and poly(vinyl alcohol) (PVA) as an immiscible carrier fluid. Microbead preparation methods utilizing a dichloromethane-poly(vinyl alcohol) (PVA) combination are described, for example, in Berkland et al. (2002) *Journal of Controlled Release*, 73:59-74, and Berkland et al. (2004) *Journal of Controlled Release*, 94:129-141, the disclosure of each of which is incorporated by reference herein.

The steps of mixing at least two fluids can occur either before or after droplet formation depending on the particular microfluidic device architecture utilized. For example, where a herringbone type mixing architecture is utilized the two fluids may be mixed prior to droplet formation. Alternatively, where a zig-zag type mixing architecture is utilized droplets containing unmixed lanthanide nanoparticles may be formed and subsequently mixed to distribute the lanthanide nanoparticles within a droplet.

Accurate programming of spectral codes for the spectrally encoded microbeads may be facilitated by precisely controlling the flow from each of the lanthanide nanoparticle fluid inputs. This may be accomplished, in part, by solving the coupled flow equations (1) and (2) to determine the pressure ($P_n$) from each input (n) to achieve the desired flow rates ($Q_n$):

$$Q_n = \frac{P_n - P_{mix}}{R_n} \quad \text{(Eqn. 1)}$$

$$Q_{tot} = \frac{P_{mix}}{R_{mix}} \quad \text{(Eqn. 2)}$$

where $Q_{tot}$ is the total flow rate from all lanthanide inputs, $P_{mix}$ is the pressure at the inlet to the mixing channel where all lanthanide input streams come together, $R_{mix}$ is the resistance of the mixing channel, and ($R_n$) is the resistance of each input. The methods described herein may be implemented using one or more microfluidic devices as described in greater detail below, alone or in combination with one or more electronic control devices. The methods may be implemented via software stored in a computer readable medium and configured to run on the one or more electronic control devices.

Microfluidic Devices and Systems for Preparing Spectrally Encoded Microbeads

The present disclosure provides microfluidic devices and systems configured for the preparation of spectrally encoded microbeads as described herein. In some embodiments, a microfluidic device according to the present disclosure includes a flow channel having an inlet side and an outlet side; at least two inlets positioned toward the inlet side of the flow channel, wherein the inlets are configured to fluidly communicate with the flow channel; a mixing element positioned in the flow channel downstream of the at least two inlets; an input configured to hold a hydrophobic carrier fluid and fluidly communicate with the flow channel, wherein the input configured to hold a hydrophobic carrier fluid is configured to fluidly communicate with a portion of the flow channel downstream of the mixing element; and an outlet located at the outlet side of the flow channel, wherein the outlet is configured to fluidly communicate with the flow channel and is positioned downstream of the portion of the flow channel with which the input configured to hold a hydrophobic carrier fluid is configured to fluidly communicate. Generally, an input configured to hold a hydrophobic carrier fluid will be made of a material that is compatible with the hydrophobic carrier fluid and which is sized and shaped to hold the hydrophobic carrier fluid.

Figure 2:
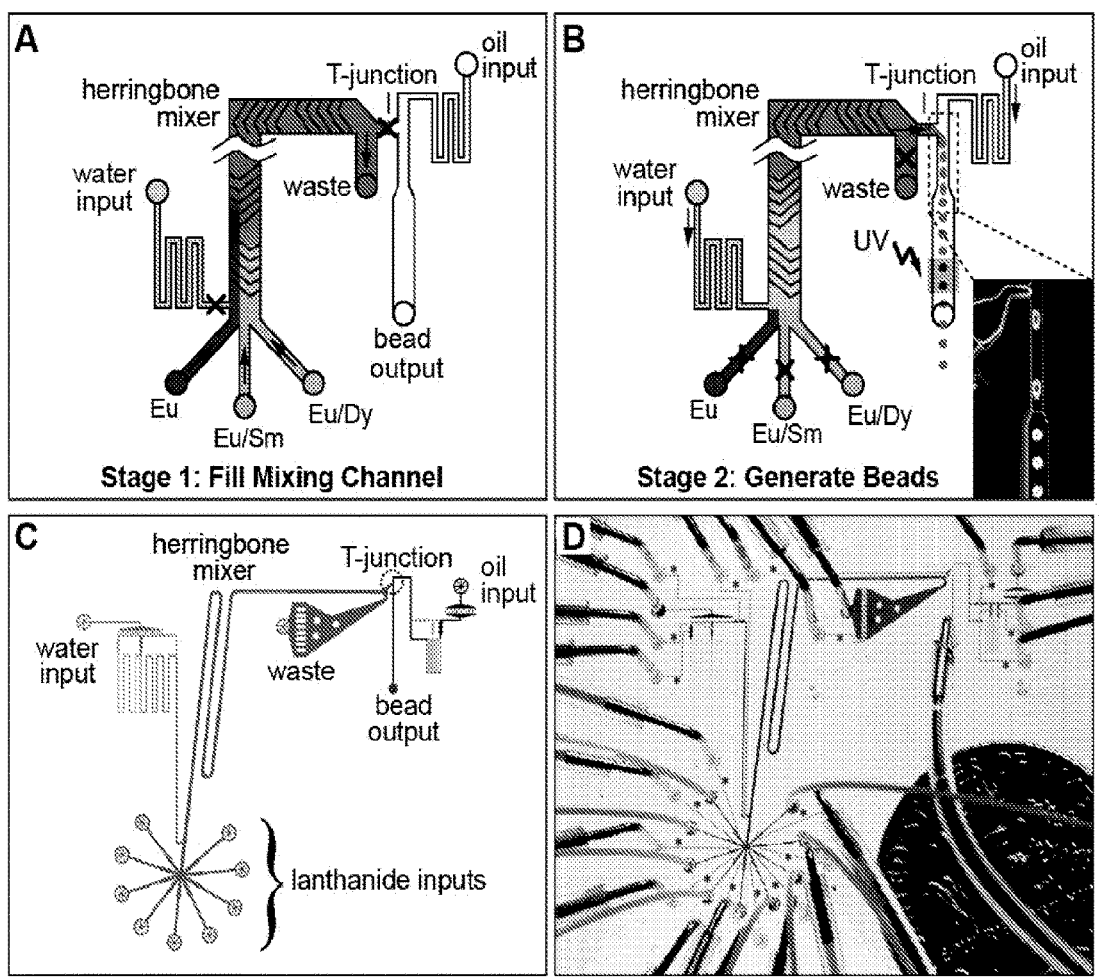
FIG. 2 provides schematics and related images of a microfluidic bead synthesizer according to some embodiments of the present disclosure and a method of using same. (Panel A) Stage 1 of bead synthesis. Mixtures of lanthanide nanoparticles (Eu alone, Eu/Sm, Eu/Dy) suspended in prepolymer bead mixture flow into a microfluidic device at controlled ratios and are mixed on chip using a mixing element (an exemplary staggered herringbone mixer) is depicted. (Panel B) Stage 2 of bead synthesis. A hydrophilic carrier fluid (e.g., water pushes) the lanthanide mixture towards a T-junction containing a continuously flowing hydrophobic carrier fluid (e.g., oil) stream, producing droplets (shown in microscope image, inset). Droplets are polymerized into beads by exposing them to polymerization conditions (e.g., via illumination with UV light) and collected for later use. (Panel C) CAD drawing of the flow channels of the device showing the lanthanide inputs and the exemplary herringbone mixer, an input configured to hold a hydrophilic carrier fluid (an exemplary water input is depicted) and resistor, an input configured to hold a hydrophobic carrier fluid (e.g., an oil input) and bead output. (Panel D) Photograph of the bead synthesizer microfluidic device with food coloring in the channels and a dime for scale. Flow channels are colored as in panel C; control lines used to open and close on-chip valves are identified with "*".

The portion of the flow channel downstream of the mixing element with which the input configured to hold a hydrophobic carrier fluid is configured to fluidly communicate may be configured as a T-junction, e.g., as depicted in FIG. 2.

In other embodiments, a microfluidic device according to the present disclosure includes a flow channel having an inlet side and an outlet side; at least two inlets positioned toward the inlet side of the flow channel, wherein the inlets are configured to fluidly communicate with the flow channel; a mixing element positioned in the flow channel downstream of the at least two inlets; an input configured to hold a hydrophilic carrier fluid and fluidly communicate with the flow channel, wherein the input configured to hold a hydrophilic carrier fluid is configured to fluidly communicate with a portion of the flow channel downstream of the mixing element; and an outlet located at the outlet side of the flow channel, wherein the outlet is configured to fluidly communicate with the flow channel and is positioned downstream of the portion of the flow channel with which the input configured to hold a hydrophilic carrier fluid is configured to fluidly communicate. Generally, an input configured to hold a hydrophilic carrier fluid will be made of a material that is compatible with the hydrophilic carrier fluid and which is sized and shaped to hold the hydrophilic carrier fluid.

The portion of the flow channel downstream of the mixing element with which the input configured to hold a hydrophilic carrier fluid is configured to fluidly communicate may be configured as a T-junction.

It should be noted that while FIG. 2 depicts an embodiment wherein an input configured to hold a hydrophobic carrier fluid is positioned downstream from the inlets, such a depiction is not intended to be limiting and the downstream fluid input may be configured to hold either a hydrophilic carrier fluid or a hydrophobic carrier fluid so as to provide a hydrophilic in hydrophobic droplet (e.g., a water-in-oil droplet) or a hydrophobic in hydrophilic droplet (e.g., an oil-in-water droplet) accordingly.

As discussed previously herein, droplet size may be modulated by adjusting the pressure at the interface (e.g., at a T-junction) of the hydrophilic and hydrophobic carrier fluids. In addition, droplet size may be modulated by adjusting the geometry of the microfluidic device channels.

In other embodiments, a microfluidic device is provided which includes a flow channel having an inlet side and an outlet side, wherein a portion of the flow channel is configured as a zig-zag mixer; at least two inlets positioned toward the inlet side of the flow channel, wherein the at least two inlets are configured to fluidly communicate with the flow channel; an input configured to hold a hydrophobic (or hydrophilic) carrier fluid and fluidly communicate with the flow channel, wherein the input configured to hold a hydrophobic (or hydrophilic) carrier fluid input is configured to fluidly communicate with a portion of the flow channel downstream of the at least two inlets and upstream of the portion of the flow channel configured as a zig-zag mixer; and an outlet located at the outlet side of the flow channel, downstream of the portion of the flow channel configured as a zig-zag mixer.

While the above embodiments are described with respect to "on-chip" mixing elements, i.e., mixing elements incorporated on or in the microfluidic device itself, it should be noted that mixing of the lanthanide nanoparticle inputs can also occur "off-chip", i.e., in a separate device (e.g., a separate microfluidic device). A variety of suitable mixing elements may be utilized as off-chip mixing elements, including, e.g., rotary pump mixers and the like. Once mixed the lanthanide nanoparticle inputs can be returned to a microfluidic device (e.g., via a single input) for droplet formation.

The functions of lanthanide nanoparticle input mixing and droplet formation may also be provided by connecting a plurality of microfluidic devices in series. For example, mixing of lanthanide nanoparticle inputs may occur in a first microfluidic device which is configured to communicate with a second microfluidic device configured to provide droplet formation and microbead synthesis.

In some embodiments, a microfluidic device as described herein includes an input which is located upstream of one or more mixing elements and is configured to hold a hydrophilic (or hydrophobic) carrier fluid (e.g., a water input or an oil input) and fluidly communicate with the flow channel.

The inputs described herein may be configured to include on-chip resistors which facilitate control of the inputs. These on-chip resistors may be optimized, for example, for stable droplet production at the interface between a hydrophilic carrier fluid and a hydrophobic carrier fluid as described herein.

In some embodiments, a microfluidic device as described herein may include one or more valves positioned between a flow channel of the microfluidic device and one or more inlets and/or outlets of the microfluidic device. By opening, closing or modulating these one or more valves, fluid communication between the flow channel and the one or more inlets and/or outlets can be controlled. One or more valves may also be positioned between the flow channel and one or more of the inputs configured to hold a hydrophilic (or hydrophobic) carrier fluid and the input configured to hold a hydrophobic (or hydrophilic) carrier fluid as described herein. One or more of the valves may be configured for actuation via a variety of mechanisms, e.g., mechanical, pneumatic, hydraulic, or a combination thereof. In some embodiments, the opening, closing and/or modulation of the valves is automatically controlled by a suitable electronic control device known in the art, such as a computer.

It should be noted that valveless systems may also be utilized. For example, flow channels may be pressurized to control the flow of the various inputs and outputs without the use of valves.

A microfluidic device as described herein may include a sample collection element in fluid communication with the outlet, and located downstream of the outlet. In some embodiments, a microfluidic device as described includes a waste outlet located between the mixing element and the valve between the mixing element and the portion of the flow channel with which the input configured to hold a hydrophobic (or hydrophilic) carrier fluid is configured to fluidly communicate.

Where the mixing element is positioned in the flow channel it may be selected from a variety of suitable structures designed to cause turbulent flow and/or transverse flow across the flow channel and thereby mix fluid streams originating from the least two inlets positioned toward the inlet side of the flow channel. These structures may be positioned on and/or in one or more walls of the flow channel and in some embodiments may be etched or ablated into one or more walls of the flow channel. Suitable structures may include, for example, wells or trenches formed in one or more walls of the flow channel, or obstructions positioned in the flow channel. In some embodiments, the flow channel is configured to include a herringbone configuration of grooves or channels positioned in the flow channel and configured to mix fluid streams originating from the least two inlets positioned toward the inlet side of the flow channel. In some embodiments, the herringbone structure is a staggered herringbone structure such as that depicted in FIG. 2, Panels A and B. In addition and/or as an alternative to the above passive mixing elements, active mixing may be utilized. Such active mixing elements may be positioned in or external to the flow channel and/or the microfluidic device as appropriate. Exemplary mixing elements are described in Lee et al. (2011) *Int. J. Mol. Sci.* 12:3263-3287, the disclosure of which is incorporated by reference herein.

A microfluidic device according to the present disclosure may be formed using a variety of fabrication methods known in the art, including, e.g., wet etching, reactive ion etching, machining, photolithography, soft lithography (e.g., multi-layer soft lithography), hot embossing, injection molding, laser ablation, in situ construction, and plasma etching. An example of a suitable fabrication method utilizing multi-layer soft lithography is provided in Example 2. Selection of a suitable fabrication method may also depend at least in part on the material substrate to be used in the fabrication.

Substrates which may find use in the fabrication of a microfluidic device according to the present disclosure include, for example, silicon, glass, quartz, polydimethylsiloxane (PDMS), polymethylmethacrylate (PMMA), thermoset polyester (TPE), polycarbonate (PC), cyclic olefin copolymer (COC), polystyrene (PS), polyvinylchloride (PVC), and polyethyleneterephthalate glycol (PETG). See, e.g., Fiorini G. S. and Chiu D. T. (2005) *BioTechniques* 38:429-446, the disclosure of which is incorporated by reference herein.

Operation of a microfluidic device according to the present disclosure may be automated such that operation of the device itself as well as the various input sources and related system components are automatically controlled by a suitable electronic control device known in the art, such as a computer, configured to run a microbead fabrication software program configured to implement the methods described herein.

The microfluidic devices described herein may operate in conjunction with one or more additional components as part of one or more systems. For example, a system according to the present disclosure may include one or more microfluidics devices as described herein and a radiation generating element (e.g., a UV generating element) positioned to expose a portion of the flow channel to radiation (e.g., UV radiation) and thereby facilitate microbead polymerization, wherein the portion to be exposed to radiation is downstream of the portion of the flow channel with which the input configured to hold a hydrophobic (or hydrophilic) carrier fluid is configured to fluidly communicate and upstream of the outlet.

A system according to the present disclosure may also include a plurality of inlet containers, wherein each inlet container is configured to fluidly communicate with a different one of the at least two inlets, and wherein each inlet container includes a fluid including a different lanthanide nanoparticle or lanthanide nanoparticle combination and a polymerizable component (e.g., a polymer or monomer). The inlet containers may include capillary tubing for fluidically communicating between the at least two inlets and the flow channel. In some embodiments, the capillary tubing has a length that is substantially greater than its internal diameter, e.g., a length that is at least 100 times greater, at least 500 times greater, or at least 1000 times greater than the internal diameter of the capillary tubing. A system according to the present disclosure may also include a plurality of pumps wherein the plurality of inlet containers is configured to fluidly communicate with the plurality of pumps.

In some embodiments, one or more microfluidics devices as described herein, including optionally the above inlet containers and/or pumps, are positioned in a chamber which is purged with an inert gas, e.g., nitrogen, for example, to reduce oxygen inhibition of the microbead formation (e.g., polymerization) process.

As discussed above, each inlet container may include a fluid including a different lanthanide nanoparticle or lanthanide nanoparticle combination. In some embodiments, the plurality of containers includes 2 to 10, e.g., 3 to 10, 4 to 10, 5 to 10, 6 to 10, 7 to 10, 8 to 10, or 9 to 10 lanthanide nanoparticles, wherein each lanthanide nanoparticle has a different luminescence spectra.

The lanthanide nanoparticle contained in each fluid may be present at a concentration of from about 1 mg/mL to about 250 mg/mL, e.g., from about 5 mg/mL to about 250 mg/mL, from about 10 mg/mL to about 250 mg/mL, from about 20 mg/mL to about 250 mg/mL, from about 30 mg/mL to about 250 mg/mL, from about 40 mg/mL to about 250 mg/mL, from about 50 mg/mL to about 250 mg/mL, from about 60 mg/mL to about 250 mg/mL, from about 70 mg/mL to about 250 mg/mL, from about 80 mg/mL to about 250 mg/mL, from about 90 mg/mL to about 250 mg/mL, from about 100 mg/mL to about 250 mg/mL, from about 150 mg/mL to about 250 mg/mL, or from about 200 mg/mL to about 250 mg/mL.

Methods and Devices for Imaging Spectrally Encoded Microbeads

Methods and devices for imaging spectrally encoded microbeads are also provided by the present disclosure. Generally, such methods include steps of illuminating a microbead including a plurality of different lanthanide nanoparticles with a suitable source of illumination; detecting luminescence emission from the microbead in a plurality of spectral bands; and determining the intensities of each different lanthanide nanoparticle present in the microbead using linear unmixing. The spectral bands may be defined by a plurality of emission filters that pass the characteristic emission peaks of each lanthanide nanoparticle. In this regard, it should be noted that one or more filters may be configured to pass multiple emission peaks. Linear unmixing generally includes least squares fitting after background subtraction and flat-field correction of the microbead images. Linear unmixing and the associated image analysis are described in greater detail in Example 3.

The source of illumination should be selected such that it is compatible with the particular lanthanide nanoparticles present in the spectrally encoded microbeads. For example a deep ultraviolet (UV) light source may be selected for use with down-converting lanthanide nanoparticles while a near-infrared (IR) light source may be used with up-converting lanthanide nanoparticles.

The methods described herein may be implemented using one or more microfluidic devices as described in greater detail below, alone or in combination with one or more electronic control devices. The methods may be implemented via software stored in a computer readable medium and configured to run on the one or more electronic control devices.

Figure 3:
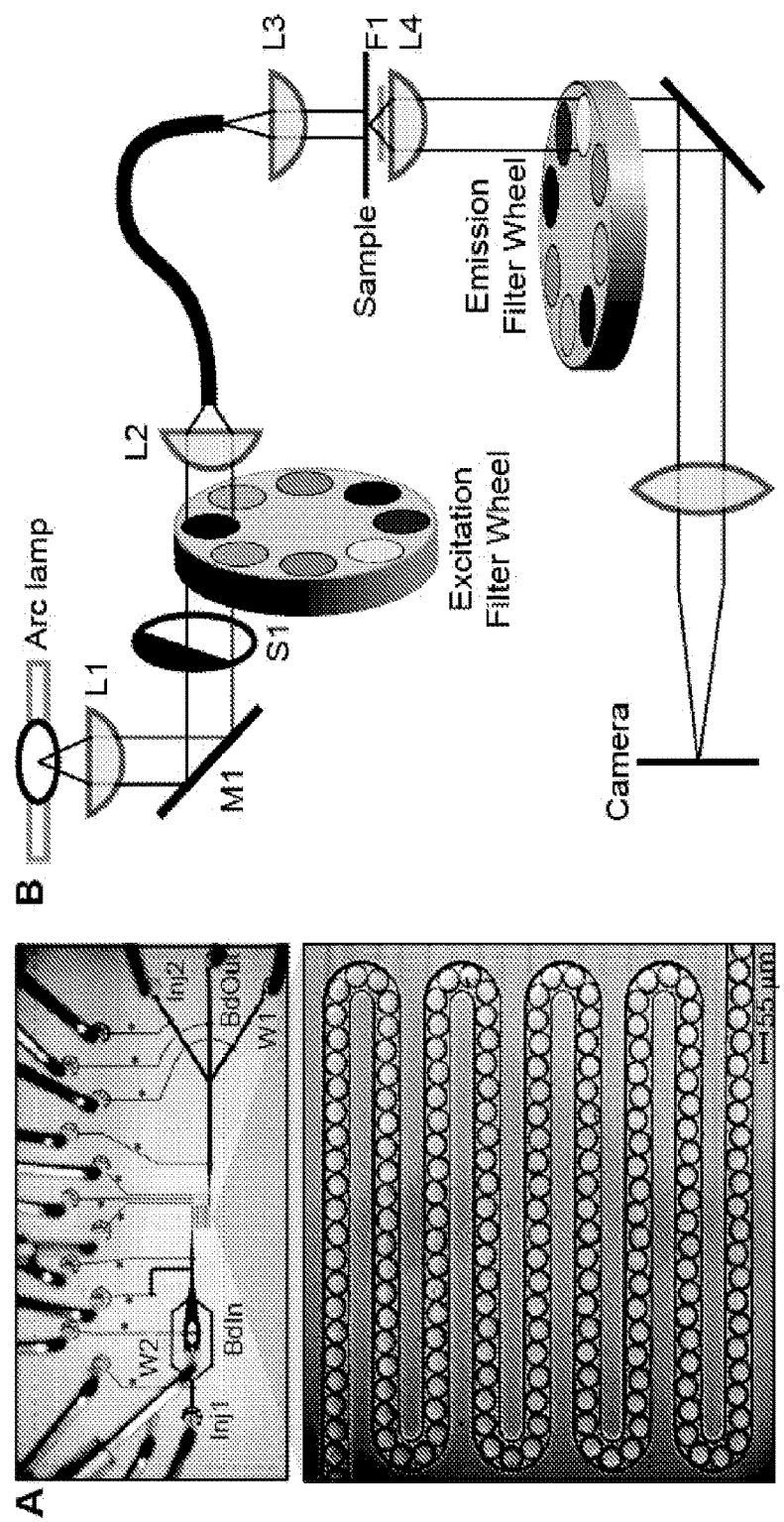
FIG. 3 provides schematics and related images of a bead imaging setup according to some embodiments of the present disclosure. (Panel A) Photograph of microfluidic imaging device with flow channels shown in black and control channels shown in grey (and identified by "*"). Beads are injected into a 55 μm wide serpentine channel for imaging (photograph, inset); sieve valves at the end of the channel retain beads while permitting fluid flow to facilitate channel loading. Inputs (Injection 1 (Inj1), Bead In (BdIn), Injection 2 (Inj2)) and outputs (Waste 1 (W1), Waste 2 (W2), Bead Out (BdOut)) at either end of the device provide bidirectional flow. (Panel B) Schematic of a microscopy system used for imaging beads. Light from a suitable light source (e.g., a full-spectrum 300 W Xenon arc lamp) is collected (L1), reflected off a 400 nm long pass filter (M1) to reject visible light, and passed through a shutter (S1) and an excitation filter wheel (to switch between UV and visible transillumination) before being focused (L2) into a deep UV liquid light guide. The other end of the liquid light guide is mounted on the condenser mount of a Nikon® Ti microscope, where the light is collimated by a fused silica lens (L3) and projected onto the sample. Emitted light from the sample is collected by a Plan Apo 4x/0.2 NA objective (L4), with a UV blocking filter placed between the sample and the objective. Emitted light is filtered through an emission filter wheel mounted beneath the objective before being focused onto the camera.

Suitable microfluidic devices for use in imaging spectrally encoded microbeads include those which are capable of providing a monolayer of spectrally encoded microbeads for image acquisition by a microscope and/or camera. Suitable microfluidic devices may include, for example, one or more inlet ports; a flow channel configured for fluid communication with the one or more inlet ports; a sieve valve positioned in or downstream of the flow channel, wherein the sieve valve is configured to allow fluid flow through the flow channel while retaining the polymeric microbeads in the flow channel; and one or more outlet ports configured for fluid communication with the flow channel. In some embodiments, e.g., as depicted in FIG. 3, a flow channel including a serpentine portion is provided, wherein the serpentine portion is sized and shaped to provide an ordered, linear array of polymeric microbeads.

Generally, the microfluidic devices for use in imaging the spectrally encoded microbeads may be prepared and operated using materials and methods similar to those described above in the context of the microbead preparation devices, provided that they are compatible with the source of illumination selected for use during the imaging process.

A bead imaging system according to the present disclosure may include one or more microfluidic devices as described above and a light source configured to illuminate the monolayer of beads, e.g., in a portion of the flow channel. As discussed above, the source of illumination should be selected such that it is compatible with the particular lanthanide nanoparticles present in the spectrally encoded microbeads. Such a system may also include a camera configured to collect an image of the illuminated portion of the flow channel.

A bead imaging microfluidic device and/or system according to the present disclosure may be automated, and in some embodiments may include a display unit configured to display an image of the spectrally encoded microbeads, e.g., as positioned in the flow channel. The displayed image may include a false color overlay of lanthanide luminescence which is scaled and adjusted for microfluidic device autofluorescence.

Peptide Synthesis Using Spectrally Encoded Microbeads

Peptides may be used for a variety of purposes including, e.g., the preparation of epitope-specific antibodies, mapping of antibody epitopes and enzyme binding sites and the design of novel enzymes, drugs and vaccines. Accordingly, methods which provide for low-cost synthesis relative to commercially available methods and which can be used to synthesize multiple peptides simultaneously are of interest. Methods and devices for the solid-phase synthesis of predetermined peptide sequences which utilize spectrally encoded microbeads as described herein are provided. Generally, the methods include coupling a spectrally encoded microbead, e.g., as described herein, functionalized with one or more functional groups (e.g., peptide-bond forming functional groups, such as amine functional groups), with a first amino acid (e.g., an N-terminal protected amino acid). Additional amino acids can then be added, e.g., using the synthesis scheme described herein, or using standard tert-butoxycarbonyl (Boc) or 9-fluorenylmethoxycarbonyl (Fmoc) synthesis reagents, procedures and reaction times, e.g., as described in Amblard et al., *Mol Biotechnol.* (2006) July 33(3):239-54; Lloyd-Williams P. et al. (1997) *Chemical approaches to the synthesis of peptides and proteins*. Boca Raton: CRC Press. 278; Merrifield R. B. (1963) Solid phase peptide synthesis. I. The synthesis of a tetrapeptide. *Journal of the American Chemical Society.* 85, 2149-54; Carpino L. A. (1957) Oxidative reactions of hydrazines. Iv. Elimination of nitrogen from 1,1-disubstituted-2-arenesulfonhydrazides1-4. *Journal of the American Chemical Society.* 79, 4427-31; McKay F. C. and Albertson N. F. (1957) New amine-masking groups for peptide synthesis. *Journal of the American Chemical Society.* 79, 4686-90; Anderson G. W. and McGregor A. C. (1957) T-butyloxycarbonylamino acids and their use in peptide synthesis. *Journal of the American Chemical Society.* 79, 6180-3; and Carpino L. A. and Han G. Y. (1972) 9-fluorenylmethoxycarbonyl amino-protecting group. *The Journal of Organic Chemistry.* 37, 3404-9; the disclosure of each of which is incorporated by reference herein. In some embodiments, a peptide synthesis scheme according to the present disclosure includes the incorporation of a cleavable linker (e.g., an aspartic acid-proline dipeptide linker) that can be cleaved under orthogonal conditions to peptide synthesis reactions.

In some embodiments of the disclosed methods, one or more of the above steps may be performed in a microfluidic device.

In some embodiments a peptide synthesis method according to the present disclosure includes steps of imaging a plurality of microbeads, identifying a plurality of spectral codes based on the imaging, and sorting one or more of the microbeads based on the identified spectral codes.

While the present disclosure describes microbeads containing multiple lanthanide nanoparticles, which microbeads have uniquely identifiable spectral codes, it should be noted that the devices and methods described herein may also find use in the preparation, analysis, and use of microbeads prepared using other encoding techniques such as the incorporation of quantum dots, organic dyes, and the like. For example, while lanthanide nanoparticle containing microbeads may be preferred for various reasons as discussed herein, the peptide synthesis methods described herein are not limited to the use of such microbeads, and may instead utilize microbeads prepared using other encoding techniques such as the incorporation of quantum dots, organic dyes, and the like.

Single Bead Release for Microfluidic Sorting

In some embodiments of the disclosed methods and devices, it may be advantageous to release microbeads one-at-a-time from a microfluidic channel. For example, in order to automate the sorting of beads for programmable peptide synthesis, it may be advantageous to image arrays of beads and then release the beads one-at-a-time for downstream sorting. To achieve this type of release from a microfluidic channel, the microfluidic channel may be sized and shaped to include a constriction at a terminal end of the microfluidic channel. In other words, the microfluidic channel may be tapered at a terminal end. In some embodiments, the channel begins to narrow at a distance of approximately 50 μm to 150 μm or more from the terminal end and continues to narrow until the terminal end, e.g., in some embodiments, the channel begins to narrow at a distance of from about 60 μm to about 140 μm, from about 70 μm to about 130 μm, from about 80 μm to about 120 μm, from about 90 μm to about 110 μm, or about 100 μm, from the terminal end and continues to narrow until the terminal end. In some embodiments, the terminal end of the microfluidic channel may be a T-junction or another type of junction wherein the microfluidic channel meets one or more additional microfluidic channels. In some embodiments, a first side and a second side of the microfluidic channel may each narrow between approximately 10 μm and 20 μm over any one of the above distances, e.g., between about 11 μm and 19 μm, about 12 μm and 18 μm, about 13 μm and 17 μm, about 14 μm and 16 μm, or about 15 μm.

The above constriction allows for the metering of beads one-by-one at a channel outlet. This ability to release beads one at a time may be beneficial for a variety of bead uses. Accordingly, this feature has broad applicability to microfluidic devices in general where bead sorting applications are of interest.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., s or sec, second(s); min, minute(s); h or hr, hour(s); Mn, number average molecular weight; Mw, weight average molecular weight; and the like.

Example 1: Synthesis of Lanthanide Nanoparticles

Nanoparticles for use in preparation of the disclosed spectrally encoded microbeads were synthesized using a polymer-assisted hydrothermal approach combined with microwave irradiation. Chemical reagents and polymers [poly(ethylene glycol) (PEG) and poly(acrylic acid) (PAA)] for nanoparticle synthesis were purchased from Sigma-Aldrich (St. Louis, Mo.) and were used without further purification. Microwave synthesis was performed using a Biotage Initiator (Biotage AB, Uppsala, Sweden). Purification of the synthesized nanoparticles was performed by ultrafiltration using Amicon Ultra-15 centrifugal filter units with a 50,000 Dalton Molecular Weight Cutoff (MWCO) (Millipore, Billerica, Mass.), resulting in suspensions with a nanoparticle concentration of ~50 mg/mL in water. Luminescence spectra were measured using a FluoroMax-3 (Horiba Scientific, Kyoto, Japan) spectrofluorometer and the nanoparticle particle size distributions were measured using a Zetasizer Nano (Malvern Instruments, Malvern, UK).

Solutions (0.1 M) of the rare-earth (RE) dopants [$Sm(NO_3)_3$, $Dy(NO_3)_3$, $Eu(NO_3)_3$], $Y(NO_3)_3$, and $Na_3VO_4$ were prepared in advance. 14.2 mg of $Bi(NO_3)_3$ was added into 3 mL of a 10 w/w % solution of PEG (Mn~2,000). This solution was then rapidly dissolved through brief sonication before being heated to 70° C. in an oil bath under magnetic stirring. A solution of $Y(NO_3)_3$ (800 μL) and the RE solution (e.g., $Eu(NO_3)_3$)(50 μL) was premixed and then added drop-wise into the stirring PEG solution. The PEG solution instantly turned white upon addition of the Y+RE mixture. This solution was stirred for 30 minutes, followed by the drop-wise addition of the $Na_3VO_4$ solution (950 μL). The suspension turned yellowish at this stage and the mixture was again stirred for 30 min. The suspension was transferred into a glass vial suitable for microwave synthesis and was heated to 180° C. at 15 bar for 60 min. Upon removal from the microwave, the suspension was pure white. The material was pelleted in a 15-mL disposable centrifuge tube and the PEG supernatant was removed. The pellet was then re-suspended in 3 mL of deionized $H_2O$, to which was added 5 mL of a 10 w/w % PAA solution (Mn~1,400). This mixture was heated back up to 70° C. and stirred for 10 min. The solution was pH adjusted to 7.5 using 5 N NaOH and stirred for an additional 30 min. The suspension was then diluted 1:10 with deionized H2O and sonicated for 18 hours. After sonication, any larger phosphor particles were pelleted under centrifugation and the remaining translucent suspension was filtered consecutively through a 1 μm and 0.45 μm Polytetrafluoroethylene (PTFE) filters before being added to an ultracentrifugation filter unit for concentration and the removal of excess salts and polymers. After the entire reaction volume (~100 mL) had been passed through the membrane, the retained nanoparticles were washed 4 times with 15 mL of deionized water to exchange out the remaining solution. The final nanoparticle (NP) suspensions were white and milky in appearance and had a nanoparticle concentration of about 50 mg/mL.

Figure 6:
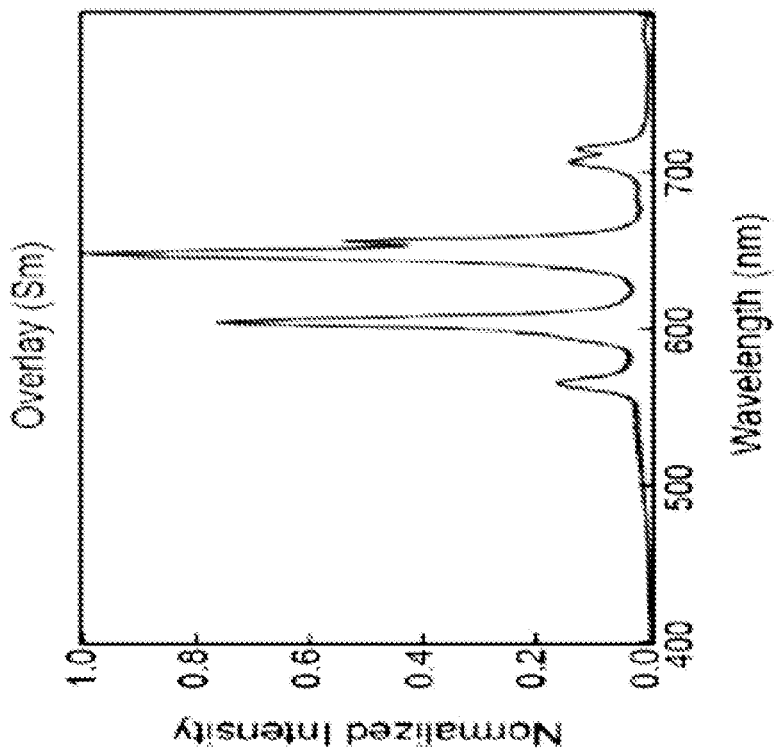
FIG. 6 provides a graph showing the reproducibility of lanthanide nanoparticle synthesis according to some embodiments of the present disclosure. Each individual batch of lanthanide nanoparticle suspensions were diluted 1:500 in DI water from the concentrated stock solutions. A luminescence emission spectrum (400-800 nm) was obtained using a FluoroMax-3 spectrofluorometer for all of these diluted stock solutions. The excitation was the same for all solutions (285 nm through a 3-nm slit width excitation monochromator) and the emission parameters were also held constant for all emitters (3-nm emission slit width, 1-nm increment steps, and 0.1 sec integration time at each step) with the exception of the Europium lanthanide nanoparticles which, due to their brightness, had slit widths of 1 nm at both monochromators. For each emitter shown, the left column shows the emission spectra of each individual batch synthesized as a stacked plot: (Panel A) Sm, 4 batches, (Panel B) Dy, 3 batches, and (Panel C) Eu, 5 batches. In the right column, the normalized emission spectra for all batches are shown as an overlay for each emitter. Typically, only one color is observed in the overlaid spectra since the high reproducibility of the batches results in several spectra that are coincident.
Figure 6:
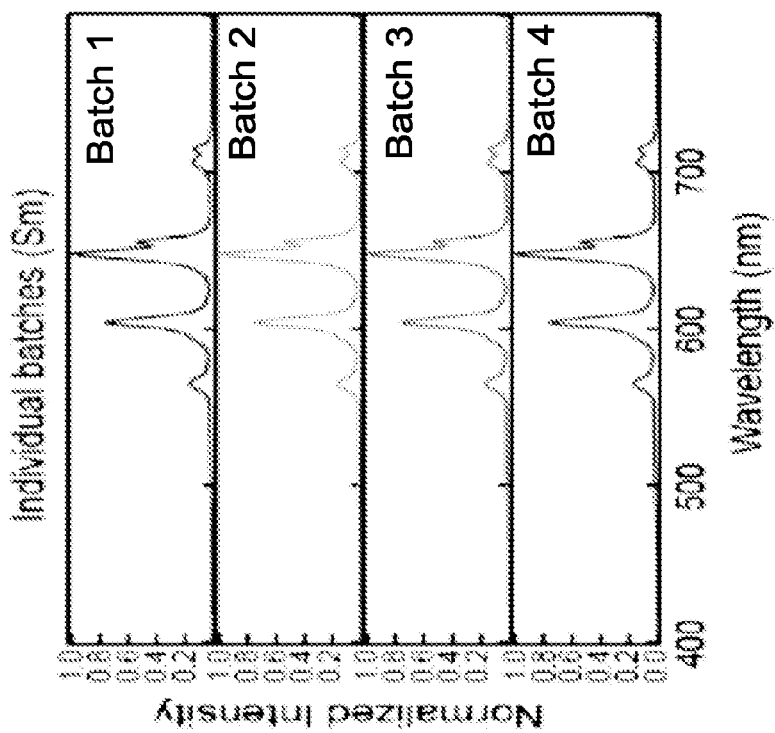
Figure 6:
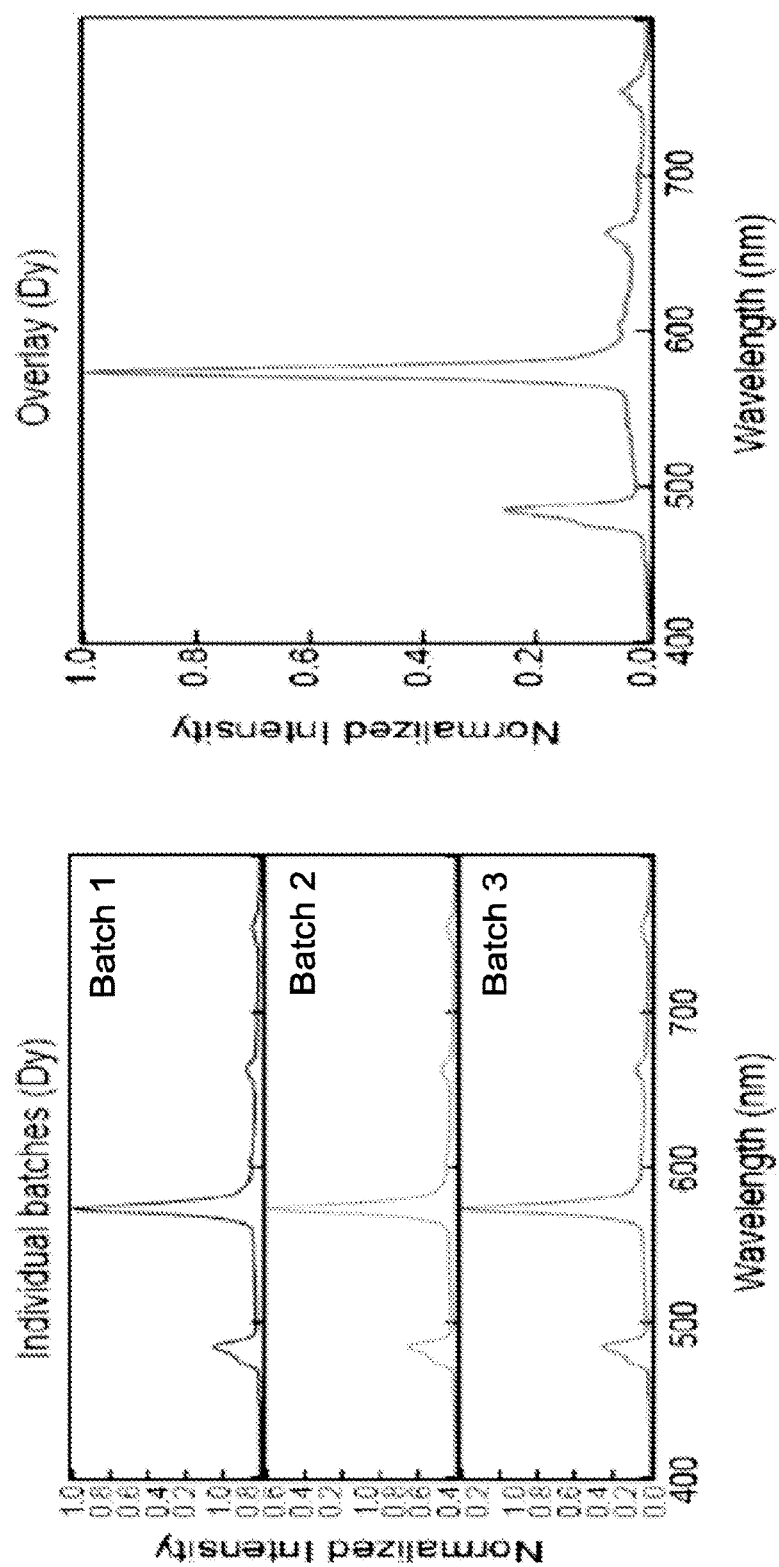
Figure 6:
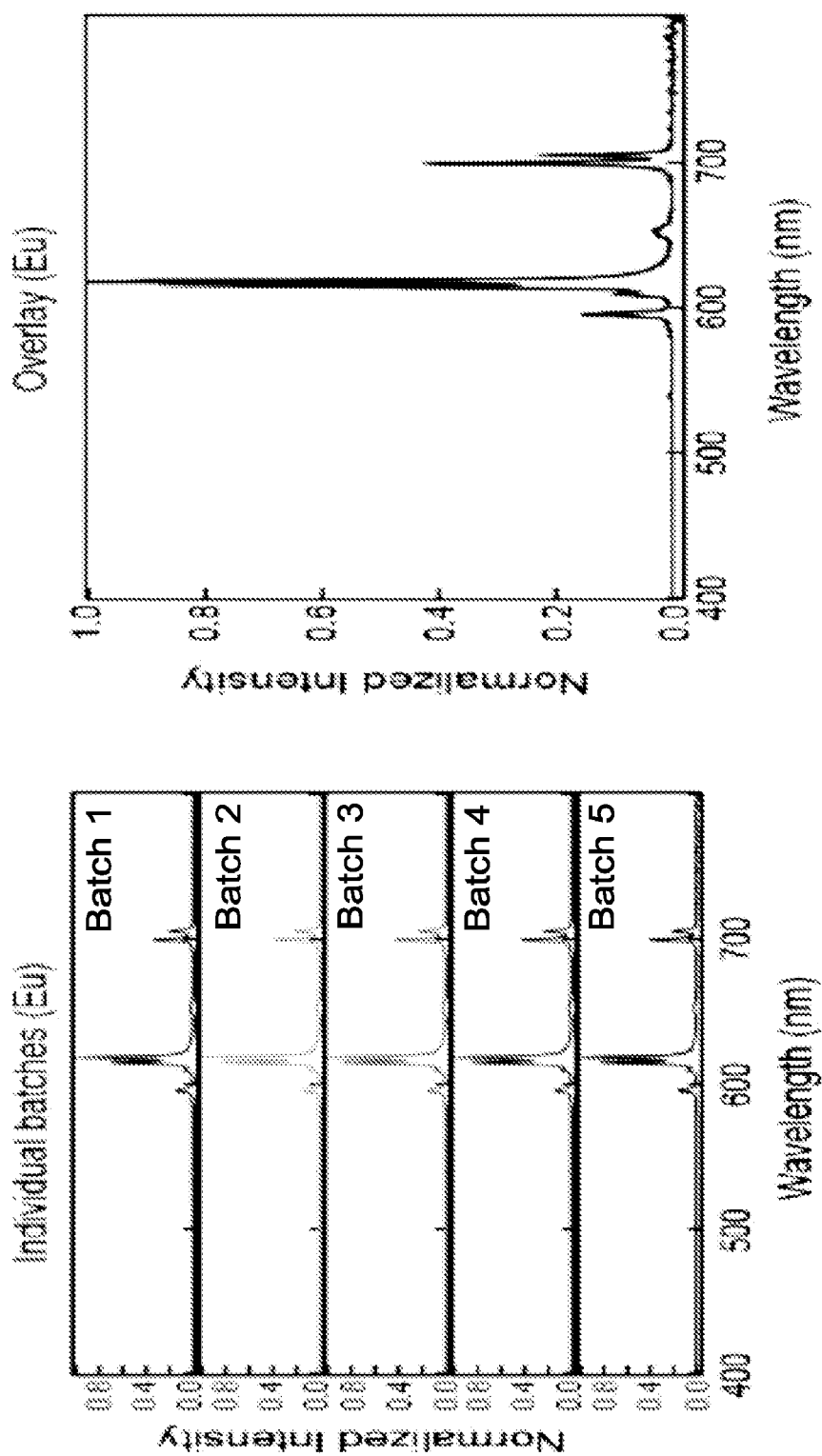

The product of the above synthesis is a crystalline YVO4 nanoparticulate host containing one of the trivalent rare earth dopants (Eu3+, Sm3+, or Dy3+), resulting in materials with unique emission spectra (FIG. 1, Panel A) when excited with UV light (FIG. 1, Panel A, inset). The nanoparticles have a size distribution from 30-160 nm (FIG. 1, Panel B) and are coated with poly(acrylic acid) to create stable aqueous suspensions (FIG. 1, Panel B, inset, illuminated with a UV lamp). Bismuth (at a 5-15% atomic replacement of yttrium) has also been incorporated into these nanoparticles to increase their UV absorption. The nanoparticles may be referred to herein simply by the rare earth dopant present (e.g., Eu). To test the reproducibility of nanoparticle production, multiple batches of each nanoparticle were synthesized and their emission spectra were compared (FIG. 6). In all cases, these spectra were virtually identical, demonstrating the ability to consistently and reproducibly produce nanoparticles.

Example 2: Synthesis of Ratiometrically Encoded Polymeric Beads

Microfluidic Device Production

To incorporate the prepared lanthanide nanoparticles into solid beads at programmed ratios, a custom, fully-automated microfluidic device was designed and fabricated. Devices were fabricated in poly(dimethylsiloxane) (PDMS, RTV 615, Momentive Performance Materials, Albany, N.Y.) by Multi-Layer Soft Lithography using 4" test-grade silicon wafers (University Wafer, South Boston, Mass.) coated with multiple layers of SU8 (Microchem Corp., Newton, Mass.) and AZ50 XT photoresists (Capitol Scientific, Austin, Tex.) patterned by standard photolithography processes.

All photolithography masks were designed using Auto-CAD (Autodesk, San Rafael, Calif.) and printed onto transparency film with a resolution of 30,000 dpi (FineLine Imaging, Colorado Springs, Colo.). To improve adhesion of subsequent photoresist layers, all wafers were first coated with a 5 µm layer of SU-8 2005 negative photoresist (Microchem Corp.) according to the manufacturer's instructions. All spin-coating steps were performed on a G3P-8 programmable spin coater (Specialty Coating Systems, Indianapolis, Ind.). After each coating step wafers were set on a flat surface for 10 to 20 minutes to allow photoresist to relax completely and reduce surface irregularities, except for the initial 5 µm adhesion layer of SU-8. All photoresist baking steps were done on aluminum-top hot plates (HS40A, Torrey Pines Scientific, Carlsbad Calif.). Mask alignment and photoresist exposure were done on a Quintel Q2001CT i-line mask aligner (Neutronix-Quintel, Morgan Hill, Calif.).

Bead synthesizer control molds were fabricated using SU-8 2025 photoresist according to the manufacturer's instructions for creating ~25 µm thick channels. Flow molds were constructed with five layers of photoresist, one using AZ50 XT positive photoresist (Capitol Scientific, Austin, Tex.), the other four using different types of SU-8. Layers 1 and 2 were developed separately, but layers 3-5 (all SU-8) were developed together, after they had all been exposed, as this was found to reduce bubble formation, improve height uniformity, and allow for significantly better staggered herringbone fabrication. After the 5th layer, layers 3-5 were developed for 6 min in SU-8 Developer, followed by hard baking for 2 hours at 165° C., with an initial ramp from 65° C. to 165° C. at 120° C./hr. The five layers were:

I) 5 µm thick SU-8 2005 layer for the high resistance push water input. Spin-coat: (1) 500 rpm for 5 s with 5 s ramp (spread), (2) 2900 rpm for 30 s with 8 s ramp (cast). Soft bake: 65° C. 2 min/95° C. 3 min/65° C. 2 min UV exposure: 7.4 s at 18.4 mW/cm2. Post exposure bake: 65° C. 2 min/95° C. 3 min/65° C. 2 min. Develop: 2 min in SU-8 Developer (Microchem).

II) 45 µm thick AZ50 XT layer to create rounded channels at valve locations. Spin-coat: (1) 200 rpm for 5 s with is ramp (spread), (2) 1400 rpm for 30 s with 5 s ramp (cast), (3) 3400 rpm for is with is ramp (edge bead removal). Soft bake: 65° C.-112° C. full speed ramp for 22 min Rehydrate overnight. UV exposure: 20 s×4 with 20 s pauses in between at 18.4 mW/cm2. Develop: 1:3 solution of AZ Electronic Materials AZ400k developer (Capitol Scientific). Hard bake: ramp from 65° C. to 190° C. at 10° C./hr, remain at 190° C. for 4 hrs.

III) 45 µm thick SU8-2025 layer for the lanthanide inputs, mixer channel, and oil channels. Spin-coat: (1) 500 rpm for 10 s with 5 s ramp (spread), (2) 1600 rpm for 30 s with 3.6 s ramp (cast). Soft bake: 65° C. 2 min/95° C. 10 min/65° C. 2 min UV exposure: 13.1 s at 18.4 mW/cm2. Post-exposure: 65° C. 2 min/95° C. 9 min/65° C. 2 min.

IV) 30 µm thick SU8-2025 layer on top of layer 3 in the mixer channel and downstream of the T-junction. Spin-coat: (1) 500 rpm for 10 s with 5 s ramp (spread), (2) 3500 rpm for 30 s with 10 s ramp (cast). Soft bake: 65° C. 2 min/95° C. 7 min/65° C. 2 min. UV exposure: 14.3 s at 18.4 mW/cm2. Post-exposure bake: 65° C. 3 min/95° C. 6 min/65° C. 2 min.

V) 35 µm thick SU8-2025 layer on top of layer 4 on the mixing channel for the staggered herringbone grooves. Spin-coat: (1) 500 rpm for 10 s with 5 s ramp (spread), (2) 2500 rpm for 30 s with 6.7 s ramp (cast). Soft bake: 65° C. 2 min/95° C. 7 min/65° C. 2 min UV exposure: 7 s at 18.8 mW/cm2. Post-exposure bake: 65° C. 2 min/95° C. 6 min/65° C. 2 min.

All molds were silanized by exposure to trichloromethylsilane (Sigma-Aldrich, St. Louis, Mo.) vapors for 60 minutes. Each flow mold was then coated with a 4 mm thick layer of Momentive Materials RTV 615 (R.S. Hughes, Oakland, Calif.) mixed at a ratio of 1:5 (cross-linker:elastomer) using a Thinky AR-250 planetary centrifugal mixer (Thinky USA Inc, Laguna Hills, Calif.). This 4 mm thick layer was subsequently degassed in a vacuum chamber for 60 minutes. All control molds and slides for mounting the devices were spin coated with a ~20 µm thick layer of RTV 615 mixed at a ratio of 1:20 via a 2 step spin process: (1) 500 rpm for 5 s with a 5 s ramp (spread), and (2) 1900 rpm for 60 s with a 15 s ramp (cast). Flow molds, control molds, and coated slides were baked at 80° C. for 1 hour, 40 minutes, and 20 minutes, respectively. Following baking, PDMS flow layers were peeled from molds, cut to the appropriate size, punched with a drill press (Technical Innovations, Brazoria, Tex.) at inlet and outlet ports, and aligned to control layers (still remaining on the molds). The aligned devices were then baked for an additional hour before being cut from the molds, punched to create control access ports, and placed on the coated slides. The entire assembly was then baked at 80° C. for 1-12 hours to finalize device bonding. Synthesis devices were mounted on regular microscope glass slides.

Microfluidic Device Operation

Valves in the microfluidic devices were actuated by 10 mm pneumatic solenoid valves (Festo Corp., Hauppauge, N.Y.) driven by an ethernet-based, programmable fieldbus I/O system with digital output modules (750-841 Programmable Fieldbus Controller, 750-504 4-Channel Digital Output Module, Wago Corp., Germantown, Wis.). All fluids were injected into the microfluidic devices using pressure-driven flow from custom-made containers. Pressurized air to operate the valves and push fluids into the chips was supplied by a set of manual precision pressure regulators connected to the house air supply through a series of high efficiency filters for oil and particulate removal. A custom software platform written in MATLAB® (The MathWorks Inc., Natick, Mass.), with a graphical user interface, allowed for real time control and script-driven automation of all aspects of the chip operation, for bead synthesis. The UV light source for droplet polymerization was a Leica® EL6000 fluorescence excitation light source with a metal halide bulb and liquid light guide filtered by an Omega® UV filter cube set #XF02-2 (80 nm band around 330 nm).

Bead Synthesis

Encoded beads were generated by varying ratios of three pre-polymer input solutions each containing different lanthanide nanoparticles. The three monomer input solutions used in the microfluidic bead synthesizer all contained purified water with 42.8% v/v 700 MW PEG-diacrylate (Sigma-Aldrich), 6% v/v 2-hydroxy-4'-(2-hydroxyethoxy)-2-methylpropiophenone ("Irgacure® 2959", a photoinitiator, Sigma-Aldrich) dissolved in methanol at 0.33 g/mL, and 5% v/v YVO4:Eu (25 mg/mL). One of the input solutions also contained 21.3% v/v YVO4:Dy (10 mg/mL) and one of the others contained 21.3% v/v YVO4:Sm (10 mg/mL). Droplets were formed into a continuous flowing stream of light mineral oil (Sigma-Aldrich) that contained 2% v/v Abil® EM90 (Evonik Industries, Germany) and 0.05% v/v Span™ 80 (Sigma-Aldrich) as surfactants to eliminate droplet merging and sticking to the PDMS walls. On device UV illumination was used to polymerize the droplets into beads downstream of the T-junction.

All monomer-lanthanide mixtures were injected into the chip from custom-made containers using PEEK™ capillary tubing with an inner diameter of 65 μm and a length of 30.5 cm to provide high input resistance relative to the resistance of the staggered herringbone channel. This helps minimize any potential flow rate errors due to inaccuracies in measuring the resistance of the staggered herringbone channel or fluctuations in set pressures. On-chip resistors optimized for stable drop production at the T-junction with input pressures near the middle of the pressure regulator range were used on the oil and push water inputs. To reduce oxygen inhibition of the PEG-diacrylamide polymerization, these containers were pressurized with nitrogen (95-99% purity) supplied by a high-precision, high-speed, computer-controlled pressure regulator with eight independent output channels (MFCS-FLEX, 8 channels, 0-1000 mBar range, Fluigent SA, Paris, France). For the same reason, the microfluidic device was surrounded by a 95-99% pure nitrogen atmosphere during operation. The high gas permeability of PDMS ensures that the interior of the microfluidic device will equilibrate with this nitrogen atmosphere. The compressed nitrogen for these purposes was supplied by a membrane-based nitrogen generator (Membrane Module 210, Generon IGS, Pittsburgh, Calif.) fed from the building compressed air supply.

After polymerization, the beads were smaller than the droplets, mostly due to oxygen-driven cross-linking inhibition on the droplet surface, and this reduction in size was highly dependent on the UV dose delivered to the droplets (the lower the dose, the smaller the beads). For the experimental conditions described here, the typical diameter shrinkage was approximately 7 μm, resulting in beads of approximately 46 μm+/−1 μm. The measured error corresponded to approximately half a pixel in the image and thus the actual size variation of the beads is likely smaller. Sizes of beads were measured by fitting a circle to 3 user-selected points on the perimeter of the bead in a brightfield image using NIS-Elements (Nikon Instruments, Melville, N.Y.).

Precise flow control from each of the lanthanide inputs facilitates the accurate programming of spectral codes. This was accomplished by performing a calibration routine to directly measure relative hydraulic resistances and then solving the coupled flow equations (1) and (2) to determine the pressure ($P_n$) from each input (n) to achieve the desired flow rates ($Q_n$):

$$Q_n = \frac{P_n - P_{mix}}{R_n} \qquad \text{(Eqn. 1)}$$

$$Q_{tot} = \frac{P_{mix}}{R_{mix}} \qquad \text{(Eqn. 2)}$$

Where $Q_{tot}$ is the total flow rate from all lanthanide inputs, $P_{mix}$ is the pressure at the inlet to the mixing channel where all lanthanide input streams come together, and $R_{mix}$ is the resistance of the mixing channel. The resistance of each input ($R_n$) was determined relative to a fixed reference standard, PEG-diacrylate with food coloring, flowed into one of the lanthanide inputs. The pressures at these two inputs were set to the same value and the flow rate ratio ($Q_n/Q_{ref}$) was determined by measuring the width taken up by each fluid in the channel. When the input pressures are equal, equation (1) reduces to:

$$\frac{Q_n}{Q_{ref}} = \frac{(P_n - P_{mix})/R_n}{(P_{ref} - P_{mix})/R_{ref}} = \frac{R_{ref}}{R_n} \qquad \text{(Eqn. 3)}$$

$R_{mix}$ was determined by flowing lanthanide in pre-polymer at one of the lanthanide inputs at a fixed pressure and then measuring the pressure ($P_{mix}$) where the inputs come together at the entrance to the mixing channel. Under these conditions $Q_{tot}=Q_n$ so from equations (1) and (2):

$$\frac{R_n}{R_{mix}} = \frac{P_n - P_{mix}}{P_{mix}} \qquad \text{(Eqn. 4)}$$

$P_{mix}$ was measured by opening the valve to a second lanthanide input and adjusting the pressure at this second input until there was no flow at this second input. Once the relative resistances for each of the lanthanide inputs ($R_n$) and the resistance downstream of the inputs ($R_{mix}$) is determined, the system of equations (1) and (2) can be solved to obtain the pressures needed for the desired flow rates of each lanthanide in monomer for accurately hitting each targeted spectral code.

The microfluidic bead synthesizer depicted in FIG. 2 operates in two stages. In stage one, the different lanthanides, suspended in poly(ethylene glycol) diacrylate, flow into the device and mix in a staggered herringbone mixer. During this mixing, the relative flow rates from the different lanthanide inputs determine the relative abundance of each lanthanide in a bead. In stage two, droplets are generated by flowing the lanthanide mixture into an oil stream at a T-junction, and then polymerized into beads through on-chip UV illumination. After producing beads with each mixture, the mixing channel is flushed with high-pressure water to clear the channel, the pressures are adjusted to pre-programmed values automatically for the next code, and the process repeats. Precise control over lanthanide flow rates, which is achieved by setting pressures based on a set of coupled flow equations and calibration parameters (see above), facilitates the accurate development of targeted spectral codes. The device depicted in FIG. 2, Panels C and D, was prepared as described above and incorporates controls for up to 8 lanthanide inputs.

To test both the feasibility of using lanthanide nanoparticles to create uniquely identifiable spectral codes and the performance of the microfluidic bead synthesizer, a set of ratiometrically-encoded beads including varying levels of Dy and Sm and a constant level of Eu was synthesized. Codes were determined by the relative ratios of Dy/Eu and Sm/Eu, with the constant level of Eu providing an internal normalization to correct for spatial and temporal variations in either excitation intensity or detection efficiency. A two-dimensional grid of 24 ratiometric codes was synthesized containing 6 distinct levels of both Dy and Sm based on preliminary measurements suggesting these codes would be distinguishable with high accuracy. In three hours of fully automated unattended device operation, a set of 24 spectral codes with each code including approximately 1500 beads was produced.

Example 3: Imaging of Spectrally Encoded Beads

Microfluidic Device Production

To measure the lanthanide luminescence ratios in the spectrally encoded beads, an additional custom microfluidic device was developed to create an ordered linear array of ~190 beads within a narrow serpentine channel (FIG. 3, Panel A) covering a ~1 mm² area. Beads in the serpentine can be loaded and unloaded using on-chip valves in the fluidic circuit, allowing for efficient imaging of large numbers of beads.

All photolithography masks were designed using AutoCAD (Autodesk, San Rafael, Calif.) and printed onto transparency film with a resolution of 30,000 dpi (FineLine Imaging, Colorado Springs, Colo.). To improve adhesion of subsequent photoresist layers, all wafers were first coated with a 5 µm layer of SU-8 2005 negative photoresist (Microchem Corp.) according to the manufacturer's instructions. All spin-coating steps were performed on a G3P-8 programmable spin coater (Specialty Coating Systems, Indianapolis, Ind.). After each coating step wafers were set on a flat surface for 10 to 20 minutes to allow photoresist to relax completely and reduce surface irregularities, except for the initial 5 µm adhesion layer of SU-8. All photoresist baking steps were done on aluminum-top hot plates (HS40A, Torrey Pines Scientific, Carlsbad Calif.). Mask alignment and photoresist exposure were done on a Quintet Q2001CT i-line mask aligner (Neutronix-Quintel, Morgan Hill, Calif.).

Imaging device control molds were fabricated using SU-8 2025 according to the manufacturer's instructions for creating ~25 µm thick channels. Imaging device flow molds had the following layers:

I) ~50 µm thick layer of AZ 50 XT photoresist to create rounded channels at valve locations. Spin-coat: (1) 200 rpm for 5 s with a 1 s ramp (spread), (2) 750 rpm for 30 s with a 5 s ramp (cast), and (3) 2750 rpm for 1 s with a 1 s ramp (edge bead removal). Soft bake: 25 minutes with ramp between 65° C. and 112° C. at full speed, and allowed to cool to room temperature. Rehydrate overnight. UV exposure: 25 s×3 at ~18 mW/cm². Develop: 1:3 solution of AZ AZ400k developer in water. Hard bake: Ramp from 65° C. to 190° C. at 10° C./hour, remaining at 190° C. for 4 hours.

II) ~50 µm thick layer of SU-8 2050 to create all flow channels. This layer was fabricated largely according to the manufacturer's instructions, although it was found that soft baking set to ramp between 65° C. and 95° C. (rather than simply transferring wafers between hot plates set to 65° C. and 95° C.) helped prevent formation of bubbles within the photoresist.

All molds were silanized by exposure to trichloromethylsilane (Sigma-Aldrich, St. Louis, Mo.) vapors for 60 minutes. Each flow mold was then coated with a 4 mm thick layer of Momentive Materials RTV 615 (R.S. Hughes, Oakland, Calif.) mixed at a ratio of 1:5 (cross-linker:elastomer) using a Thinky AR-250 planetary centrifugal mixer (Thinky USA Inc, Laguna Hills, Calif.). This 4 mm thick layer was subsequently degassed in a vacuum chamber for 60 minutes. All control molds and slides for mounting the devices were spin coated with a ~20 µm thick layer of RTV 615 mixed at a ratio of 1:20 via a 2 step spin process: (1) 500 rpm for 5 s with a 5 s ramp (spread), and (2) 1900 rpm for 60 s with a 15 s ramp (cast). Flow molds, control molds, and coated slides were baked at 80° C. for 1 hour, 40 minutes, and 20 minutes, respectively. Following baking, PDMS flow layers were peeled from molds, cut to the appropriate size, punched with a drill press (Technical Innovations, Brazoria, Tex.) at inlet and outlet ports, and aligned to control layers (still remaining on the molds). The aligned devices were then baked for an additional hour before being cut from the molds, punched to create control access ports, and placed on the coated slides. The entire assembly was then baked at 80° C. for 1-12 hours to finalize device bonding. Imaging devices were mounted on cyclic olefin copolymer slides (COP480R, Pure Slides LLC, Medford, Mass.) to minimize the fluorescence background.

Microfluidic Device Operation

Valves in the microfluidic devices were actuated by 10 mm pneumatic solenoid valves (Festo Corp., Hauppauge, N.Y.) driven by an ethernet-based, programmable fieldbus I/O system with digital output modules (750-841 Programmable Fieldbus Controller, 750-504 4-Channel Digital Output Module, Wago Corp., Germantown, Wis.). All fluids were injected into the microfluidic devices using pressure-driven flow from custom-made containers. Pressurized air to operate the valves and push fluids into the chips was supplied by a set of manual precision pressure regulators connected to the house air supply through a series of high efficiency filters for oil and particulate removal. A custom software platform written in MATLAB® (The MathWorks Inc., Natick, Mass.), with a graphical user interface, allowed for real time control and script-driven automation of all aspects of the chip operation, for the imaging chips.

"Sieve" valves positioned at the end of the serpentine channel of the microfluidic device permitted fluid flow while retaining beads, facilitating pressure-driven packing of beads within the channel and maximizing imaging throughput. Multiple output ports collected both buffer and bead wastes; fluid injection ports at either side of the device allowed flushing of the serpentine from either side to clear stuck particles. These devices are mounted on cyclic olefin polymer slides (COP480R; Pure Slides, LLC., Medford, Mass.) to minimize autofluorescence; the PDMS itself was not significantly autofluorescent. Device control lines were pressurized to 25 psi (for fully sealing valves) and 35 psi (for sieve valves).

Prior to loading, bead batches were washed ten times in a solution of 1× Phosphate Buffered Saline (PBS) with 0.5% Tween and twice in a solution of 1×PBS with 0.1% Tween before being diluted to a working concentration of 100-200 beads per µL in 1×PBS with 0.1% Tween. Bead solutions (~25 µL) were loaded into Tygon® tubing (using a 1 mL syringe), and connected directly to the device. Buffers were stored in pressurized vials connected to the device via Tygon® tubing. During serpentine loading, both bead and buffer inputs were pressurized at 3-5 psi and excess buffer was directed to the waste port. During imaging, buffer solution pressure was reduced to ~1 psi to relax bead packing. After imaging, the output was directed to a separate bead waste port to collect imaged beads for further use.

Bead Imaging

Bead imaging was performed using a Nikon® Ti microscope (Nikon Instruments, Melville, N.Y.) with a custom built illuminator. Because the microscope objectives are not transparent to the short wavelength UV illumination used to excite the lanthanides, a transillumination geometry as shown in FIG. 3 was used. Light from a full-spectrum 300 W Xenon arc lamp (Newport, Irvine, Calif.) was collected, reflected off a 400 nm long pass mirror (CVI Melles-Griot, Albequerque, N. Mex.) to reject visible light, then passed through a shutter and an excitation filter wheel (Sutter Instrument Co., Novato, Calif.), before being focused into a 3 mm diameter deep UV liquid light guide (Newport). The excitation wheel allowed switching between UV illumination for lanthanide excitation and visible light illumination for finding beads and imaging the device during bead loading. For UV imaging, the illumination light was filtered with a 292/27 excitation filter (Semrock, Rochester, N.Y.) paired with UG11 absorptive glass (Newport). The illumination intensity at the sample was ~12.5 mW/cm$^2$. For visible light imaging the residual visible light reflected by the 400 nm long pass mirror was used, which was further filtered with a 409 nm long pass filter (Semrock), infra-red reflective mirror (Edmund Optics), and an OD 1.0 neutral density filter.

The other end of the liquid light guide was mounted on the condenser mount of a Nikon Ti microscope, where the light was collimated by a fused silica lens (Newport) and projected onto the sample. Emitted light from the sample was collected by a Plan Apo 4×/0.2NA (Nikon Instruments, Melville, N.Y.) objective, with a UV blocking filter (Edmund Optics, Barrington, N.J.) placed between the objective and the sample. Emitted light was filtered through an emission filter wheel mounted beneath the objective before being focused onto the camera. An image stack was collected which included six different images acquired through the following filters (all from Semrock): 482/35, 510/84, 543/22, 572/15, 615/20, and 630/92. The filters used here were chosen using a Monte Carlo optimization procedure to select filters which minimize the unmixing error. Typical exposure times were 5 seconds for the first four channels and 1 second for the last two. The camera used was an Andor DU-888 (Andor Technology, Belfast, Northern Ireland) operated in conventional readout mode at 13 MHz with 2×2 binning. The microscope and camera were controlled by Micro-Manager software (Edelstein A, Amodaj N, Hoover K, Vale R, Stuurman N (2010) in *Current Protocols in Molecular Biology* (John Wiley & Sons, Inc.)).

Bead images for testing bead autofluorescence in conventional dye channels were acquired on a Nikon Ti microscope with a 10×/0.3 Plan Fluor objective and a Coolsnap HQ2™ CCD camera (Photometrics, Tucson, Ariz.). Illumination was from a Sutter XL lamp (Sutter Instrument Company, Novato, Calif.) and a Chroma 89000 filter set (Chroma Technology, Bellows Falls, Va.) was used to define the excitation and emission channels. The lamp was operated at full power and the exposure time for each image was 1 second.

Linear Unmixing and Image Analysis

All data analysis was performed with custom software written in MATLAB®. Reference spectra for unmixing were acquired from beads doped with a single lanthanide. These beads were spotted on quartz coverslips (to minimize background fluorescence) and an image stack was acquired as described above. The background was subtracted using a local background estimation procedure and the mean luminescence of the beads in each channel was measured. The device background spectrum was measured from a region of the microfluidic device where no beads were present. These reference spectra were then normalized so that each spectrum summed to one.

Before linear unmixing, the images of the beads in the serpentine device were corrected for camera bias and dark current by subtracting a dark image. Dark images were acquired by averaging 100 frames acquired with the same exposure times as the fluorescent images, but with the camera shutter closed. The image stack was then flat-field corrected by dividing each image by a corresponding flat-field image. Flat-field images were acquired by averaging 100 frames captured through each emission filter with white-light transmitted illumination and no sample present on the microscope. While the use of an internal standard corrected for variations in excitation intensity across the field of view, wavelength-dependent pixel response nonuniformity was monitored. Linear unmixing was then performed using standard least squares analysis to fit the intensity of each pixel of the measured image stack to a sum of the reference spectra times the abundance of each lanthanide. This unmixing process reduced the six-channel raw data to a four-channel image stack including background fluorescence and Dy, Eu, and Sm luminescence.

Beads were then identified in the unmixed image by median filtering the Eu channel and performing adaptive local thresholding. The threshold parameters were adjusted to include as many pixels as possible in each bead while maintaining separation between them. For each bead identified, the pixel by pixel ratio of Dy to Eu and Sm to Eu luminescence was calculated and the median Dy/Eu and Sm/Eu luminescence ratio was recorded. To minimize the effect of wavelength-dependent pixel response nonuniformity on the CCD, only beads within the central 300×300 pixels on the CCD were analyzed. Because the data returned by linear unmixing were on an arbitrary scale, a variation of Iterative Closest Point matching was used to determine overall scaling factors along the Dy/Eu and Sm/Eu axes to best map the observed data to the programmed codes (Besl P J, McKay N D (1992) A Method for Registration of 3-D Shapes. *IEEE Trans Pattern Anal Mach Intell* 14:239-256; and Segal A V, Haehnel D, Thrun S (2009) in *Proceedings of Robotics: Science and Systems (RSS)*). Briefly, the algorithm works as follows: an initial transformation is determined that maps the brightest bead along each axis to the highest programmed level of that lanthanide. This transformation is applied to the data and the closest programmed level to each measured bead is determined. The transformation that best matches the measured beads to their closest programmed levels is determined, and the process is iterated until convergence. To account for small systematic errors between different serpentines, these scaling factors were determined separately for each serpentine. This systematic variation was largest along the Sm/Eu dimension, and correcting it reduced the overall CV by ~0.6%. This correction was statistically significant as compared to resealing an equal number of subsets of the data without regard to which serpentines they originated from.

The Gaussian mixture model (GMM) was fit in MATLAB® and standard deviation ellipses and numbers of standard deviations between points and cluster centroids were determined using the Cholesky decomposition of the covariance matrix (Press W H, Teukolsky S A, Vetterling W T, Flannery B P (2007) *Numerical Recipes 3rd Edition: The Art of Scientific Computing* (Cambridge University Press). 3rd Ed.). Cross-validation was performed by splitting the bead data into ten disjoint sets, training the GMM on nine, and then testing the classification accuracy on the remaining test set. This was repeated for each of the ten test sets in turn. Measurement errors were determined by replicate imaging of two different serpentines of beads. For each bead, the mean and standard deviation of five repeated measurements were calculated. The standard deviations were then grouped by lanthanide ratio and averaged to give the statistical error plotted in FIG. 5, Panel B.

Imaging Results

Figure 7:
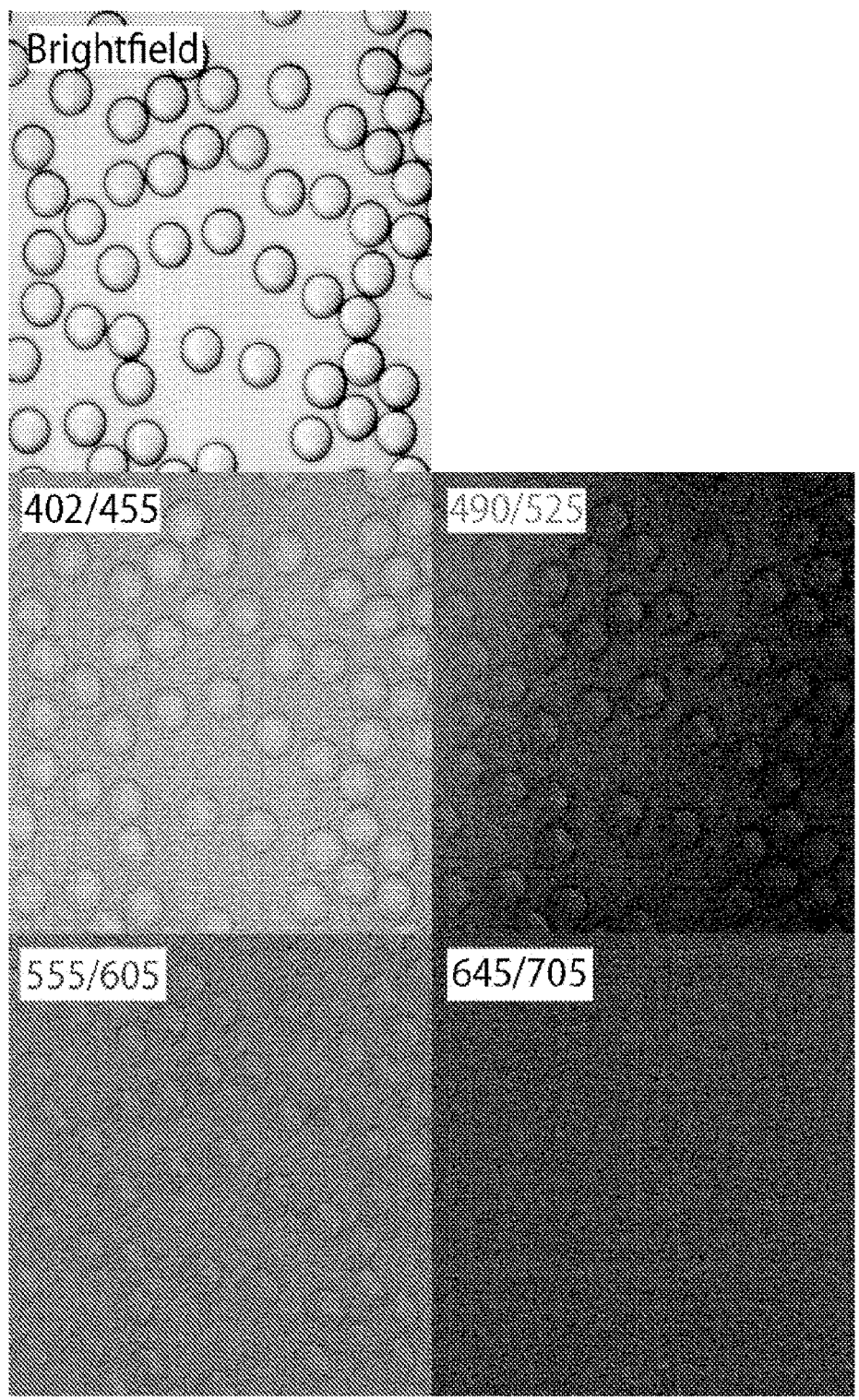
FIG. 7 provides images showing compatibility of exemplary spectrally encoded beads according to some embodiments of the present disclosure with commonly used visible fluorophores. A sample of the 24-code beads were imaged using a Chroma Sedat quad filter set (#89000), a Lambda XL lamp, CoolSNAP™ HQ2 camera, 10x/0.3 NA objective, and 1 sec exposure time for each luminescence channel. All four channel combinations were imaged, and the corresponding images are labeled with the excitation and emission centers of the filter sets. The 402/455 (DAPI channel) image shows weak luminescence; the other channels show negligible luminescence with the luminescence in the Cy5 channel being undetectable.

Initial images of the beads showed that they are highly monodisperse, with a mean diameter of 46.4±1.0 µm. Images of these beads at commonly used fluorescence wavelengths revealed minimal luminescence of the lanthanides in the fluorescein, Cy3, and Cy5 emission channels, indicating that these beads are compatible with assays using these dyes for detection (FIG. 7).

Figure 4:
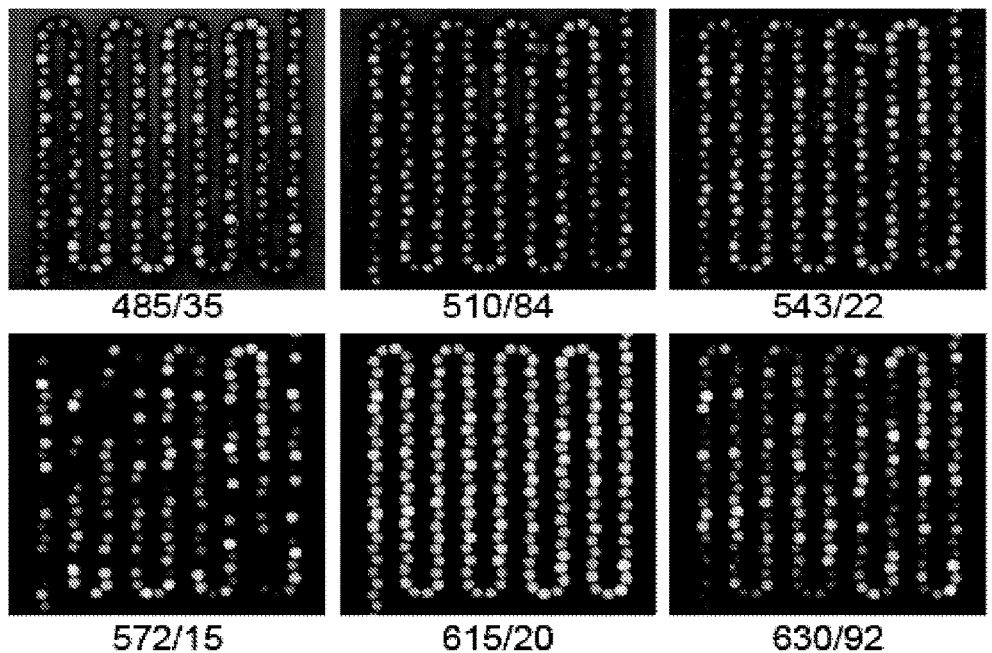
FIG. 4 provides images and graphical data associated with an analysis procedure according to some embodiments of the present disclosure. (Panel A) Raw data in each of six luminescence channels. Data are scaled linearly. (Panel B) Reference spectra used for unmixing. (Panel C) Left: Linearly scaled black and white images of unmixed data from each channel (Dy, Eu, and Sm), with black set to the minimum intensity in the image and white set to the maximum intensity. Right: Bright field image of the same field of view. (Panel D) False color overlay of Dy, Eu, and Sm luminescence with scaling as in Panel C (shown here in greyscale).
Figure 4:
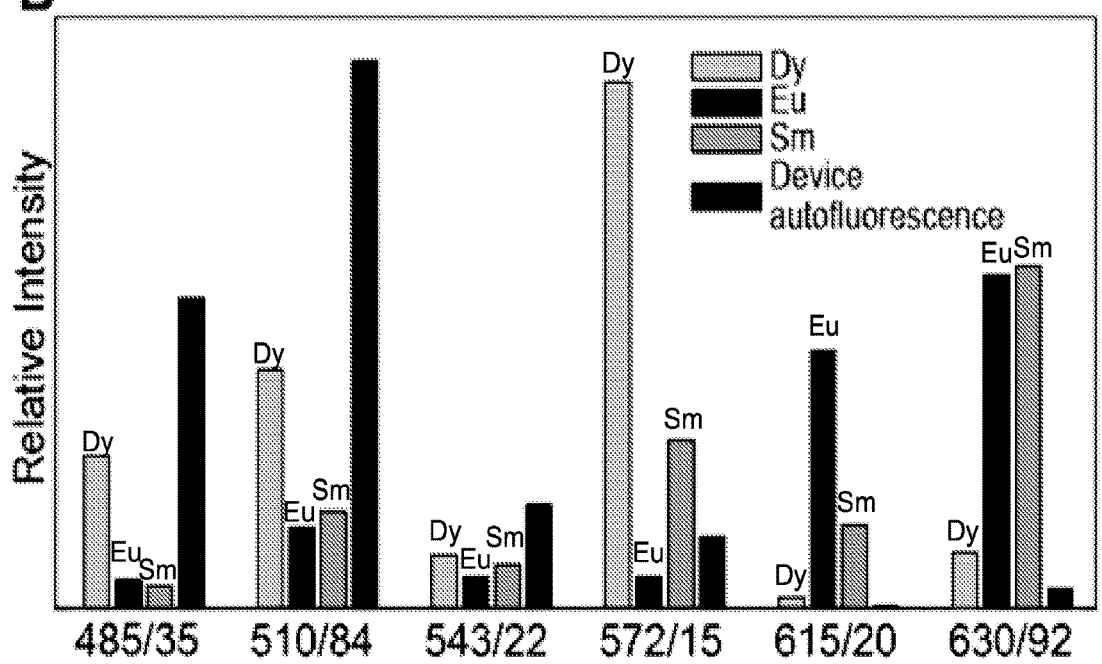
Figure 4:
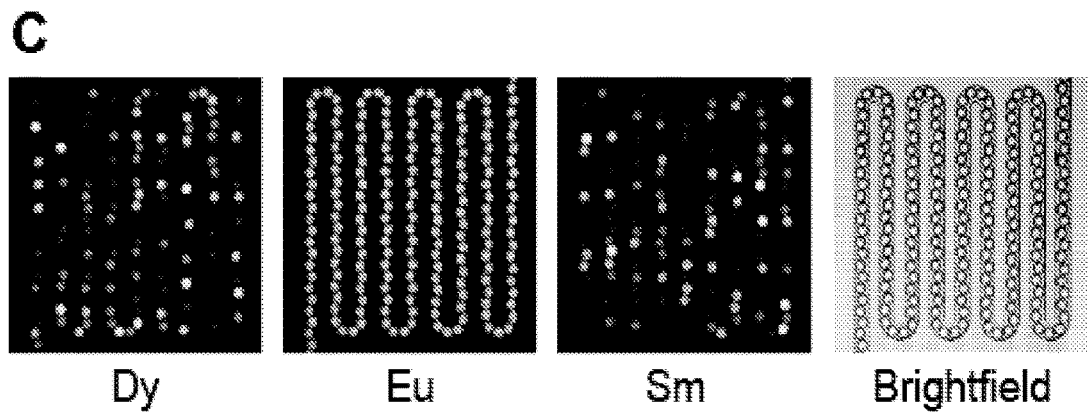
Figure 4:
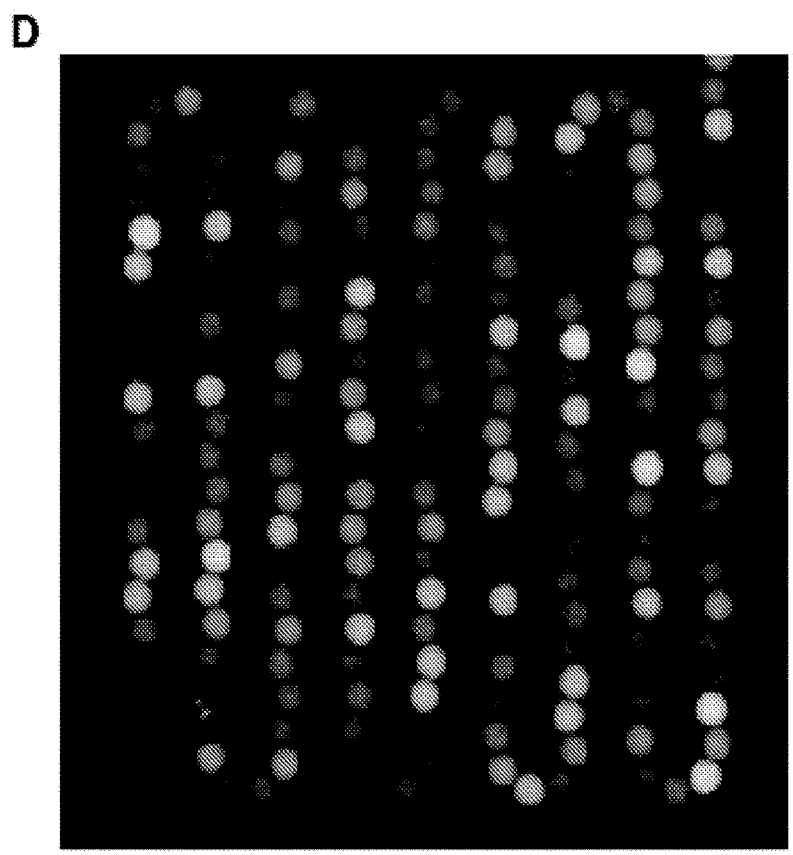

Luminescence emission from the beads was detected in six spectral bands defined by emission filters chosen to pass the characteristic emission peaks of each lanthanide (FIG. 1, Panel A and FIG. 4, Panel A). The intensities of individual lanthanides were then determined by linear unmixing, which expresses the measured images as a sum of component images multiplied by each component's characteristic spectrum. Here, the three lanthanides Dy, Eu, and Sm were used, as well as the autofluorescence of the microfluidic device within which the beads are held (FIG. 4, Panel B). The unmixing error (the difference between the measured images and the component images times their spectra) was <2% for a typical image set. A typical set of unmixed images is shown in FIG. 4, Panel C. To identify the lanthanide ratios in each bead, beads in the image were first identified by adaptive local thresholding of the Eu channel. For each identified bead (spanning ~90 pixels), the Dy/Eu and Sm/Eu ratios were then calculated on a pixel by pixel basis, and median ratios for each bead were recorded.

Identification of Spectral Codes

Figure 5:
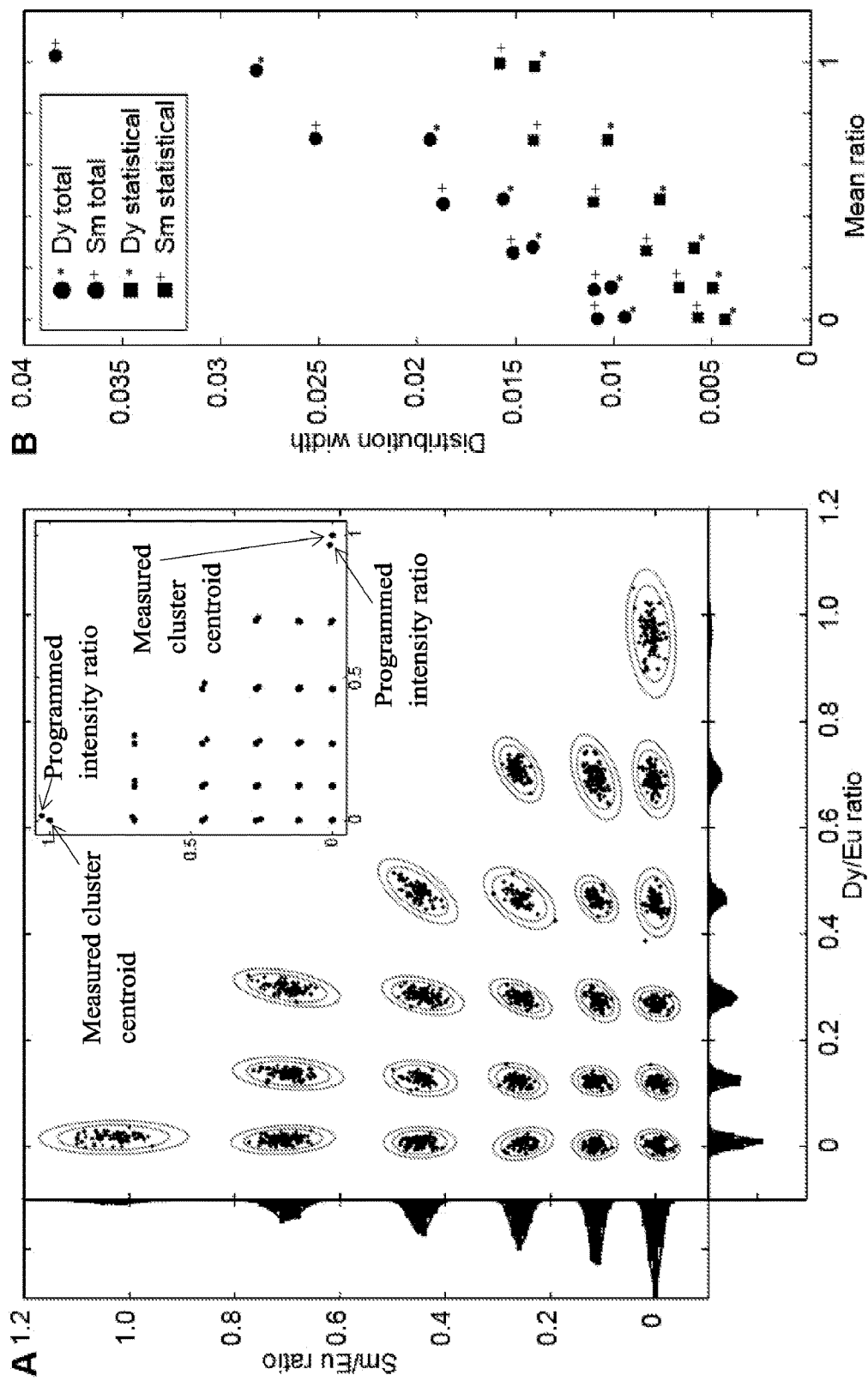
FIG. 5 provides a graphical representation of a 24 code matrix according to some embodiments of the present disclosure. (Panel A) Scatter plot of the median Dy/Eu and Sm/Eu luminescence ratios for 10 filled serpentines (1926 beads), with points false colored according to their Sm/Eu and Dy/Eu ratios (shown here in greyscale). Each point represents one bead. Grey ellipses around each code cluster illustrate three- and four-sigma contours derived from fitting a Gaussian mixture model to the data. Histograms of bead ratios in the Dy/Eu and Sm/Eu channels (black) and their corresponding Gaussian fits (grey fit lines) are shown along each axis; these histograms group all codes together. Inset: Measured cluster centroids and their corresponding programmed intensity ratios; the root mean square deviation between the programmed ratios and the measured ratios is 0.014. (Panel B) Standard deviations calculated from Gaussian fits to the bead ratio histograms in Panel A as a function of ratio (filled circles, identified with "*" for Dy and "+" for Sm). Square symbols illustrate the statistical standard deviation determined from replicated imaging of the same serpentine of beads.
Figure 8:
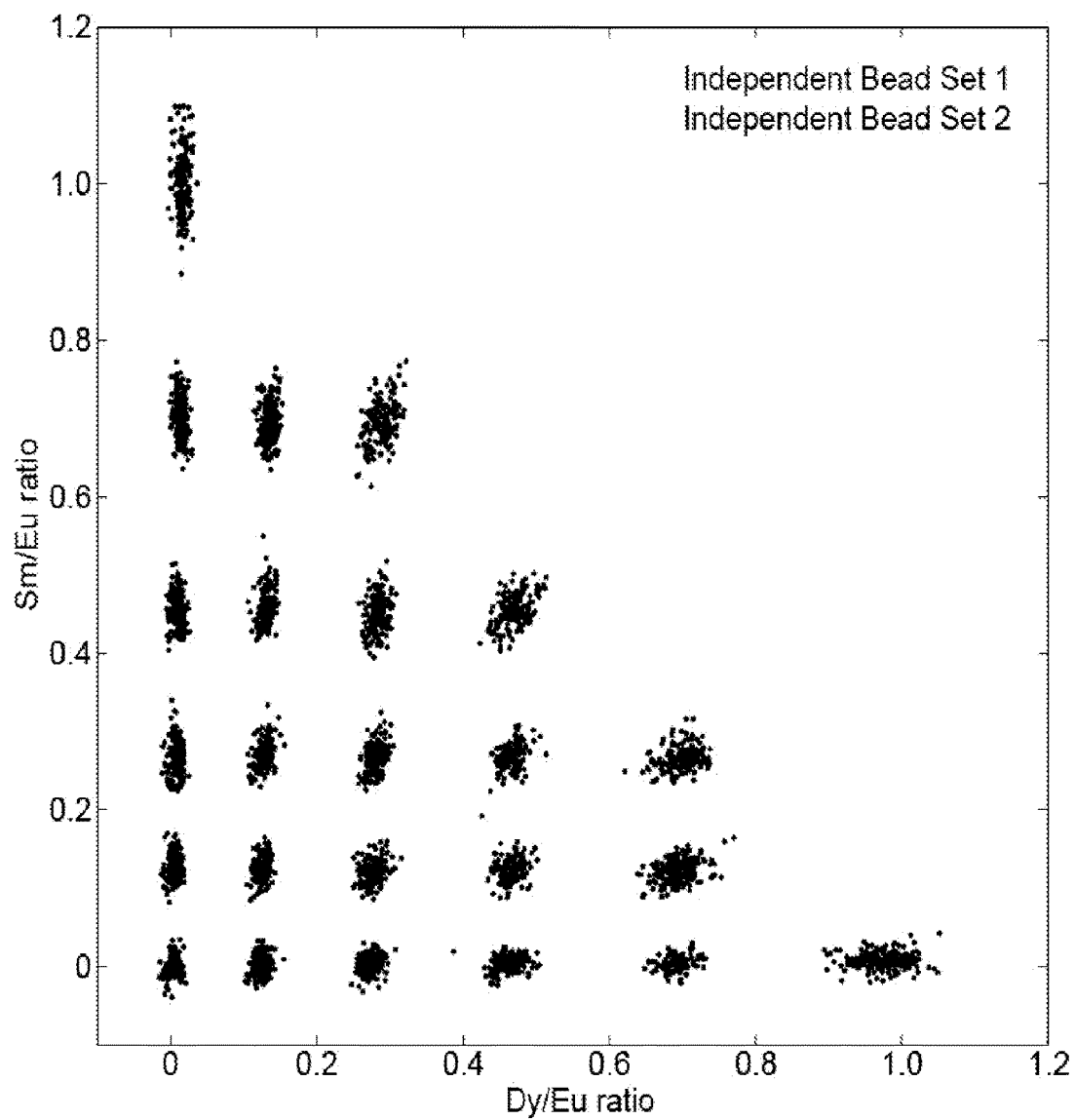
FIG. 8 provides scatter plots of two different batches of synthesized beads (Bead Set 1 (grey) and Bead Set 2 (Black)) according to some embodiments of the present disclosure. The two batches were synthesized on different dates and imaged on the same date. The Set 1 batch of beads is missing one code due to a computer error.
Figure 9:
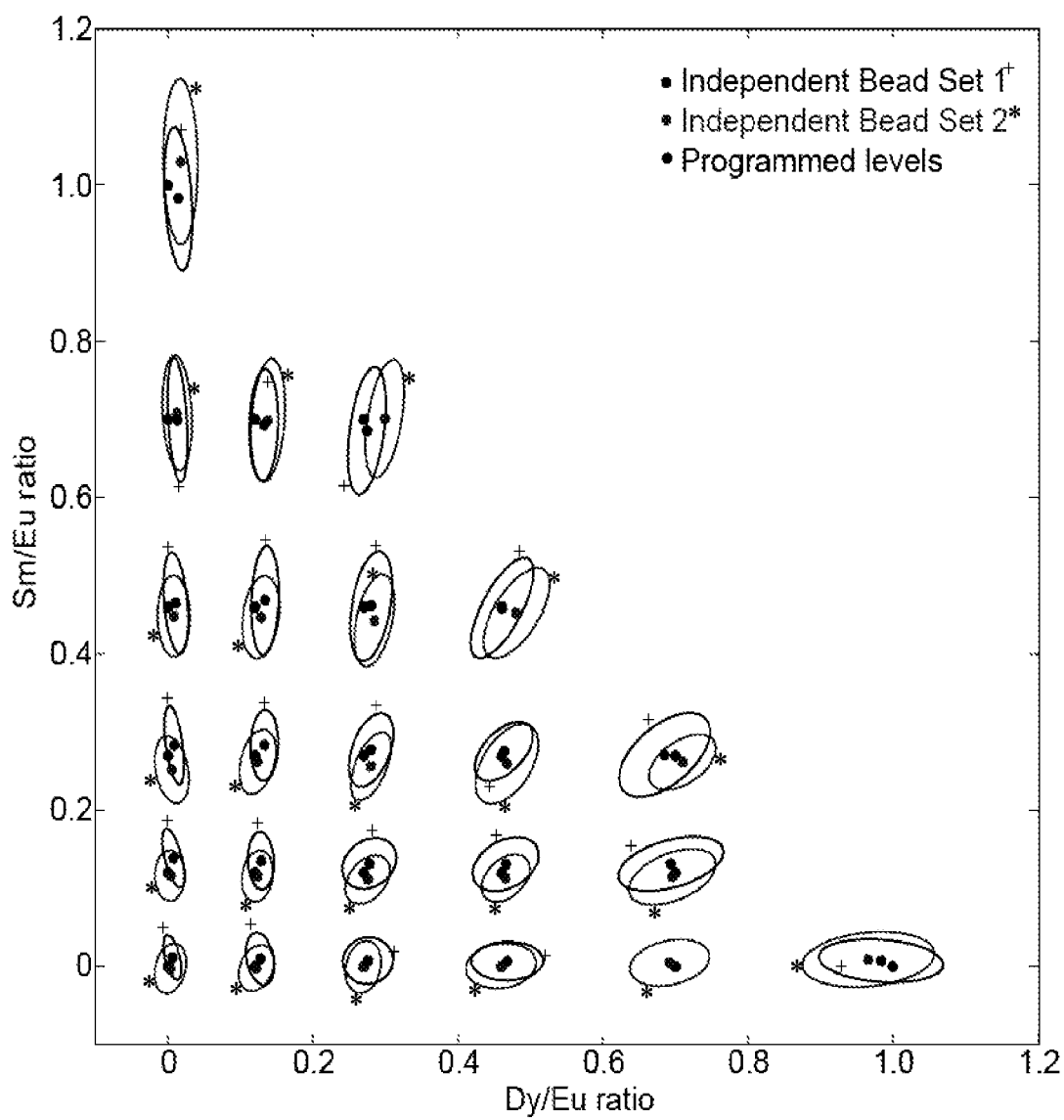
FIG. 9 provides a graph comparing programmed ratios (black) and measured code centroids and three sigma error ellipses for the Set 1 ("*") and Set 2 ("+") beads referenced in FIG. 8.

To be practically useful, each code within an encoded bead set should cluster tightly around the predetermined, programmed ratios. The results of imaging 10 bead-filled serpentines containing a representative sample of 1926 beads from the 24 code set are shown in FIG. 5, Panel A. To determine cluster centroids for each code, k-means clustering was performed on the data, using the programmed values as the starting cluster centroids. The synthesized beads for each code cluster tightly, with the measured values for each code agreeing very well with the targeted values (inset FIG. 5, Panel A): the mean distance between the programmed ratios (0, 0.12, 0.27, 0.46, 0.70, and 1) and the measured ratios is only 0.014. Discounting the 0,0 code, the mean fractional error between the measured and programmed levels (distance from programmed to measured divided by distance of programmed to origin) is 2.9%. A second independently-generated code set shows similarly precise agreement with the programmed levels (FIGS. 8 and 9), indicating that the disclosed synthesizer produces spectrally-encoded beads with both high accuracy and repeatability. These code sets were synthesized independently with a three-week gap between the syntheses, and both code sets were imaged several additional weeks after the syntheses, demonstrating bead and reagent stability.

Another important consideration for a robust encoding scheme is that beads from different codes cluster tightly together and far from other codes, preventing misidentification of beads. The root mean square (RMS) deviation of individual beads from their code centroid, calculated as above, is 4%. To quantify how accurately beads can be assigned to a code, a two-dimensional Gaussian was fit to each code cluster.

Understanding and minimizing errors is important in order to maximize the code space that can be achieved with a given encoding scheme. The distribution of measured bead ratios around their programmed values can result from both errors in bead synthesis and bead imaging. These synthesis and imaging errors, in turn, are composed of both a systematic, instrumental component as well as a statistical, shot noise (either photon or lanthanide nanoparticle number) component. To probe the relative contributions of these sources of error in the measurements, the mean error for each Dy/Eu level and each Sm/Eu level was calculated, independent of the concentration of the other lanthanide. The histograms of the Dy/Eu and Sm/Eu ratios for all beads are shown at the edges of the scatter plot in FIG. 5, Panel A, along with Gaussian fits to the data. The widths (standard deviations) from these Gaussian fits are plotted (FIG. 5, Panel B), along with the statistical measurement error (determined by repeated imaging of the same serpentine of beads). The statistical measurement error accounts for roughly one half of the total error in the Dy/Eu channel and between one half and one third of the total error in the Sm/Eu channel. While these other sources of error can be further reduced, the fact that the results are within 2-3 fold of the measurement shot noise limit indicates that these other errors are relatively small.

The described experiments have demonstrated a system designed to precisely generate beads containing ratiometric spectral codes using a microfluidic device and luminescent lanthanide nanoparticles. 24 uniquely identifiable codes have been created containing a single reference level of Eu and 6 levels each of both Sm and Dy. Measurements of ~2,000 beads from this code set establish both that the measured ratios closely match the desired programmed ratios and that these codes are easily distinguished from one another, validating the accuracy and precision of this technique Importantly, both this scheme and the device used to produce these codes can be extended to significantly larger code sets.

Exemplary embodiments of the disclosed devices are unique in incorporating automated on-chip mixing with multiple input streams while accurately achieving programmed ratiometric codes (error<3%), with low variation within a code (4%), and precise control over bead size (CV<2.5%). An exemplary bead synthesizer described herein incorporates eight lanthanide inputs and is scalable with respect to both the number of lanthanide inputs and the rate of bead synthesis.

The ultimate performance of a spectral encoding scheme depends both on the number of encoding species and the number of intensity levels of each that can be reliably distinguished. The number of distinguishable intensity levels is inversely proportional to deviations from the programmed error level; therefore, minimization of synthesis and measurement errors is necessary to maximize the code space. These results establish that beads can be synthesized with a mean deviation from the programmed ratio of 2.9%. This number is significantly smaller than deviations from programmed intensities seen for QDs indicating that lanthanide nanoparticles suffer much less from energy transfer and re-absorption between particles.

The code set demonstrated above can be expanded through a minimization of code variation and the addition of other lanthanides. If, for example, it is assumed that the errors in intensity ratios are normally distributed, and require that the midpoint between any two programmed codes is at least four standard deviations from each other (corresponding to a misidentification probability of less than $10^{-4}$), then the current intra-code variation of 4% should allow the resolution of seven intensity levels for Dy/Eu and Sm/Eu. By reducing the total error to the statistical measurement error in FIG. 5, the number of resolvable levels would increase to 12 per lanthanide while maintaining a code-calling accuracy rate greater than 99.99%.

A number of lanthanide nanoparticles with different dopants and distinct emission spectra have been synthesized, including erbium, thulium, holmium, and cerium/terbium. By incorporating these lanthanide nanoparticles, the code space size can be increased to $\sim 7^6 = 117,649$. In addition to the discussed downconverting (UV-excited) $YVO_4$ nanophosphors, there are also upconverting lanthanide nanophosphors that emit in the visible region upon excitation in the near-IR. By utilizing upconverting nanoparticles with the emitting species Dy, Er, Eu, Ho, Sm, Tb, and Tm an additional six ratiometric channels may be provided. By alternating excitation between UV and near-IR sources, it is therefore possible to separate the spectra of upconverting and downconverting nanocrystals. Such a system combining upconverting and downconverting nanoparticles could have a code space as large as $7^{12}$, approximately 14 billion.

The methodology and device described here allows for efficient and accurate synthesis of spectrally encoded beads using microfluidics and lanthanide nanoparticles. Given an expanded code space with additional lanthanide nanoparticles, this platform enables a multitude of diverse assays, including immuno-diagnostics, small molecule library screening, and combinatorial synthesis approaches.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 4: Peptide Synthesis Using Lanthanide Nanoparticle Encoded Microbeads

Materials and Methods
Bead Production:
Amine-functionalized polyacrylamide beads were produced using a microfluidic device as described previously herein. Beads containing Europium alone were composed of purified water containing 27% v/v PEG-diacrylamide, 27% v/v amine-functionalized PEG-diacrylamide, 8% v/v lithium acylphosphinate (LAP) photoinitiator, and 5% v/v $YVO_4$:Eu (25 mg/mL). Beads containing a mixture of Europium and Dysprosium were composed of the same reagent mixture, with the addition of 16% v/v $YVO_4$:Dy.

Peptide Synthesis:
Each peptide synthesis reaction started with ~200 µL of packed encoded polymer beads suspended in a solution of 1×PBS with 0.1% Tween. The first amino acid (Proline) was added to beads manually to optimize amino acid loading. For this process, amine-functionalized polyacrylamide beads were loaded into 10 mL polypropylene syringes for manual peptide synthesis (New England Peptide; Gardner, Mass.). Beads were washed 3× with ~5 mL of methanol, an additional 2× with ~5 mL of dimethylformamide (DMF), and allowed to swell in dimethylformamide for 30 minutes. After swelling (and ejection of remaining DMF), beads were mixed with 5 mL of 0.1 M Fmoc-Pro-OH and 2.5 mL of 0.1 M 2-(1H-Benzotriazole-1-yl)-1,1,3,3 tetramethyluronium hexafluorophosphate (HBTU) and 0.4 M 4-methylmorpholine in DMF and incubated for an additional 30 minutes. Following coupling, beads were washed an additional 3× in DMF and the Fmoc protecting group on the nascent peptide chain was removed via exposure to 5 mL of 20% 4-methylpiperidine in DMF for 2 minutes. Following deprotection, beads were again washed 3× in DMF, resuspended in DMF, and loaded into Symphony™ peptide synthesizer (Protein Technologies, Inc.) reaction vessels for automated addition of the remaining amino acids. For the amino acids in positions 2-7 within the peptide chain relative to the C-terminus, beads were first incubated with 3 volumes of 20% piperidine in DMF and mixed for 2 minutes and 30 seconds. Following this incubation, beads were washed 3× with DMF and then exposed to 2 volumes of 0.1 M Fmoc-protected amino acid in DMF and 1 volume of 0.4 M 4-methylmorpholine in DMF with mixing for 10 minutes. This washing and incubation process was repeated once more (referred to as "double coupling"), followed by a final 3× wash in DMF.

For amino acids in positions 8-14, the coupling followed the double coupling procedure outlined in the previous paragraph with the exception that each coupling step was incubated for 20 minutes.

For the final amino acid, the 20 minute double coupling procedure was followed by a 5 minute incubation with a solution of 20% 4-methylpiperidine in DMF (to remove the final Fmoc protecting group), 3 30 second washes with methanol, and drying under nitrogen for 10 minutes.

Side Chain Deprotection:
Dried beads were transferred from the Symphony™ reaction vessels to 10 mL polypropylene syringes using a metal spatula. Beads were then incubated in 5 mL of a 95% trifluoroacetic acid, 2.5% triisopropylsilane, and 2.5% water solution for 2 hours at room temperature on a shaking block to cleave off side chain protecting groups. At the end of this incubation, the TFA/TIS/water solution was ejected to waste and beads were washed ~5× with deionized water and an additional 3-4× with a solution of 1×PBS with 0.1% Tween.

Peptide Cleavage from Beads:
Beads for peptide cleavage and peptide quality control via mass spectrometry were transferred to a 1.5 mL polypropylene Eppendorf tube. Beads were then pelleted via centrifugation at maximum speed in a benchtop centrifuge for 1 minute and washed 2-3× in a solution of 1% formic acid, 50% acetonitrile, and 50% water. Following the final wash, beads were resuspended in between 20 µL (for single bead cleavage experiments) and 1 mL of 1% formic acid, 50% acetonitrile, and 50% water and incubated in a heat block at 95° C. for 1 hour. Beads were again pelleted via centrifugation at maximum speed and the supernatant (containing the cleaved peptides) was analyzed via LC-MS/MS mass spectrometry. To assess the minimum number of beads required to generate sufficient samples for LC-MS/MS analysis, we prepared a suspension of beads in 1% formic acid, 50% acetonitrile, and 50% water (as described above), generated a 1:2 dilution series to create samples with progressively smaller numbers of beads, and then counted the number of beads within each Eppendorf tube. Figures used to illustrate peptide quality and cleavage sites were generated using WebLogo software, Crooks et al., *Genome Research*, 14:1188-1190 (2004).

Manual Immunoassays:

Peptide-conjugated beads suspended in 1×PBS with 0.1% Tween were further diluted via addition of 1×PBS with 0.1% Tween to a final concentration of about a 5-10 µL pellet of packed beads within a total volume of 50 µL. 1 µL of either Alexa-555 conjugated anti-myc antibody, Alexa-647 conjugated anti-FLAG antibody, or both antibodies were then added to each reaction, and this final mixture was protected from light and incubated on a nutating platform at 4° C. overnight (more than 12 hours). Following this incubation, beads were washed 3× with 1×PBS with 0.1% Tween via pelleting and resuspension, pipetted onto a quartz slide and covered with a quartz coverslip for imaging on an inverted microscope. To determine bead code identity, beads were imaged and analyzed as described previously herein. To determine antibody loading, beads were imaged using standard Cy3 and Cy5 filter cube sets with a 100 ms exposure time in each channel.

On-Chip Immunoassays:

On-chip immunoassays were conducted using the same reagent solutions and incubation times as described above for the standard immunoassays.

Microfluidic Devices:

PDMS molding masters and devices for the microfluidic bead reactor and bead imaging and release device were produced as described previously herein.

Peptide Synthesis and Immunoassays

Figure 10:
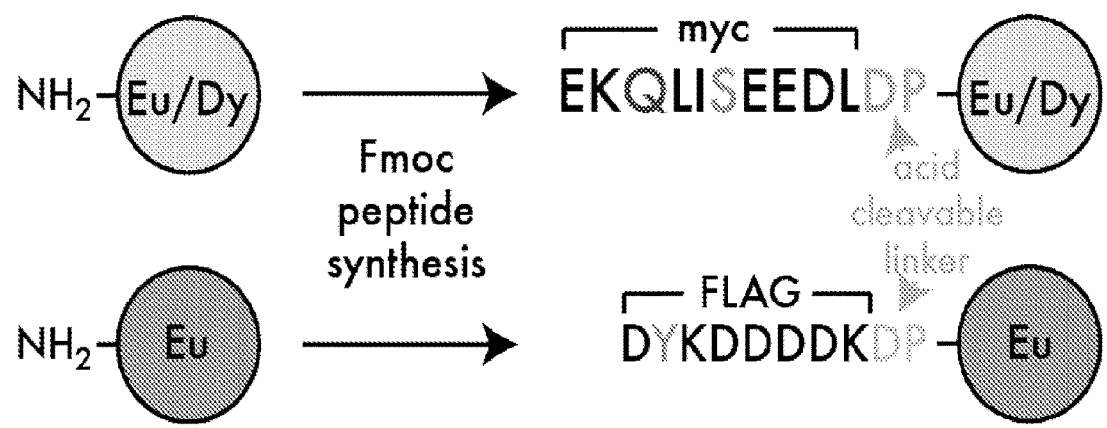
FIG. 10 provides a schematic of peptide synthesis on spectrally encoded beads.

To demonstrate the feasibility of using spectrally encoded beads as a substrate for solid phase peptide synthesis, two different well-characterized epitope tag peptides (FLAG and myc) (EKQLISEEDL (SEQ ID NO:1) and DYKDDDDK (SEQ ID NO:2) respectively) were synthesized on amine-functionalized polyacrylamide beads containing different combinations of lanthanide nanoparticles. The FLAG peptide was synthesized on beads containing only Europium (Eu) nanoparticles, and the myc peptide was synthesized on beads containing both Eu and Dysprosium (Dy) nanoparticles (FIG. 10). In both cases, peptides were attached to the beads via an aspartic acid-proline dipeptide linker that can be cleaved under orthogonal conditions to peptide synthesis reactions. This linker remains conjugated to the beads during all peptide synthesis steps (facilitating downstream on-bead immunoassays) but can be cleaved to release peptides from beads for quality control via mass spectrometry.

Figure 11:
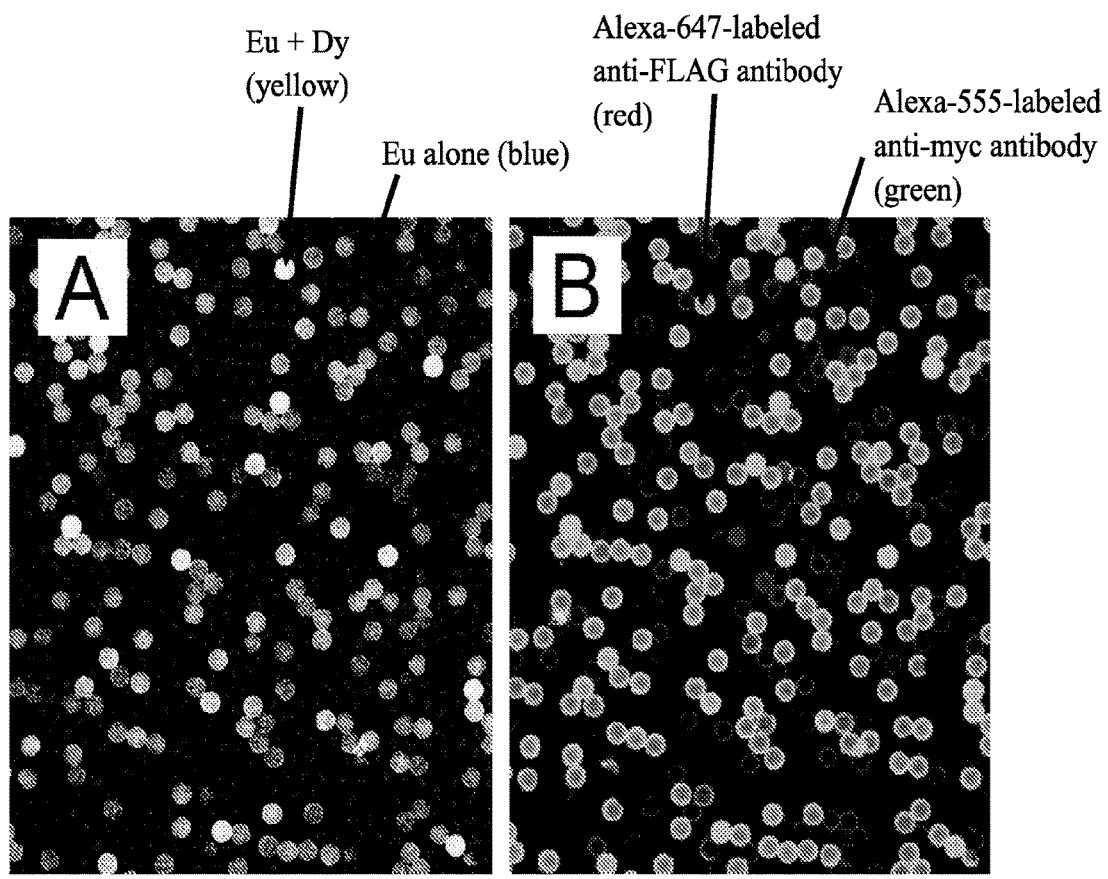
FIG. 11 provides false color images demonstrating that embedded codes are robust to peptide synthesis conditions. (Panel A) Image showing beads containing either Eu alone (blue) or a combination of Eu and Dy (yellow) after on-bead synthesis of either FLAG peptide (Eu beads, blue) or myc peptide (Eu/Dy beads, yellow). (Panel B) Image showing binding of Alexa-647-labeled anti-FLAG antibody (red) and Alexa-555-labeled anti-myc antibody (green) to encoded beads.
Figure 12:
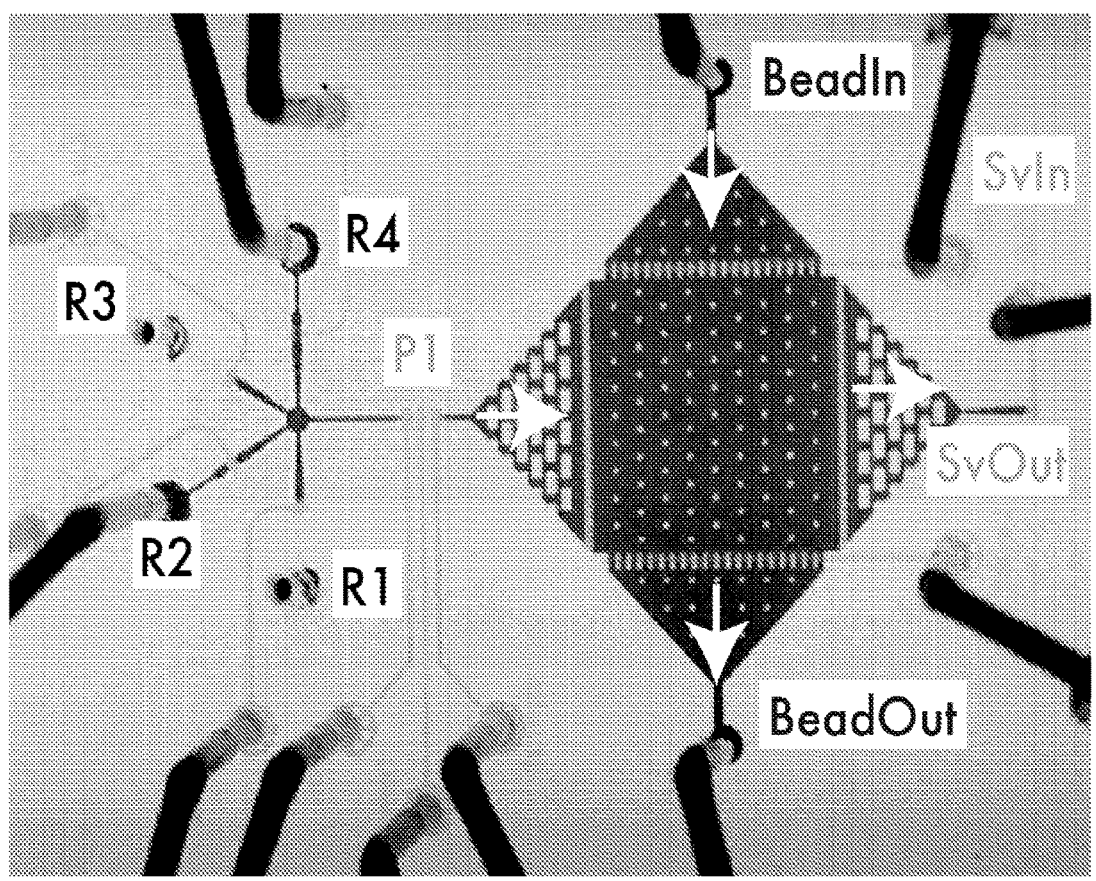
FIG. 12 provides a photograph showing the microfluidic bead reactor utilized for the immunoassays described in Example 4. The device features input and output channels (BeadIn, BeadOut) for loading beads into a single main reaction chamber, as well as 4 additional input channels (R1-R4) and a single output channel for introducing reagents into the reaction chamber. Flow is controlled by 4 valves that control reagent inputs, a pump (P1) that controls reagent flow rates, and 2 sieve valves (SvIn, SvOut) that retain beads during reagent exchanges.

Following synthesis, the Eu beads coated with FLAG peptides and the Eu/Dy beads coated with myc peptides were mixed with Alexa-647-labeled anti-FLAG antibodies and Alexa-555-labeled anti-myc antibodies, incubated overnight, washed to remove all unbound antibody, and then imaged at multiple wavelengths to identify the embedded codes (as described above) and with Cy3 and Cy5 filter sets to image bound labeled anti-FLAG and anti-myc antibodies. Both codes were easily identified post peptide synthesis, demonstrating that the embedded codes are robust to the harsh conditions required for peptide synthesis (FIG. 11, Panel A). In addition, the images demonstrated strong binding of labeled antibodies to the peptide-conjugated beads, with anti-FLAG antibodies binding only to the FLAG-conjugated Eu beads, and anti-myc antibodies binding only to the myc-conjugated Eu/Dy beads (FIG. 11, Panel B). Reactions took place both in standard reaction tubes and in a custom-made microfluidic bead reactor fabricated from polydimethylsiloxane (PDMS) (FIG. 12).

Figure 13:
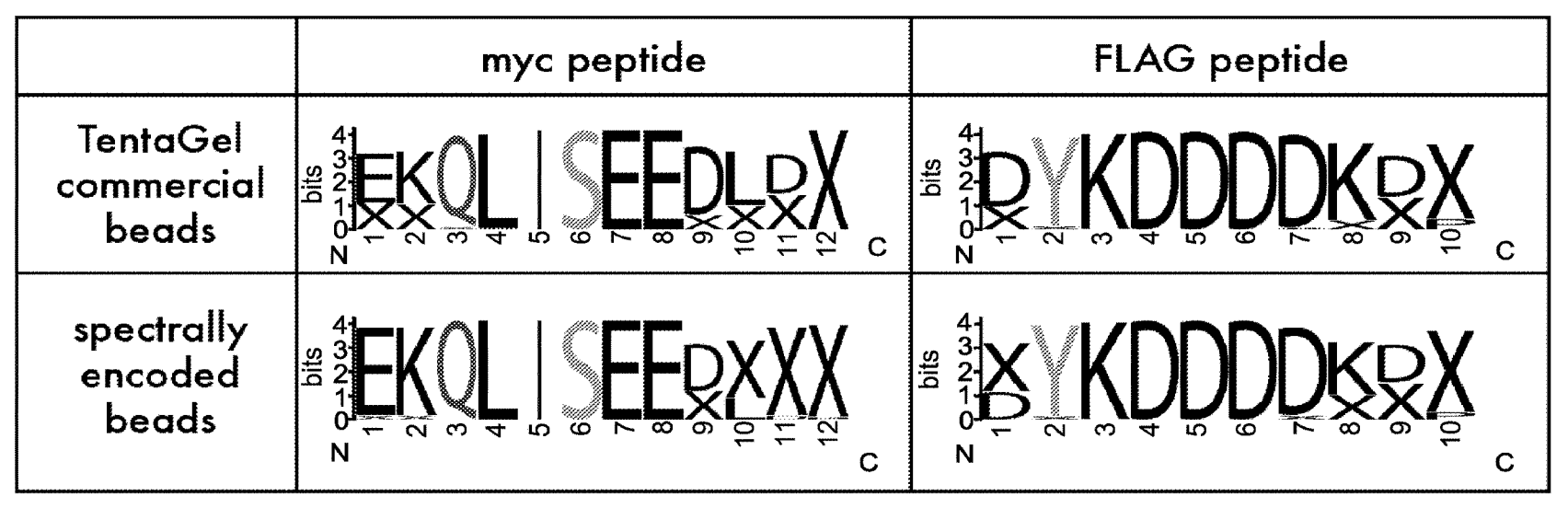

In addition to the immunoassays described above, the peptides were released from the beads by boiling them in a solution of 1% formic acid, 50% acetonitrile, and 50% water (which cleaves the aspartic acid-proline dipeptide linker) and then evaluated for quality via mass spectrometry. The peptides synthesized on spectrally encoded beads were of comparable quality to peptides synthesized on commercially available TentaGel™ beads (FIG. 13). In addition, a dilution series was performed and it was determined that peptides could be detected from single beads, with an estimated peptide loading level of 50 fmol per bead.

Figure 14:
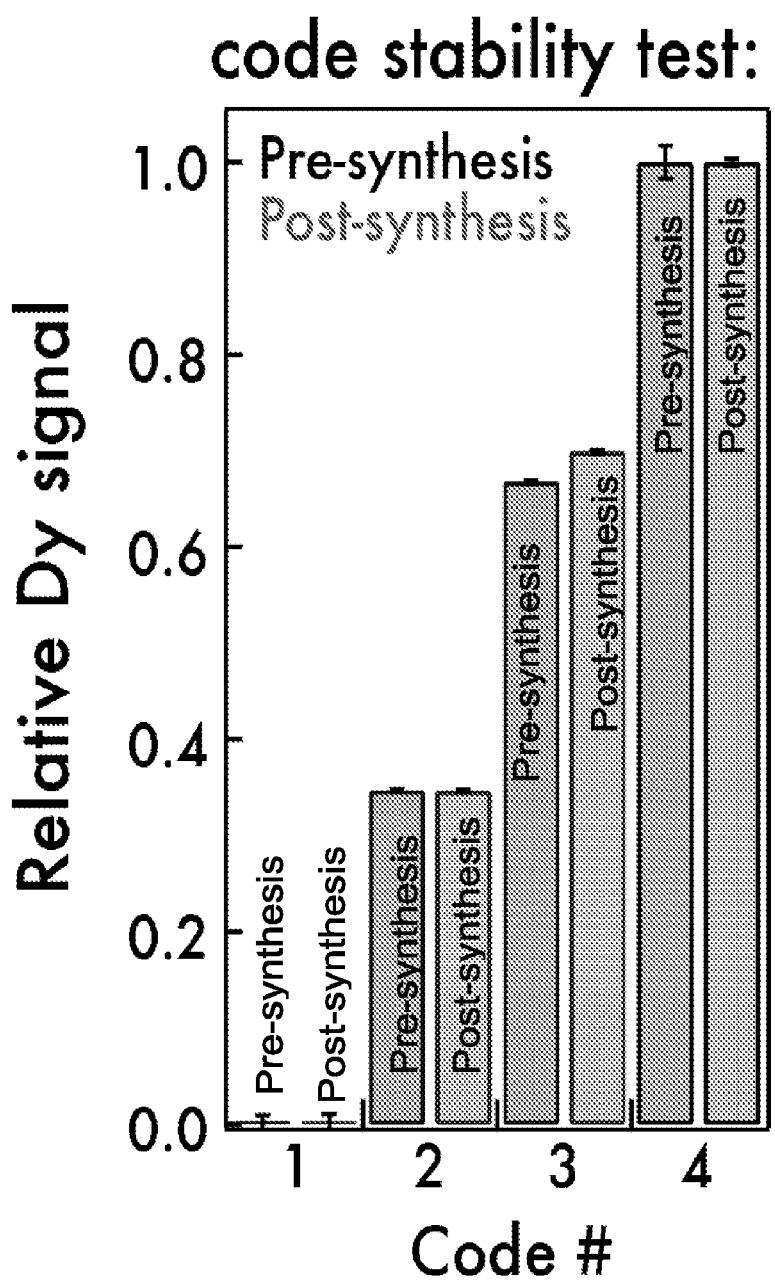
FIG. 14 provides a graph showing relative Dy signal present within a 4-code bead set before and after peptide synthesis.

Finally, a 4-code set of beads containing an identical amount of Eu nanocrystals and varying amounts of Dy nanocrystals (0%, 33%, 66%, and 100%) was synthesized and imaged before and after peptide synthesis to further probe code stability following synthesis. The relative amounts of Dy nanocrystals remained unchanged before and after synthesis (FIG. 14).

Single Bead Release for Microfluidic Sorting

Figure 15:
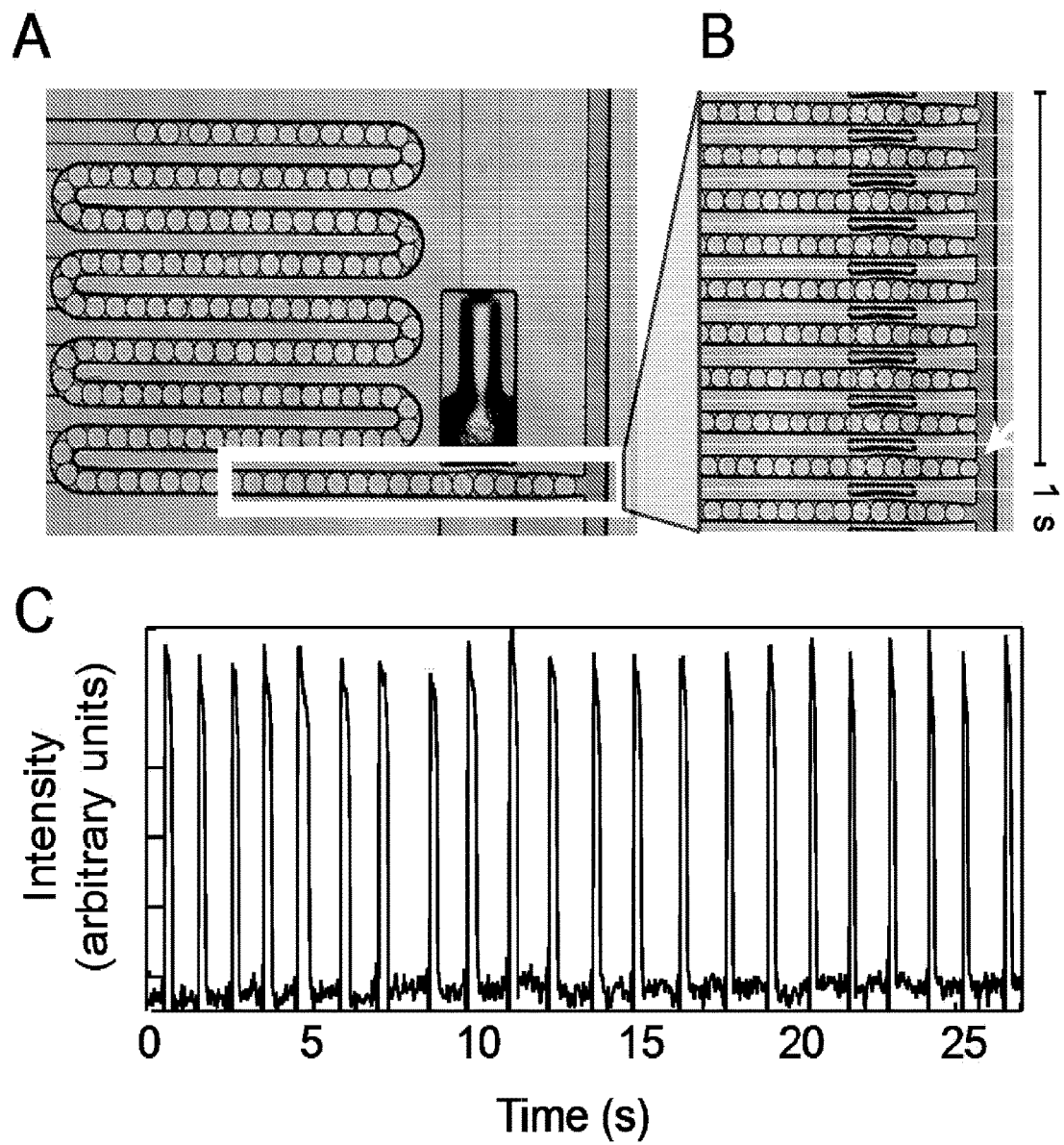
FIG. 15 demonstrates single bead release through the use of a single constriction in a microfluidic channel. (Panel A) Photograph of a linear serpentine channel for imaging of spectrally encoded beads in a first-in first-out linear array. (Panel B) Montage of images from a movie showing release of a single bead. (Panel C) Graph showing changes in intensity at the exit of the serpentine channel as a function of time. Increases in intensity indicate the passage of individual beads at fairly regular intervals.

In order to automate the sorting of beads for programmable peptide synthesis, it may be advantageous to image arrays of beads and then release the beads one-at-a-time for downstream sorting. This capability was demonstrated by including a small constriction (wherein each side of the channel narrows between 10 and 20 µm over a 100 µm distance) at the outlet of a microfluidic, serpentine channel (FIG. 15). Without intending to be bound by any particular theory, this small constriction creates a pressure instability (known as the Haine's jump instability) at the beads pass through the constriction, which leads to metering of beads one-by-one at the channel outlet. The ability to release beads one at a time may also be beneficial for a variety of bead uses outside of the peptide synthesis field. Accordingly, this feature has broad applicability to microfluidic devices in general.

Example 5: Synthesis and Characterization of Er:YVO4 and Tm:YVO4

Materials and Methods

Materials for Tm and Er:

YVO4 Synthesis: All chemical reagents and polymers [poly(ethylene glycol) (PEG) and poly(acrylic acid) (PAA)] for nanophosphor synthesis were purchased from Sigma-Aldrich (St. Louis, Mo.) and were used without further purification. Microwave synthesis was performed using a Biotage Initiator (Biotage AB, Uppsala, Sweden). Purification of the synthesized nanophosphors was performed by ultrafiltration using Amicon Ultra-15 centrifugal filter units with a 30,000 MWCO (Millipore, Billerica, Mass.), resulting in suspensions with a nanophosphor concentration of ~50 mg/mL in water. Luminescence spectra were measured using a FluoroMax-3 (Horiba Scientific, Kyoto, Japan) spectrofluorometer.

Typical Synthesis of Tm:

$YVO_4$ and Er: $YVO_4$: Solutions (0.1 M) of the rare-earth (RE) dopants [$Tm(NO_3)_3$, $Er(NO_3)_3$], $Y(NO_3)_3$, and $Na_3VO_4$ were prepared beforehand. A solution of $Y(NO_3)_3$ and the rare earth solution was premixed (950 µL Y and 50 µL Tm for Tm:YVO4, or 950 µL Y and 50 µL Er for Er:$YVO_4$) and added rapidly to 2 mL of a 10 w/w % solution of PEG (Mn~2,000) being stirred at 70° C. in an oil bath under magnetic stirring. This solution was stirred for 20 minutes, followed by the drop-wise addition of the $Na_3VO_4$ solution (950 μL). The suspension turned yellowish at this stage and the mixture was again stirred for 30 min. The suspension was transferred into a glass vial suitable for microwave synthesis and was heated to 180° C. at 15 bar for 90 min Upon removal from the microwave, the suspension was pure white. The material was pelleted in a 15-mL disposable centrifuge tube and the PEG supernatant was removed. The pellet was then re-suspended in 3 mL of deionized $H_2O$, to which was added 5 mL of a 10 w/w % PAA solution (Mn~1,400). This mixture was heated back up to 70° C. and stirred for 10 min. The solution was pH adjusted to 7.5 using 5 N NaOH and stirred for an additional 30 min. The suspension was then diluted 1:10 with deionized $H_2O$ and sonicated for 18 hours. After sonication, any larger phosphor particles were pelleted under centrifugation and the remaining translucent suspension was filtered consecutively through 1 μm and 0.45 μm PTFE filters before being added to an ultracentrifugation filter unit for concentration and the removal of excess salts and polymers. After the entire reaction volume (~100 mL) had been passed through the membrane, the retained nanophosphors were washed 4 times with 15 mL of deionized water to exchange out the remaining solution. The final NP suspensions were white and milky in appearance and had a nanophosphor concentration of about 50 mg/mL.

Synthesis and Characterization of Er: $YVO_4$ and Tm: $YVO_4$

Figure 16:
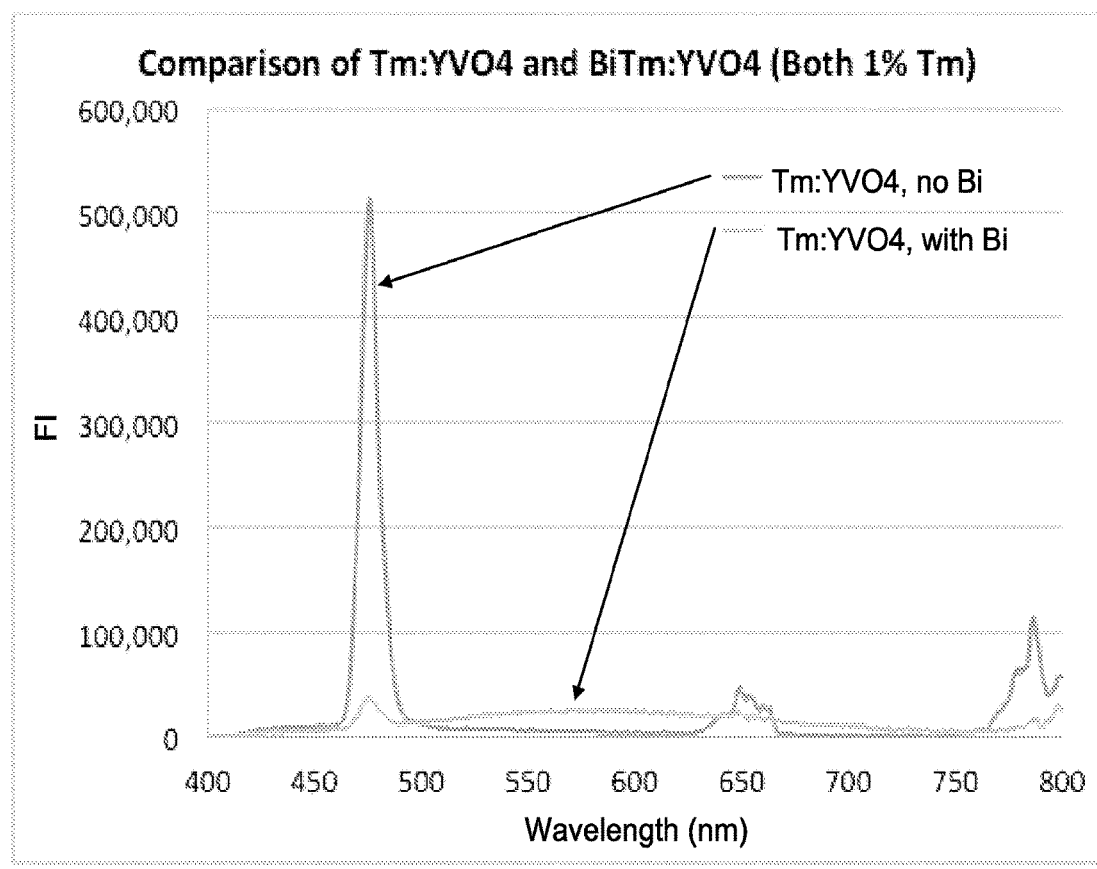
FIG. 16 provides a luminescence spectra of Tm:YVO$_4$ with and without bismuth. Tm loading is 1% in both cases and bismuth is incorporated at ~15-20% replacement of Yttrium (Y).
Figure 17:
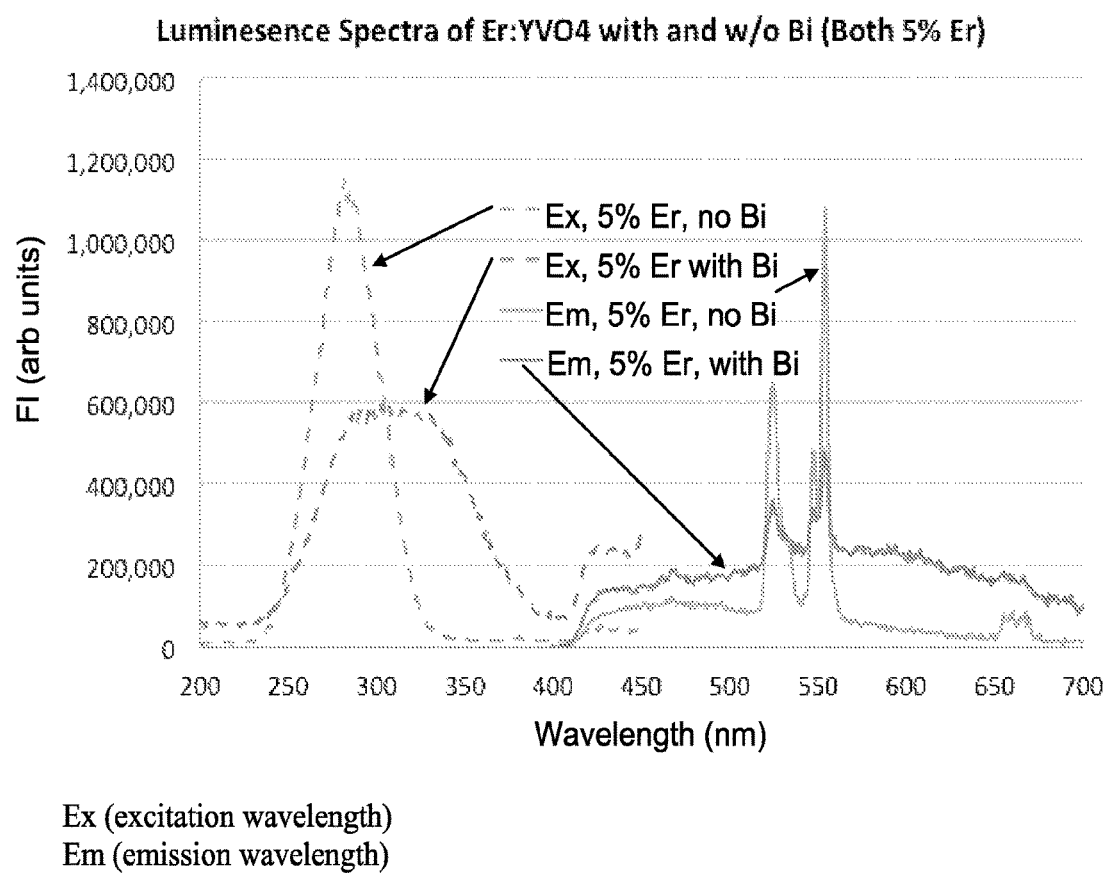
FIG. 17 provides a luminescence spectra of Er:YVO$_4$ with and without bismuth (Bi). Er loading is 5% in both cases and bismuth is incorporated at ~15-20% replacement of Yttrium (Y).

Following on the successful synthesis and incorporation of Eu, Sm, and Dy phosphors into beads as discussed previously herein, a similar process was sought for additional rare earths Er and Tm, both of which can also be doped into a $YVO_4$ crystalline matrix to emit visible light when excited with ultraviolet light. To varying extents depending on the rare earth dopant (emitter) being used, the incorporation of bismuth into the lattice in addition to the rare earth dopant has a tendency to diminish the luminescence of that emitter. This was found to be the case for both Tm and Er, where their counterparts with bismuth synthesized using the protocols disclosed herein demonstrated relatively low luminescence. The non-bismuth material, however, showed sufficient luminescence for both emitters (FIGS. 16 and 17) to warrant further investigation. Originally, bismuth was incorporated to shift the excitation wavelength maximum from 280 nm to roughly 320 nm when bismuth is sufficiently incorporated into the matrix. However, it was determined that by using the illumination optics disclosed herein to read the codes, the excitation region around 280-300 nm was sufficiently covered such that the non-Bi-containing nanophosphors could be examined.

Figure 18:
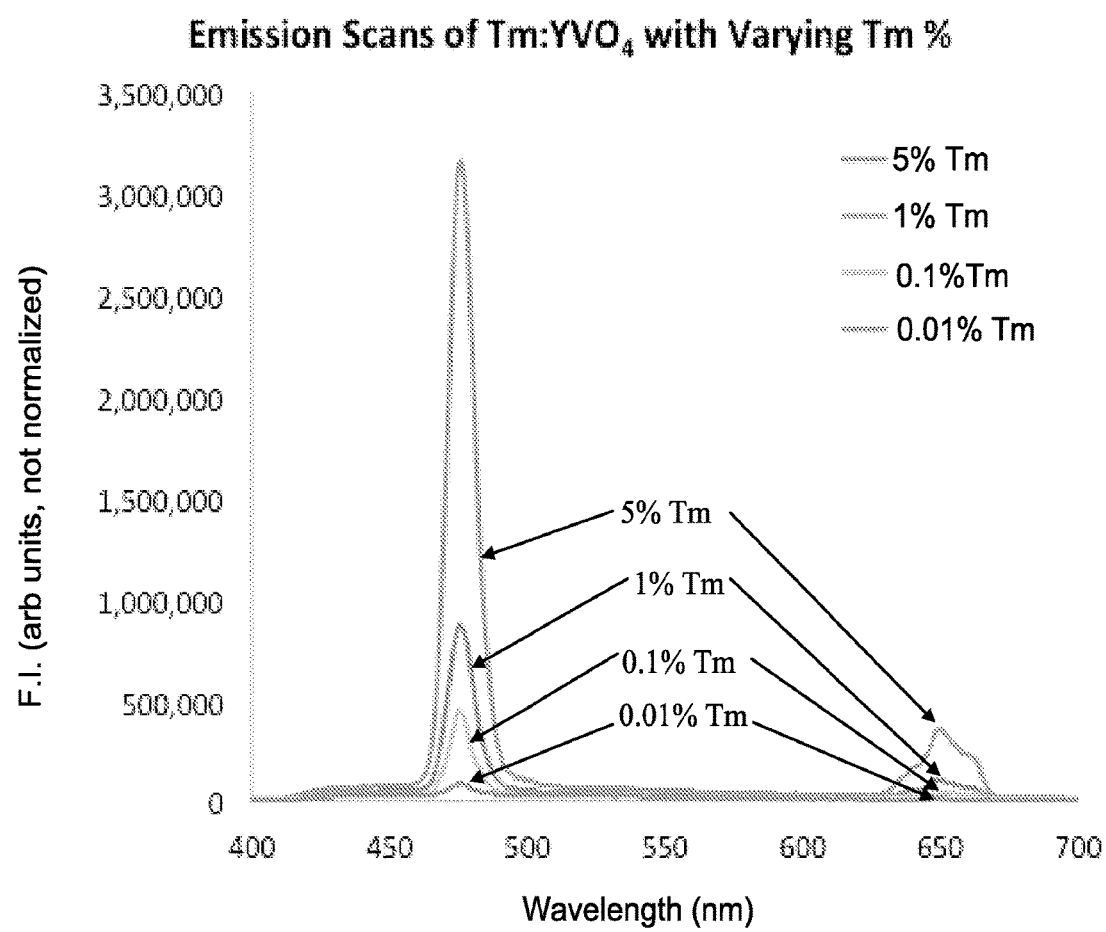
FIG. 18 provides an emission scan of Tm:YVO$_4$ with varying Tm %. The emission scan shows adjustment of the Tm % loading to arrive at a preferred value of 1% Tm:YVO$_4$. Nanoparticle concentrations in these solutions are approximately constant (up to 5% variance in concentration).

The loading levels of both Er and Tm were adjusted by synthesizing small batches of $YVO_4$ with increasing Tm or Er doping concentration in order to observe a doping level that maximized the luminescence. FIG. 18 shows this progression for Tm and FIG. 19 for Er. A preferred stoichiometry for Tm was 1% loading, or $Tm_{0.01}Y_{0.99}VO_4$. Tm:$YVO_4$ suffers from autoquenching of the luminescence when the Tm loading gets too high, as was observed in going from 1% to 5% Tm doping.

Figure 19:
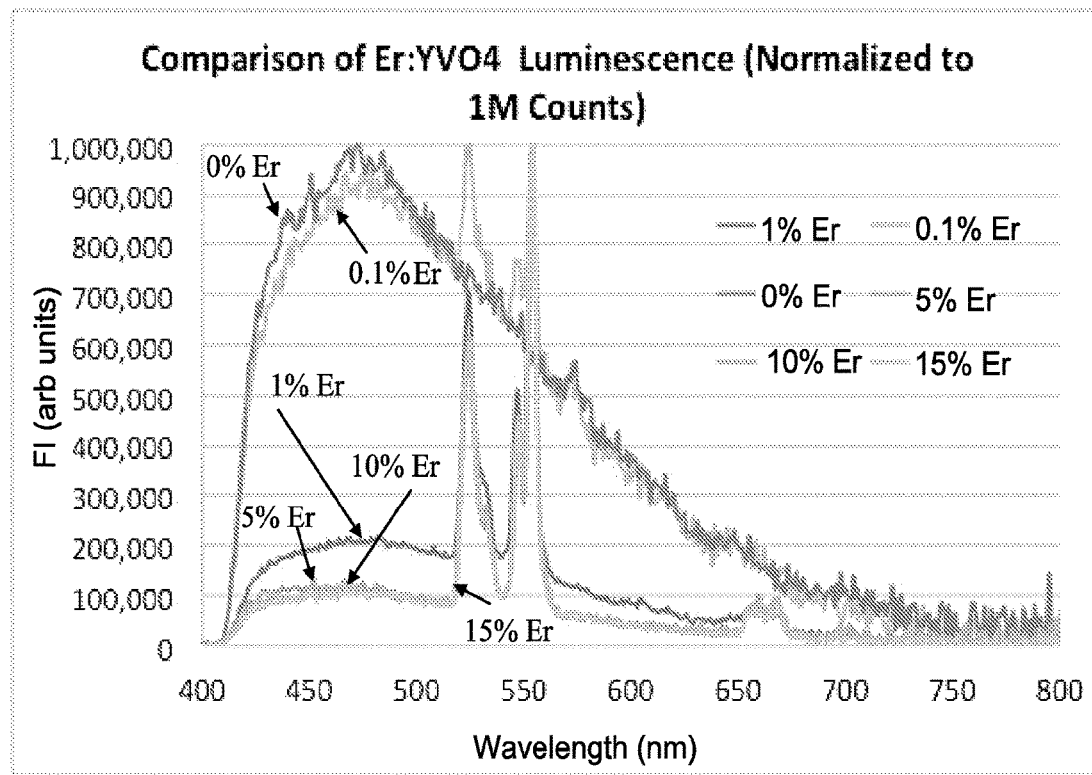
FIG. 19 provides a graph showing a comparison of Er:YVO$_4$ luminescence (normalized to 1M counts). The graph shows adjustment of the Er % loading to arrive at a preferred value of 5% Er:YVO$_4$. Nanoparticle concentrations in these solutions are approximately constant (up to 5% variance in concentration).

FIG. 19 demonstrates that the inherent brightness or luminescence of a nanophosphor solution may be compared by examining the peak luminescent intensity against the background luminescence of the $YVO_4$ matrix. When higher Er concentrations were plotted as non-normalized spectra, there is enough variance in solution concentration, particle size, etc. to show significant differences between the excitation spectra (not shown here). However, plotted as normalized spectra as in FIG. 19, it is easier to see that the luminescence of the Er peaks at 524 and 554 nm increase as the Er doping is increased from 0.1% up to 5% and then additional loading (10 and 15% dopant) has a negligible effect on the luminescence. For this reason, 5% loading was chosen as the preferred loading level for Er, or $Er_{0.05}Y_{0.95}VO_4$.

Example 6: Synthesis and Characterization of CeTb:LaPO4

Materials and Methods

To a 20 mL microwave synthesis vial containing 10 mL $H_2O$ was added 155 mg $LaCl_3.7H_2O$, 165 mg $CeCl_3.7H_2O$, and 57.6 mg $TbCl_3.6H_2O$. 370 mg of $Na_5P_3O_{10}$ was dissolved separately in 4 mL of $H_2O$ and then added dropwise to the chlorides in the microwave vial. The vial was capped and heated to 180° C. for 60 min. The material was pelleted in a 15-mL disposable centrifuge tube and the supernatant was removed. The pellet was then re-suspended in 5 mL of deionized $H_2O$, to which was added 10 mL of a 10 w/w % PAA solution (Mn~1,400). This mixture was heated back up to 70° C. and stirred for 10 min. The solution was pH adjusted to 7.5 using 5 N NaOH and stirred for an additional 30 min. The suspension was then diluted 1:10 with deionized $H_2O$ and sonicated for 18 hours. After sonication, any larger phosphor particles were pelleted under centrifugation and the remaining translucent suspension was filtered consecutively through 1 μm and 0.45 μm PTFE filters before being added to an ultracentrifugation filter unit for concentration and the removal of excess salts and polymers. After the entire reaction volume (~100 mL) had been passed through the membrane, the retained nanophosphors were washed 4 times with 15 mL of deionized water to exchange out the remaining solution. The final NP suspensions were white and milky in appearance and had a nanophosphor concentration of about 200 mg/mL.

Characterization of $CeTb:LaPO_4$

Figure 20:
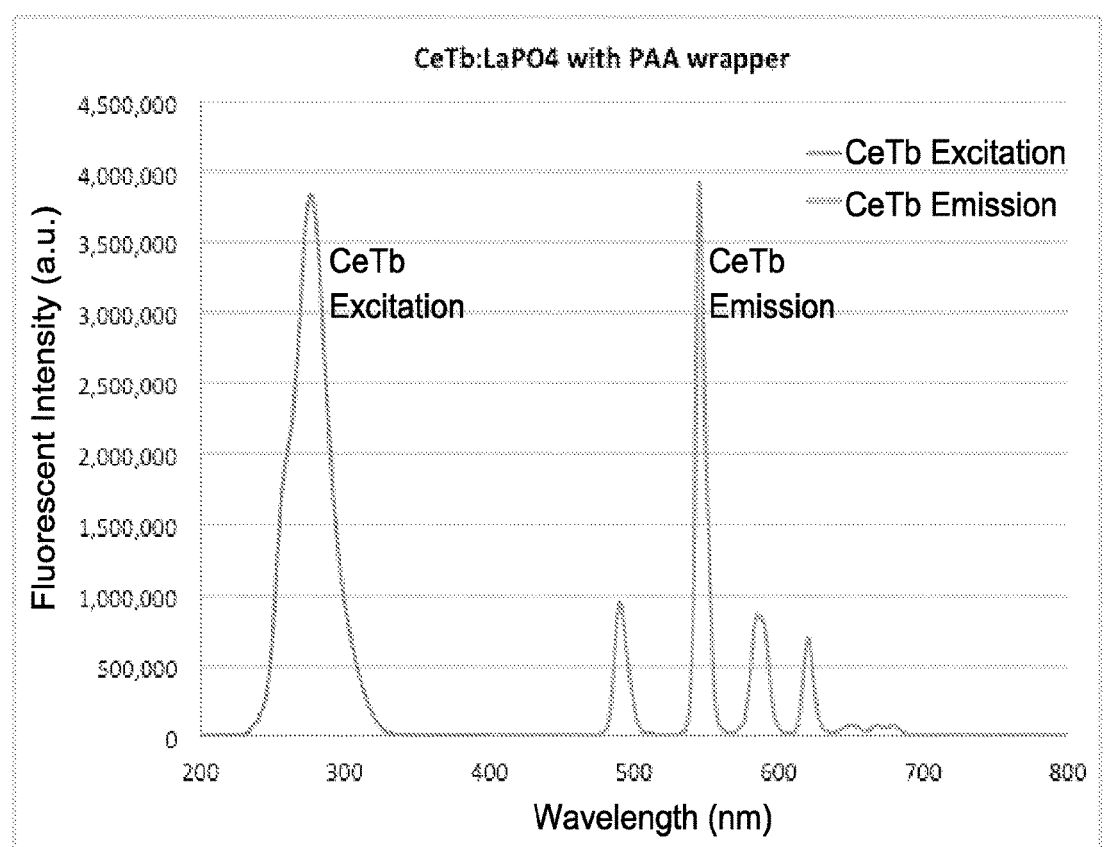
FIG. 20 provides a luminescence spectra of the CeTb:LaPO$_4$ nanophosphor.
Figure 21:
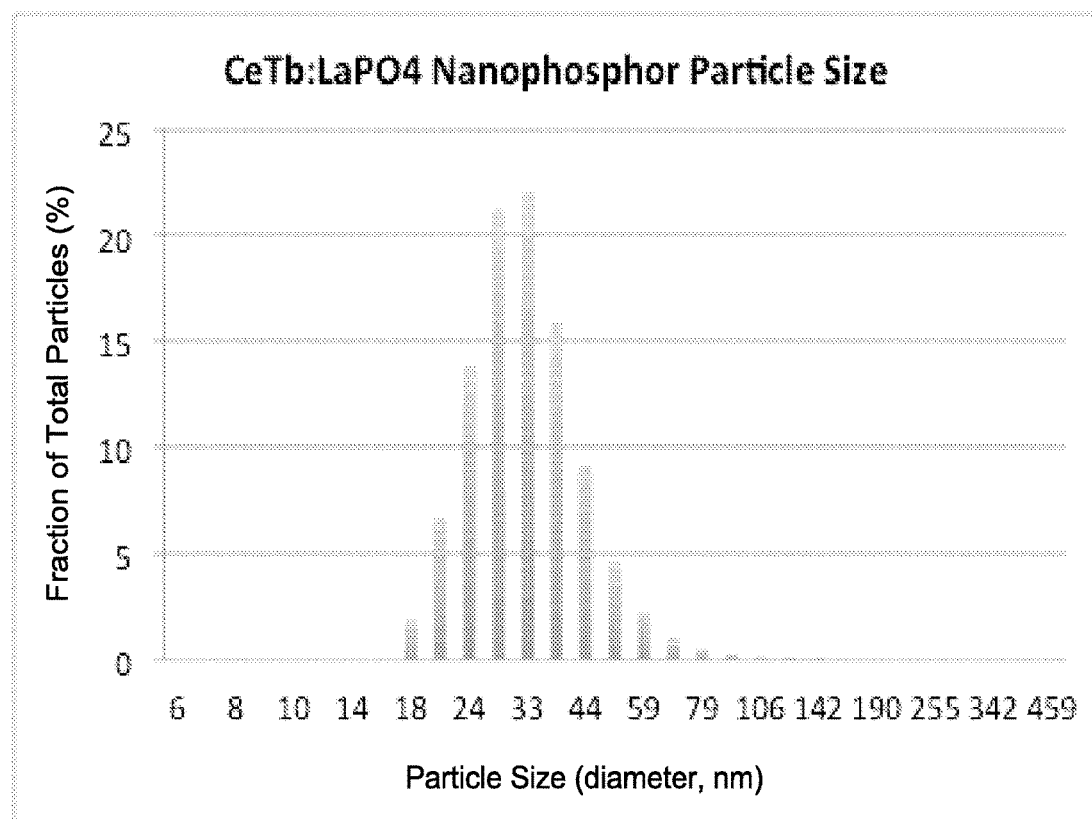
FIG. 21 provides a graph showing the results of a particle size analysis of the CeTb:LaPO$_4$ nanophosphor.

FIG. 20 shows the excitation and emission spectra for the $CeTb:LaPO_4$ nanophosphor suspension with an excitation maximum of 275 nm and excitation peaks at 490, 545 (most intense), 585, and 620 nm FIG. 21 shows the particle size distribution as measured by dynamic light scattering with an average particle size of 34 nm.

Example 7: Monomer Development and Synthesis

As previously described herein poly(ethylene glycol) diacrylate (PEG-DA) was used as a monomer in the preparation of microbeads according to the present disclosure. While beads made from this monomer may work when evaluated for start-to-finish feasibility and stability with respect to peptide synthesis and the subsequent biological assays to be performed, it is possible that the ester bonds of PEG-DA may be too acid- and base-sensitive to for such applications. For this reason, acrylamide bond formation was investigated as a possible alternative bead chemistry for use in peptide synthesis applications.

PEG diacrylamide (PEG-DAM) was initially prepared from a commercially-available PEG-diamine source. The formula for the original PEG diacrylate (PEG-DA) and the initial synthesis scheme for the PEG diacrylamide (PEG-DAM) are shown below:

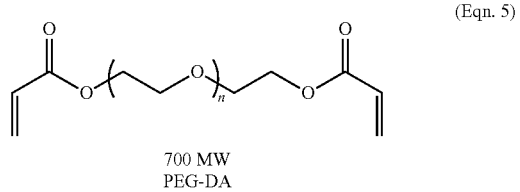

(Eqn. 5)

700 MW
PEG-DA

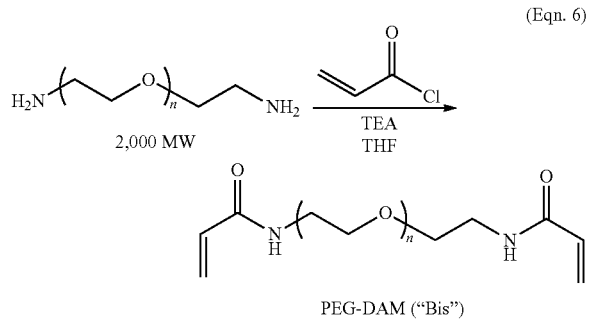

(Eqn. 6)

PEG-DAM ("Bis")

Figure 22:
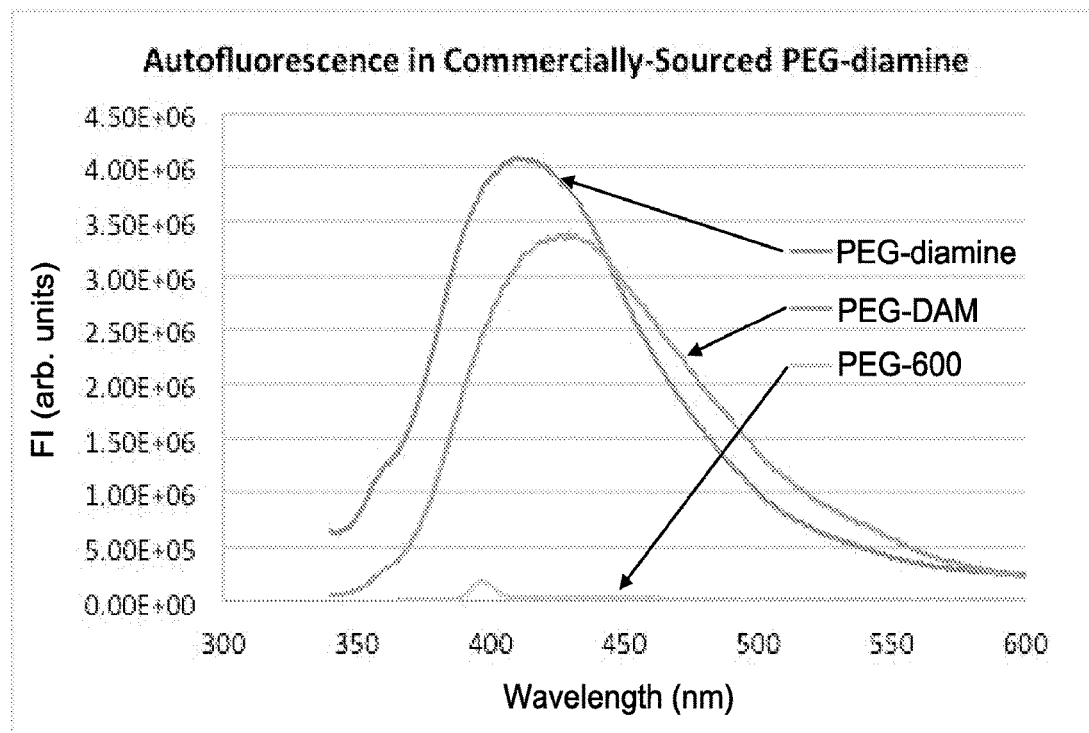
FIG. 22 provides emission spectra for commercially available PEG-diamine and the PEG-DAM synthesized from it. As a comparison, a commercially available PEG-600 is included to illustrate an acceptable level of autofluorescence for a PEG.

The above synthesis of PEG-DAM from a commercially-available PEG-diamine source was readily achieved. However, when tested with the beads, the PEG-DAM exhibited an unacceptably high autofluorescence when excited with ultraviolet light. The autofluorescence was observed for both the starting material (PEG-diamine) and the final PEG-DAM product (FIG. 22). FIG. 22 provides emission spectra for commercially available PEG-diamine and the PEG-DAM synthesized from it. As a comparison, a commercially available PEG-600 is included to illustrate an acceptable level of autofluorescence for a PEG.

In view of the above results, it was determined that a new source for this monomer was needed. The following reaction scheme and synthesis procedure was tested:

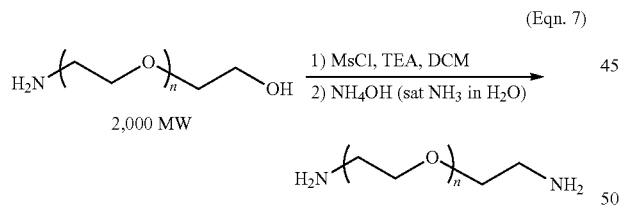

(Eqn. 7)

Synthesis of PEG2K-Diamine from PEG2K:

20 g of PEG2K (2000 MW PEG) was added to a 500-mL round bottom flask containing 200 mL dichloromethane. 8.37 mL (3 equiv) of triethylamine was added and the flask was chilled to 0° C. while being stirred. 3.6 mL (2.2 equiv) of mesyl chloride was added dropwise and the solution was stirred overnight. About half of the dichloromethane was removed the next morning by rotary evaporation and the solids (triethylamine hydrochloride salt) were filtered out using a Buchner funnel. Next, a small portion of diethyl ether was added to further precipitate more triethylamine salt and this was again filtered. This filtrate was then slowly poured into a 1-L Erlenmeyer flask with 600 mL diethyl ether to precipitate the PEG-dimesylate product. This was used in the next step without further purification. Using an aliquot of the crude dimesylate, 7.2 g of PEG-dimesylate was added to a 500-mL glass Nalgene serum bottle with a stir bar and 150 mL $NH_4OH$ (conc). This was stirred in the sealed bottle for 4 days. The $NH_3(g)$ was removed under partial vacuum followed by the removal of ~50 mL $H_2O$ after the $NH_3$ had been removed. This solution was made basic (pH 12-13) with 5 N NaOH and was transferred to a 250-mL separatory funnel where the aqueous layer was extracted 8 times with 40 mL dichloromethane. The dichloromethane extracts were pooled and dried over $K_2CO_3$ and the solution was transferred to a round bottom flask where the solvent was removed to yield ~10-15 g of a yellowish liquid. This was added dropwise into 350 mL of stirring diethyl ether to precipitate out the final product. The product was removed by filtration through a Buchner funnel and was dried under vacuum until no ether was present. The final product was 6.0 g of a white powder (80% yield).

Figure 23:
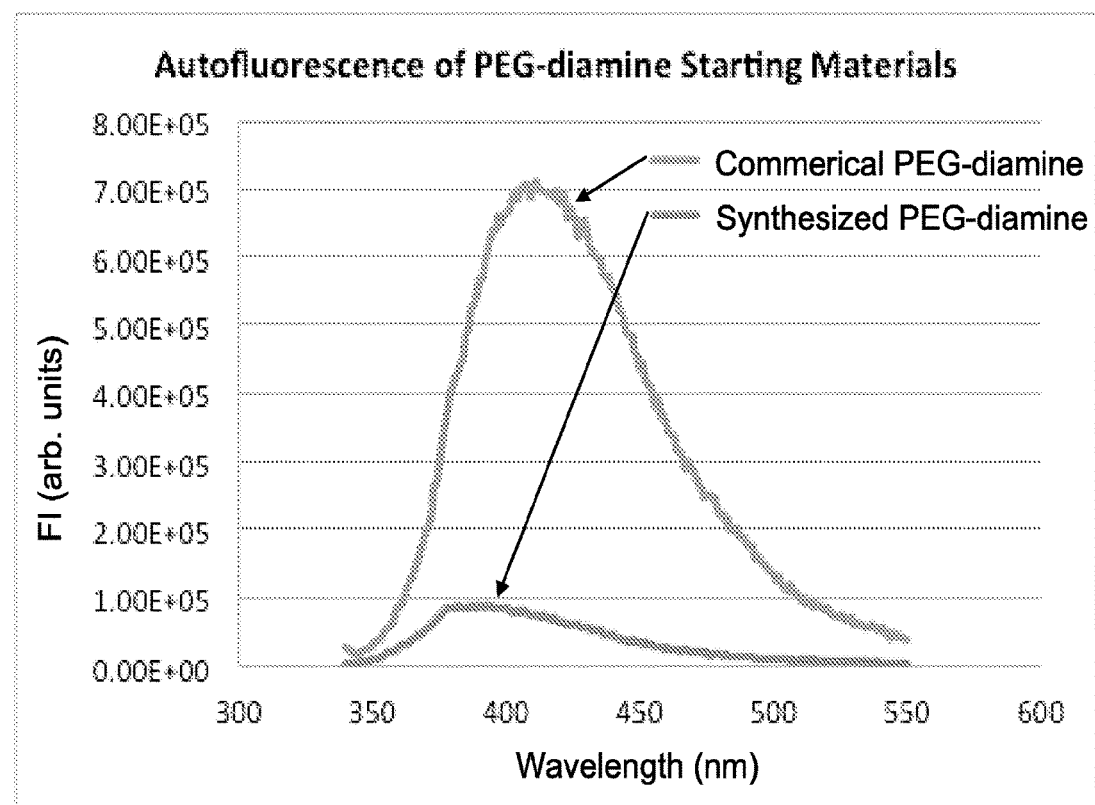
FIG. 23 provides emission spectra showing a comparison of the autofluorescence between the commercially available PEG-diamine and the PEG-diamine synthesized from PEG2K as described herein.

The PEG-diamine synthesized as described above exhibited lower absorption in solution by UV-vis as well as significantly less autofluorescence as observed by the spectrofluorometer. The comparison of autofluorescence is shown in FIG. 23.

The synthetic schemes for PEG-diamine to PEG-DAM (Eqn. 8), PEG-AM (Eqn. 9), and PEG-monoacrylamide-monoBoc (Eqn. 10) are provided below:

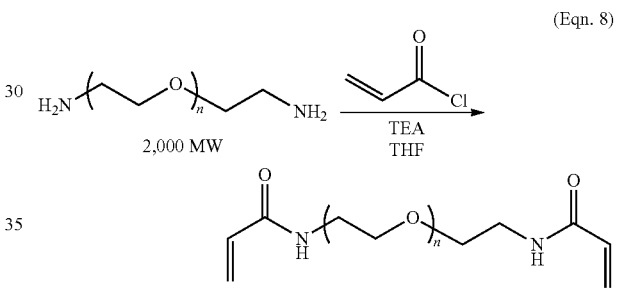

(Eqn. 8)

PEG-DAM ("Bis")

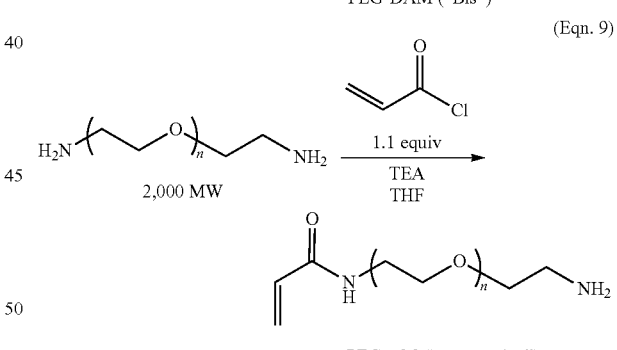

(Eqn. 9)

PEG-AM ("monoamine")

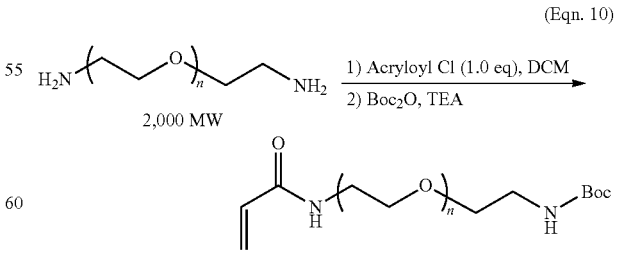

(Eqn. 10)

To obtain the PEG-DAM, PEG-diamine was reacted with acryloyl chloride (Eqn. 8). 2.0 g of PEG2K-diamine (with 2 equivalents of amine groups present per molecule of PEG) was added to a 250 mL round bottom flask along with 100 mL tetrahydrofuran (THF). 1120 μL triethylamine was added and the solution was chilled to 0° C. 243 μL acryloyl chloride in 2 mL of THF was added dropwise to the flask and the mixture was stirred in the dark for 90 minutes with the flask returning to room temperature after the first 15 minutes. The mixture was then filtered to remove the triethylamine hydrochloride salt and the THF was removed using the rotary evaporator. The residue was taken up into 75 mL dichloromethane and transferred to a separatory funnel. The organic layer was washed once with 100 mL of saturated NaCl. The organic layer was saved and the brine layer was washed 4 times with 50 mL dichloromethane. All of the dichloromethane extracts were pooled and dried over $K_2CO_3$. The dichloromethane was removed by rotary evaporator until ~10 mL of residue remained in the flask. This was added dropwise into 300 mL of stirring diethyl ether to precipitate the product. The product was isolated using a Buchner funnel and was dried under vacuum until no diethyl ether was detectable.

PEG-AM (Eqn. 9) was synthesized the same way as PEG-DAM except that no triethylamine is needed since the remaining amine on the PEG-diamine catalyzes the reaction. There is also a simpler work-up with no extraction for PEG-AM.

Some initial testing has indicated that there are times when the nanoparticle solutions tend to aggregate and become incompatible with the monomer mixture before polymerization. This was observed occasionally with PEG-DA, but the issues were always resolved. This aggregation has also been observed with PEG-DAM and to a greater extent with PEG-AM. The aggregation also appears to be more prevalent when PEG-AM is introduced with amines present. To address this issue, a monomer with a functional amine was suggested and successfully synthesized to test the nanoparticle compatibility: one of these types of molecules is shown in (Eqn. 10) and is called PEG-monoacrylamide-monoBoc where the Boc carbamate is protecting the amine that may be responsible for the nanoparticle aggregation issues.

Figure 24:
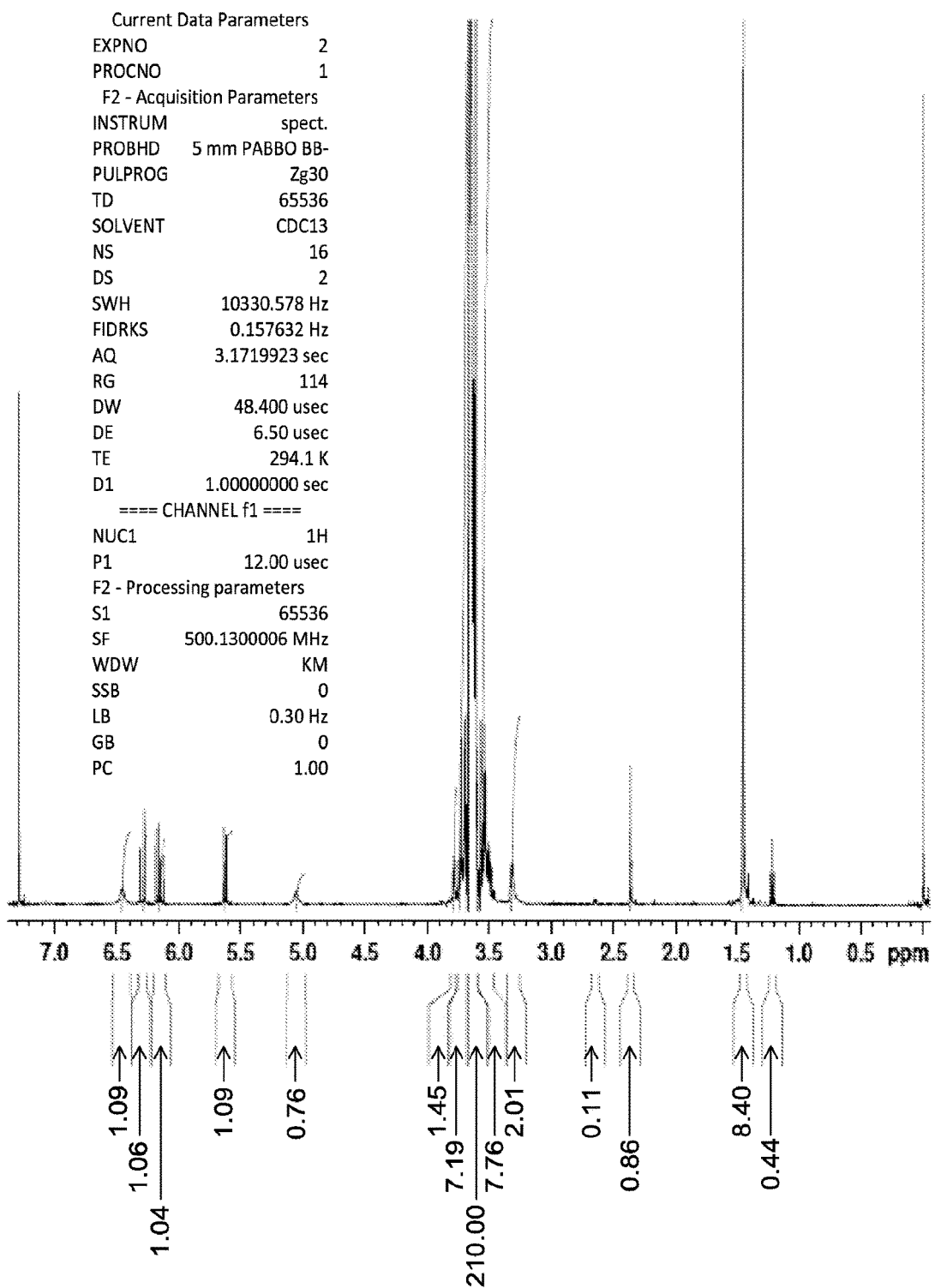
FIG. 24 provides a proton NMR readout showing the synthesis of PEG2K-monoacrylamide-monoBoc.

The synthesis of the PEG-monoacrylamide-monoBoc is the same as for the PEG-AM, but while still in solution, 2 equivalents of $Boc_2O$ are added to the solution and the solution is stirred overnight in the dark. This solution is extracted with brine to remove the triethylamine salt and then ultimately precipitated into diethyl ether as with all the other PEGs in this series of compounds. The NMR (FIG. 24) shows a clean product with no free amines. Future testing will be performed to determine compatibility with the nanophosphors and the ability to produce polymerized beads.

What is claimed is:

1. A method for producing a population of polymeric microbeads comprising a plurality of different lanthanide nanoparticles, the method comprising:
  (i) mixing, in a microfluidic device, at least a first fluid and a second fluid together to form a solution,
    wherein the first fluid comprises a first lanthanide nanoparticle, a photoinitiator, and a photo-polymerizable monomer and/or polymer component,
    wherein the second fluid comprises a second lanthanide nanoparticle, a photoinitiator, and a photo-polymerizable monomer and/or polymer component, and
    wherein the first lanthanide nanoparticle comprises a lanthanide element that is not present in the second lanthanide nanoparticle;
  (ii) forming, in the microfluidic device, a first plurality of droplets from the solution; and
  (iii) subjecting, in the microfluidic device, the first plurality of droplets to polymerization conditions comprising exposing the first plurality of droplets to UV radiation,
    wherein the polymerization conditions are sufficient to polymerize the photo-polymerizable monomer and/or polymer components,
  to produce a first plurality of polymeric microbeads embedded with at least the first lanthanide nanoparticle and the second lanthanide nanoparticle, wherein the relative concentrations of the first lanthanide nanoparticle and the second lanthanide nanoparticle are substantially equal among the polymeric microbeads of the first plurality of polymeric microbeads.

2. The method as set forth in claim 1, wherein the luminescence intensity level variation among all the members of the first plurality of polymeric microbeads is no greater than about 15 percent.

3. The method as set forth in claim 1, wherein the luminescence intensity level variation among all the members of the first plurality of polymeric microbeads is no greater than about 5 percent.

* * * * *